(12) United States Patent
Jaeger et al.

(10) Patent No.: US 11,994,246 B2
(45) Date of Patent: May 28, 2024

(54) HYDRATION SYSTEM AND COMPONENTS THEREOF

(71) Applicant: RAINMAKER SOLUTIONS, INC., El Segundo, CA (US)

(72) Inventors: Eduard Jaeger, El Segundo, CA (US); Robert Stahl, Marina Del Rey, CA (US); Jacob Bowles, El Segundo, CA (US)

(73) Assignee: RainMaker Solutions, Inc., El Segundo, CA (US)

( * ) Notice: Subject to any disclaimer, the term of this patent is extended or adjusted under 35 U.S.C. 154(b) by 0 days.

(21) Appl. No.: 17/494,814

(22) Filed: Oct. 5, 2021

(65) Prior Publication Data

US 2022/0026000 A1 Jan. 27, 2022

Related U.S. Application Data

(63) Continuation of application No. 15/653,439, filed on Jul. 18, 2017, now Pat. No. 11,137,098.

(Continued)

(51) Int. Cl.
*A45F 3/20* (2006.01)
*A42B 3/04* (2006.01)
(Continued)

(52) U.S. Cl.
CPC .......... *F16L 37/004* (2013.01); *A42B 3/0406* (2013.01); *A45F 3/04* (2013.01); *A45F 3/16* (2013.01); *A45F 3/20* (2013.01); *A47G 21/185* (2013.01); *A62B 18/086* (2013.01); *B60R 16/027* (2013.01); *B65D 47/2031* (2013.01);
(Continued)

(58) Field of Classification Search
CPC ........ F16L 37/004; F16L 33/18; F16L 33/20; F16L 33/32; F16L 37/0841; A42B 3/0406; A42B 3/048; A45F 3/04; A45F 3/16; A45F 3/20; A45F 3/005; A45F 3/14; A45F 2003/003; A45F 2003/166; A45F 2200/0583; A47G 21/185; A62B 8/086; B60R 16/027; B65D 47/2031; B67D 1/0004; B67D 1/0888; B67D 1/0891; B67D 1/10; B67D 1/1277; B67D 2210/00131; F04B 17/06; F04B 49/06; F04D 5/007; F04D 15/0281; F04D 29/4293;
(Continued)

(56) References Cited

U.S. PATENT DOCUMENTS 3,181,895 A * 5/1965 Cator .................... F16L 37/004
285/1
5,085,349 A * 2/1992 Fawcett ............. A47G 19/2266
224/148.2

(Continued)

*Primary Examiner* — Kerri L McNally
*Assistant Examiner* — Thang D Tran
(74) *Attorney, Agent, or Firm* — Orbit IP, LLP

(57) ABSTRACT

A hydration system including a fluid reservoir, a fluid path in communication with the reservoir, and a magnetic quick connect interposed in the fluid path is disclosed. A fluid delivery system for a hydration system is also disclosed that includes a magnetic quick connect interposed in a fluid delivery path of the delivery system. The magnetic quick connect can also be used in a wide variety of fluid delivery systems. A kit for forming a fluid delivery system for a hydration system is also disclosed, as are various components of a hydration system.

24 Claims, 29 Drawing Sheets

Related U.S. Application Data

(60) Provisional application No. 62/423,756, filed on Nov. 17, 2016, provisional application No. 62/363,334, filed on Jul. 18, 2016.

(51) Int. Cl.

| | | |
|---|---|---|
| *A45F 3/04* | (2006.01) | |
| *A45F 3/16* | (2006.01) | |
| *A47G 21/18* | (2006.01) | |
| *A62B 18/08* | (2006.01) | |
| *B60R 16/027* | (2006.01) | |
| *B65D 47/20* | (2006.01) | |
| *B67D 1/00* | (2006.01) | |
| *B67D 1/08* | (2006.01) | |
| *B67D 1/10* | (2006.01) | |
| *B67D 1/12* | (2006.01) | |
| *F04B 17/06* | (2006.01) | |
| *F04B 49/06* | (2006.01) | |
| *F04D 5/00* | (2006.01) | |
| *F04D 15/02* | (2006.01) | |
| *F04D 29/42* | (2006.01) | |
| *F16L 33/18* | (2006.01) | |
| *F16L 33/20* | (2006.01) | |
| *F16L 33/32* | (2006.01) | |
| *F16L 37/00* | (2006.01) | |
| *F16L 37/084* | (2006.01) | |
| *G05D 7/06* | (2006.01) | |
| *A45F 3/00* | (2006.01) | |
| *A45F 3/14* | (2006.01) | |
| *A61M 39/10* | (2006.01) | |
| *B62K 21/00* | (2006.01) | |
| *B62K 21/12* | (2006.01) | |

(52) U.S. Cl.
CPC ......... *B67D 1/0004* (2013.01); *B67D 1/0888* (2013.01); *B67D 1/0891* (2013.01); *B67D 1/10* (2013.01); *B67D 1/1277* (2013.01); *F04B 17/06* (2013.01); *F04B 49/06* (2013.01); *F04D 5/007* (2013.01); *F04D 15/0281* (2013.01); *F04D 29/4293* (2013.01); *F16L 33/18* (2013.01); *F16L 33/20* (2013.01); *F16L 33/32* (2013.01); *F16L 37/0841* (2013.01); *G05D 7/0635* (2013.01); *G05D 7/0676* (2013.01); *A42B 3/048* (2013.01); *A45F 2003/003* (2013.01); *A45F 3/005* (2013.01); *A45F 3/14* (2013.01); *A45F 2003/166* (2013.01); *A45F 2200/0583* (2013.01); *A61M 39/10* (2013.01); *B62K 21/00* (2013.01); *B62K 21/12* (2013.01); *B67D 2210/00131* (2013.01); *F05D 2250/53* (2013.01)

(58) Field of Classification Search
CPC ... G05D 7/0635; G05D 7/0676; A61M 39/10; B62K 21/00; B62K 21/12; F05D 2250/53
USPC ....................................................... 340/12.1
See application file for complete search history.

(56) References Cited

U.S. PATENT DOCUMENTS

| | | | | |
|---|---|---|---|---|
| 5,113,657 | A * | 5/1992 | Compton | F16L 37/091 192/85.01 |
| 5,221,267 | A * | 6/1993 | Folden | A61M 1/28 604/905 |
| 5,797,889 | A * | 8/1998 | Steinman | A61M 39/10 604/533 |
| 5,940,880 | A * | 8/1999 | Phillips | A42B 3/048 222/401 |
| 5,975,387 | A * | 11/1999 | Gleason | A45F 3/16 224/640 |
| 6,283,344 | B1 * | 9/2001 | Bradley | A42B 3/048 224/148.2 |
| 7,793,987 | B1 * | 9/2010 | Busch | A61M 16/161 285/9.1 |
| 10,696,532 | B1 * | 6/2020 | Steele | A45F 3/16 |
| 2004/0254531 | A1 * | 12/2004 | Carr | A61B 5/15003 604/111 |
| 2006/0113336 | A1 * | 6/2006 | Spencer | A45F 3/20 2/268 |
| 2006/0180154 | A1 * | 8/2006 | Stone | A42B 3/048 128/206.13 |
| 2006/0231561 | A1 * | 10/2006 | Choi | A45F 3/20 224/148.2 |
| 2007/0021648 | A1 * | 1/2007 | Lenker | A61M 25/0097 600/29 |
| 2007/0181616 | A9 * | 8/2007 | Horito | A45F 3/20 224/148.2 |
| 2008/0308032 | A1 * | 12/2008 | Skillern | B63J 99/00 114/364 |
| 2009/0212081 | A1 * | 8/2009 | Liang | A45F 3/20 224/148.2 |
| 2011/0084474 | A1 * | 4/2011 | Paden | F16L 37/004 285/9.1 |
| 2012/0303054 | A1 * | 11/2012 | Wilson | A61M 25/104 156/294 |
| 2013/0186906 | A1 * | 7/2013 | Underhill | A45F 3/16 220/705 |
| 2014/0276636 | A1 * | 9/2014 | Lee | A61K 31/167 604/517 |
| 2015/0001253 | A1 * | 1/2015 | Slaton | A45F 3/20 222/144.5 |
| 2016/0090981 | A1 * | 3/2016 | Ryan | F04B 49/065 700/282 |
| 2016/0113379 | A1 * | 4/2016 | Marui | A45F 3/20 224/148.1 |
| 2016/0262525 | A1 * | 9/2016 | Lorbecki | A45F 3/04 |
| 2017/0022042 | A1 * | 1/2017 | Lux | B67D 1/0082 |

* cited by examiner

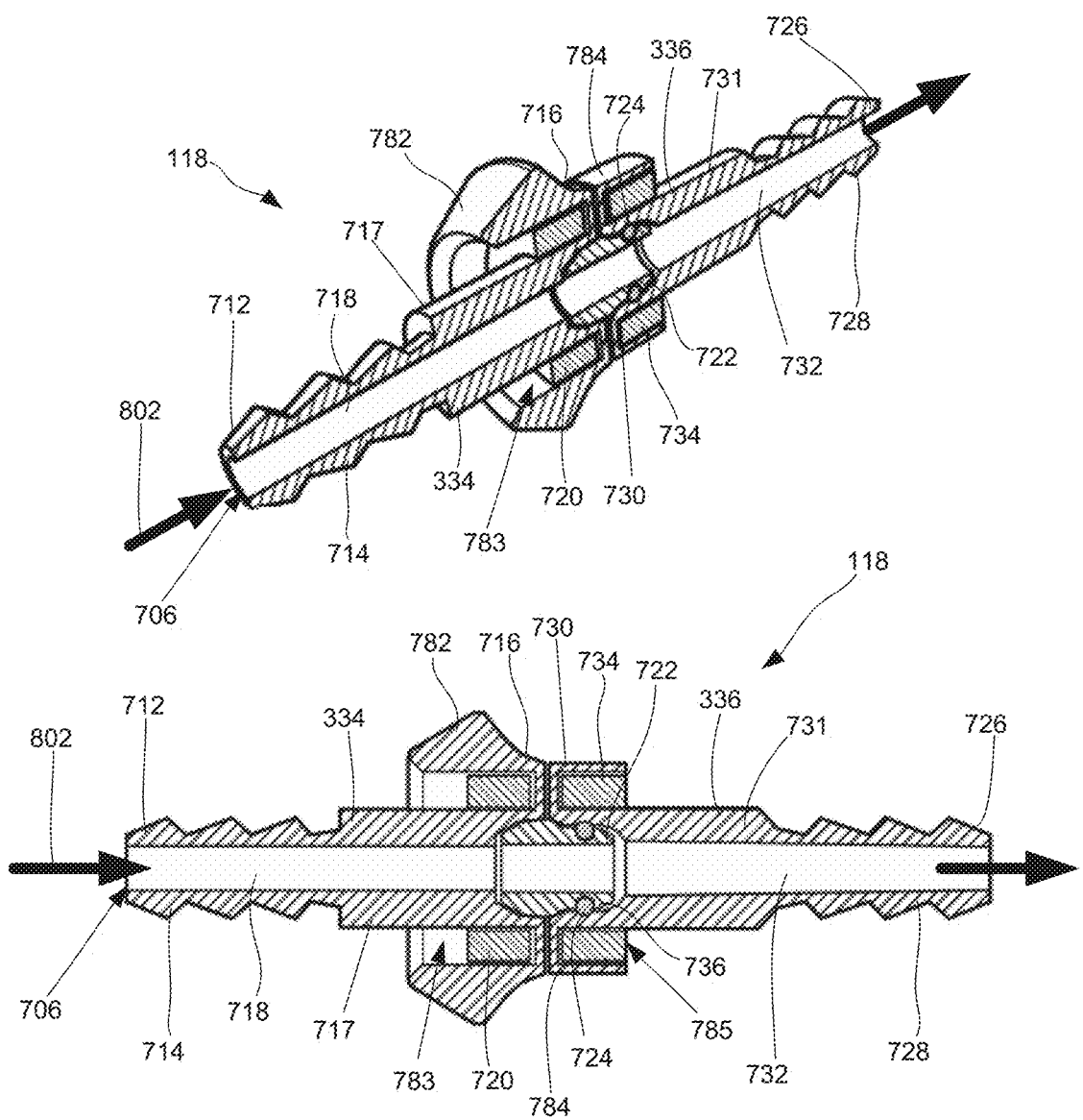

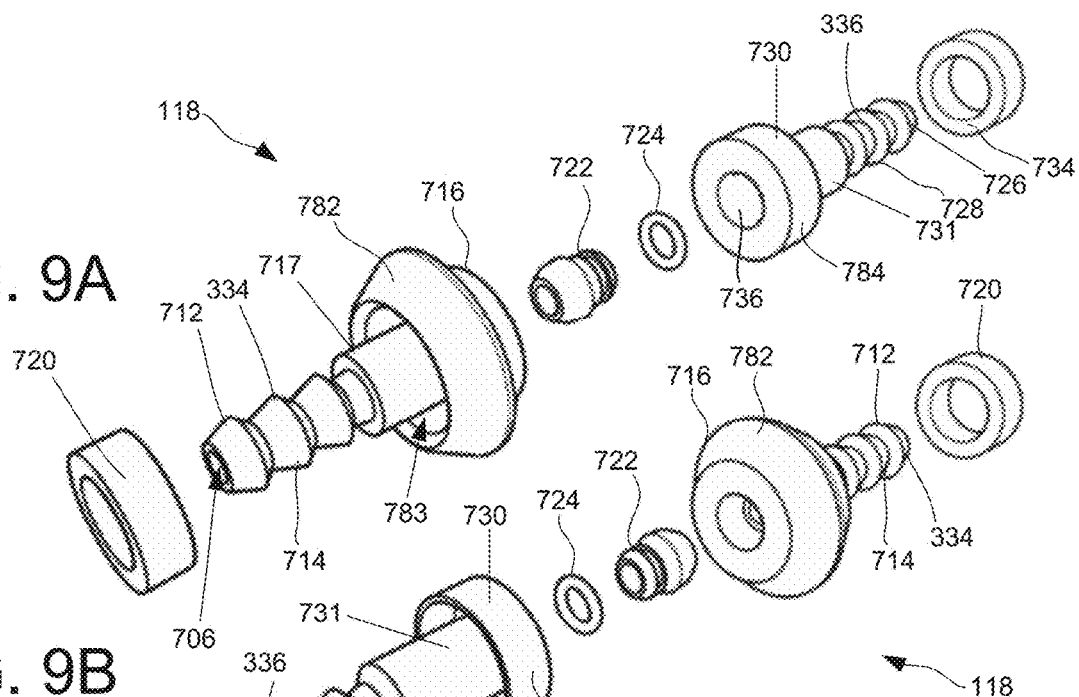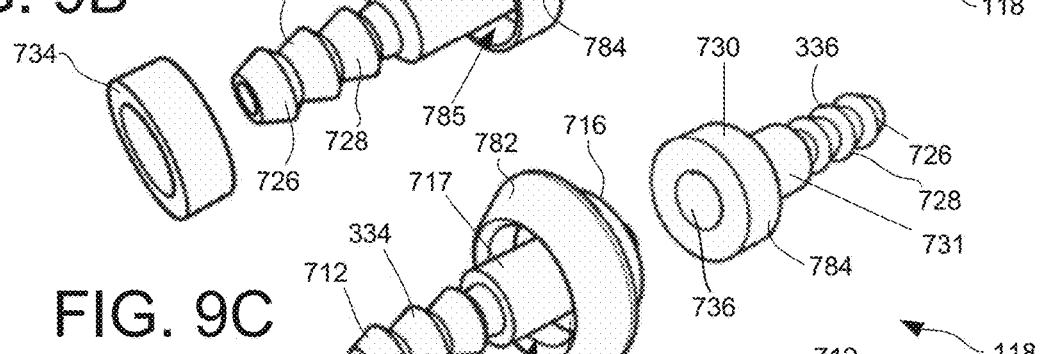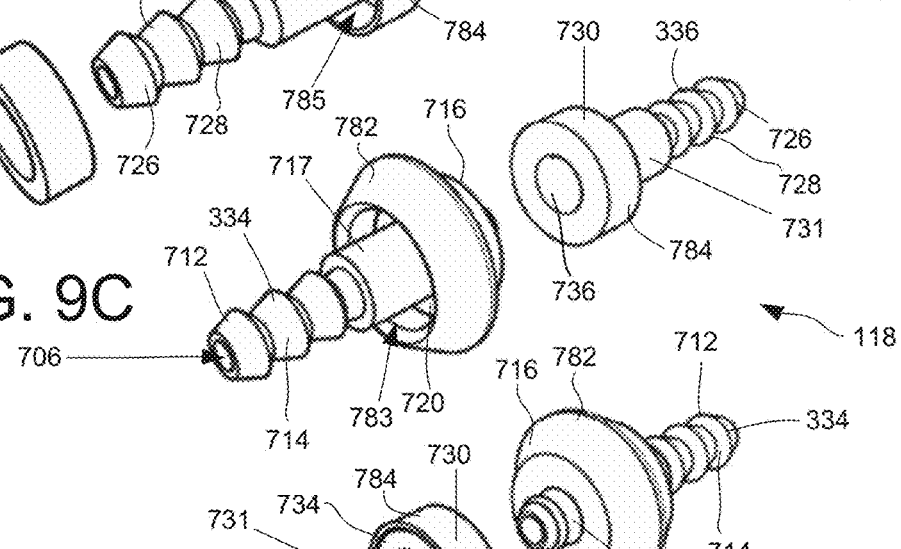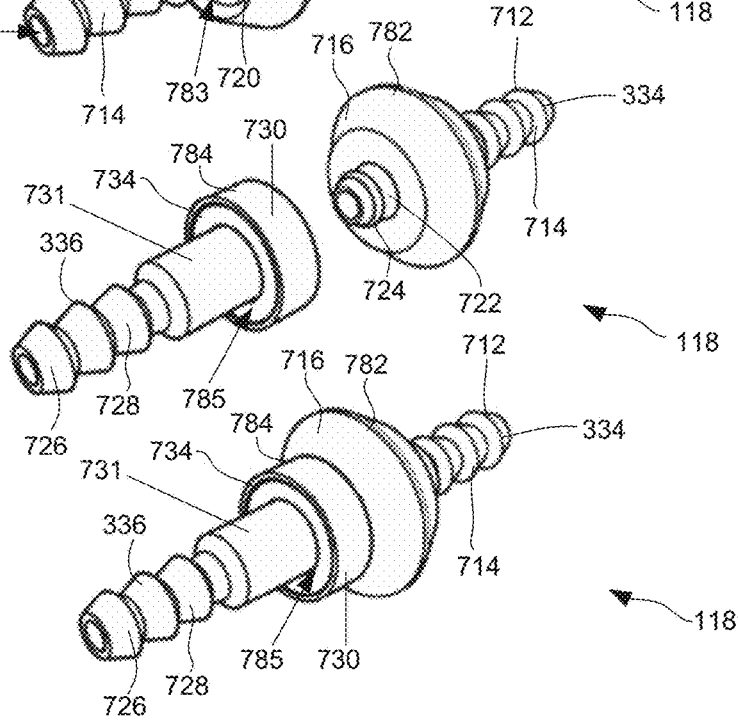

HYDRATION SYSTEM AND COMPONENTS THEREOF

CROSS-REFERENCE TO RELATED APPLICATIONS

This application is a continuation of U.S. application Ser. No. 15/653,439, filed Jul. 18, 2017, which in turn claims the benefit of U.S. Provisional Application No. 62/423,756, filed Nov. 17, 2016, and the benefit of U.S. Provisional Application No. 62/363,334, filed Jul. 18, 2016. All of the foregoing applications are incorporated herein by reference as if fully set forth herein.

This application is related to U.S. application Ser. No. 15/652,847 filed Jul. 18, 2017, which is hereby incorporated by reference.

This application is also related to the application entitled HYDRATION AND AUDIO SYSTEM that was filed on Nov. 17, 2016, and assigned U.S. Provisional Application No. 62/423,415, the disclosure of which is incorporated herein by reference as if fully set forth herein.

This application is also related the application entitled HYDRATION AND AIR COOLING SYSTEM that was filed on Nov. 17, 2016, and assigned U.S. Provisional Application No. 62/423,430, the disclosure of which is incorporated herein by reference as if fully set forth herein.

FIELD

The present patent document relates generally to magnetic connectors for fluid delivery systems and methods of using such connectors. The present patent document also relates to hydration systems and various components of hydration systems.

BACKGROUND

Medical research has demonstrated the importance of maintaining adequate hydration to maintain a person's physical and mental health. Serious consequences can occur due to the lack of proper hydration. These consequences can range in severity from fatigue and nausea to loss of consciousness and even death. To maintain optimum health, physicians generally recommend that under normal conditions individuals drink at least eight 8 ounce (240 ml) glasses of water a day (for a total of a gallon of water per day). When an individual is under physical exertion, exposed to extreme environmental conditions, and/or over weight, the amount of fluids that the individual needs to consume generally increases because the individual's rate of fluid loss increases under such circumstances. Thus, regardless of whether a person is exercising, working, or simply resting, maintaining proper hydration and peak performance (both physical and mental) requires the regular ingestion of fluids, which in turn requires the availability of fluids to ingest.

Various portable devices have been developed to help address the availability problem. These devices have included, for example, aluminum canteens and plastic water bottles. While these devices are reasonably light, durable and inexpensive, they do not allow hands-free fluid consumption, which may be desirable or even extremely important in some applications. In addition, they are often awkwardly mounted to a waist belt or in a pocket of a backpack, making the process of accessing them during certain activities impractical and even unsafe. As a result, individuals using these types of portable devices often go without fluids longer than they should. Frequently, this is because the user has to wait for a suitable break in their activity before safely reaching for the water bottle or canteen. Because of the inconvenience and/or safety issues, individuals using these types of devices also often wait until they feel thirsty before finding a suitable break in whatever activity they are engaged to have a drink. The problem with this approach, however, is that by the time a person is thirsty, they are already dehydrated and thus their body is no longer at optimal performance. In addition, if an individual waits too long to properly hydrate, their body can begin to cramp, causing pain and a further reduction in the individual's ability to engage in physical activity. Moreover, the recovery from dehydration does not take place simply with an individual's over drinking of water. This is because the cells of the human body begin to shut down once the human body becomes dehydrated, and it is only through a slow process of re-hydration that the cells of the body can recover and begin to function properly again.

More recently, personal hydration systems have been developed that offer a number of advantages over water bottles and canteens, including improved fluid delivery capabilities and convenience. These systems frequently include either a semi-rigid or flexible bag-like fluid reservoir that may be carried in a pack on the user's back or waist. These systems permit a user to drink more frequently while engaged in a variety of sporting, recreational, and work related activities because a long flexible drink tube is connected to the reservoir through an exit port at one end and terminates in a mouthpiece with a bite valve at the other end. The tube is long enough to allow the mouthpiece to be carried in the user's mouth to enable the user to draw water from the reservoir at will. Examples of personal hydration systems of this type and mouthpieces therefor are disclosed in U.S. Pat. Nos. 5,727,714, 5,060,833, 5,085,349, 6,070,767, and 7,490,740.

Although personal hydration systems have generally provided a significant advance over traditional water bottles, they continue to suffer from a number of shortcomings. One shortcoming, for example, has been that the components of the hydration system downstream from the fluid reservoir have historically been either permanently secured together or secured together via a tight friction fit that tends to be difficult to establish or release. Although these types of connection structures provide suitable fluid-tight seals, they are not optimal in terms of both providing a fluid-tight seal and permitting components downstream of the reservoir to be quickly and repeatedly interchanged by a user. Moreover, these structures are not designed to permit downstream components to be easily and safely disconnected in the event of an emergency or in the event of something snagging one of the downstream components.

Mechanical quick connects, such as those described in U.S. Pat. No. 7,073,688, have been employed to allow downstream components in a personal hydration system to be quickly and repeatedly connected and disconnected. Mechanical quick connects also allow a user to quickly and easily interchange downstream components. As a result, mechanical quick connects are quite useful in many applications. One drawback of mechanical quick connects, however, is that once they are connected they can only be disconnected by pressing a release button. This can pose a significant safety problem in a number of sporting and work related activities. Furthermore, depending on the location of the mechanical quick connect in the fluid delivery system, two hands may actually be required to connect and/or disconnect the male and female members of the quick connect provided on the mating components of the hydration system. And certainly mechanical quick connects are not designed to permit users to attach or detach components with a single hand, or without the benefit of the user visualizing the male and female members of mechanical quick connect that are to be connected or disconnected.

Another shortcoming in these conventional systems is that the drink tube is left dangling. As a result, when the user releases the mouthpiece located on the terminal end of the of the drink tube from the user's mouth, the tube will fall away from the user's mouth and require the user to retrieve the drink tube and put the mouthpiece back in his or her mouth the next time another drink is desired. However, it may not be practical (or even safe) for a user to manipulate the drink tube in this manner during certain activities, for example when the user is traveling at a high rate of speed, such as on a bicycle, in a race car or on a motorcycle. Yet, it is also not always practical, or even desirable, for the user to keep the mouthpiece in his or her mouth at all times.

Headgear has been developed to facilitate hands-free hydration. The headgear is designed to permit the bite-valve of the drink tube to be adjustably located in front of the user's mouth. A variety of different types of headgear of this type are described in U.S. Pat. No. 6,283,344 to Bradley, which is hereby incorporated by reference. The various types of headgear described in the Bradley patent are all designed to be worn on the user's head such that an intermediate portion of the drink tube is located vertically above the user's mouth. The configuration employed in the Bradley patent is designed so that when the user is riding a bicycle or the like, fluids can be provided from a back mounted hydration pack to the user via gravity or a siphon, thereby reducing the amount the user has to suck on the bite valve, which is located on the terminal end of the drink tube, to draw fluids from the hydration reservoir to the user's mouth. All of the connectors used in the headgear described in Bradley, however, are of the friction fit variety. As a result, the portion of the drink tube that extends from the headgear to the fluid reservoir are subject to being snagged by objects in the environment in which the user is performing his or her activity. For example, a tree limb could snag the drink tube as a bicyclist is riding past a tree. If the drink tube is snagged in this manner, the headgear can potentially be ripped from the user's head and/or the user can be injured.

Another shortcoming of personal hydration systems has been providing a reservoir that can be readily accessed by the user for cleaning. To address this problem, hydration bags have been developed that include an opening defined by generally opposed ribs that are sealed by compressing the ribs together, similar to how a ZIPLOCK™ brand storage bag is sealed. Another solution to this problem has been the use of a roll top, or folded top, which is closed by rolling or folding the top, much like a dry bag used in camping. Another proposed solution to this problem is described in U.S. Pat. No. 6,820,780, in which a personal hydration system is described that includes a hydration bag with a relatively large diameter fill port and mating cap. One disadvantage of each of these approaches is that because the hydration bags are extremely flexible, it is often awkward or difficult for a user to fill the hydration bag without spilling fluids. It is also difficult for the user to fill the bags to their maximum capacity. Further, to fill a hydration bag, the bag must be removed from its pack, and once filled the bag must then be stuffed back in the pack, which can be challenging.

Another shortcoming of the personal hydration systems of the type described above is that the user has to suck water up the lengthy drink tube. The process is much like drinking through a straw. The user bites on the bite-valve included in the mouthpiece and then sucks on the mouthpiece to draw water or other fluid from the fluid reservoir into the user's mouth. The rate at which fluid from the reservoir is delivered to the user will depend on the amount of suction, as well as the amount of resistance to fluid flow within the system. And while the process is fairly straight-forward and simple, in certain situations it can be taxing for the user. This can occur, for example, when the user is already exerting significant energy and breathing hard due to exercise or where the user is perhaps more elderly and/or frail. This is because these systems also require the user to hold their breath while they suck fluids from the reservoir to drink, which is not always practical, such as when the user is already breathing hard and short of breath.

Hydration systems have been provided with powered pumps or pressurizing mechanisms so that a user does not have to suck fluids from the reservoir or hold their breath while drinking. Hydration systems provided with these features have thus far still suffered from many of the other drawbacks discussed above. In addition, pump housings have not been designed to readily connect and disconnect to the outlet ports of the hydration bags. This can, for example, make it difficult to connect and disconnect the pump at will from the hydration bag. This can also result in the weight of the pump, power source, and housing being distributed in a manner that may not be ideal.

The actuation switch in systems including a pump also have room for improvement. For example, the actuation switch in some of these systems has been located on the fluid delivery tube itself, which requires a user to reach his hand to the tube to actually activate the pump. Depending on activity in which the user is engaged, this may or may not be practical. Actuation switches have also been located on handlebars of a bicycle, but this approach has required the user to remove one of his or her hands from the handlebar grips to activate the switch, which, depending on the conditions of the bike path and speed of the bike, may not be safe. U.S. Patent Publication 2004/0045980 A1 to Duncan Robins describes a personal hydration system in which a mouth activated switch is provided in the mouthpiece of the drink tube. The design described in the Robins publication, however, requires the user to keep the mouthpiece in his or her mouth during use, which is not always practical or even desirable during many activities. Alternatively, as with known suction-type (or pump-less) hydration systems discussed above, the user can allow the drink tube to dangle free between drinks and then grab the drink tube and place the mouthpiece in his or her mouth when a drink is desired. But, just as with conventional suction-type hydration systems, it may not always be practical (or even safe) for a user to manipulate the drink tube in this manner.

Further, as the use of liquids with dissolved salts and/or sugars increases in hydration systems (both pumped and pump-less), the cleanliness of hydration systems and their component parts will become a greater concern to users. This is because the use of sugars in a hydration system can lead to contamination due to trapped residue and/or accumulation of bacteria, particularly in the area of a bite-valve, mouthpiece, and/or pump. Thus, hydration systems and/or components thereof that are readily cleanable are desirable.

SUMMARY

The present patent disclosure discloses a number of inventions related to hydration systems, various components thereof, magnetic connectors for fluid delivery systems, and methods of using the foregoing. Some of the disclosed inventions are summarized below.

Hydration System

One object of the present patent disclosure is to disclose a hydration system, as well as components of a hydration system, that address, or at least ameliorate, one or more of the problems associated with the hydration systems discussed above. To this end, in one aspect of the present patent document, a hydration system comprising a portable fluid reservoir, a fluid path in communication with the reservoir, and a magnetic quick connect interposed in the fluid path is provided.

In one embodiment, the fluid path is a fluid delivery path for delivering fluid from the portable fluid reservoir to a user's mouth. In some embodiments, the hydration system may further comprise a headset and the distal end of the fluid delivery path may be included in the headset. Preferably the headset includes a support structure that is configured to support the headset on headgear adapted to be worn on a user's head. For example, the support structure may be configured to attach to headgear and support the headset on the headgear once attached, or it may already be attached to the headgear, or, in still further embodiments, at least a portion of the support structure may be formed integral with the headgear.

The support structure may, for example, comprise a mounting bracket.

In some embodiments, the headgear may comprise safety headgear, such as a helmet or hard hat. In other embodiments, the headgear may comprise other common headgear such as, for example, a hat, head bracket, or any other garment or device intended to be worn on a person's head. When the applicable headgear is safety headgear, the support structure may be configured to attach to the safety headgear, it may already be attached to the safety headgear, or at least a portion of the support structure may be formed integral with the safety headgear. Further, the headset of the hydration system may be attached to, or integrated with, any type of helmet, including, for example, motorcycle helmets (half, three quarter, open face, and full face), auto racing helmets, cycling helmets, snowboarding and skiing helmets, mountain climbing helmets, military and other tactical helmets, fire helmets, safety helmets, and rescue helmets.

In certain embodiments, the proximal end of the headset comprises the magnetic quick connect. Preferably, the fluid delivery path between the portable fluid reservoir and the magnetic quick connect comprises a hose that is configured so that when a user is wearing headgear to which the headset is attached turns his or her head it does not cause the magnetic quick connect to disconnect. This may be accomplished by using a hose with a suitable length, wall thickness, outer diameter, and/or Shore Durometer hardness. Preferably the hose has a Shore Durometer hardness in the range of about 50 A to 70 A on the Shore A scale. Further, the hose is preferably food grade, more preferably food grade polyvinylchloride.

In some embodiments, the hydration system may comprise a personal hydration system designed to be carried by a user. The hydration system may also comprise a pump interposed in the fluid path between the reservoir and the magnetic quick connect.

In some embodiments, the fluid path may comprise a fluid delivery path that is in fluid communication with a second fluid reservoir. In such embodiments, a refill button operably connected to the pump can be used to refill the portable fluid reservoir with fluids from the second fluid reservoir. Preferably the second fluid reservoir is larger than the portable fluid reservoir.

The magnetic quick connect included in the hydration system will typically comprise a male coupling member and a female coupling member. Preferably the coupling members are configured so that an axial pull force between the male coupling member and female coupling member that is greater than 48 ounce-force and less than 128 ounce-force is required to decouple the coupling members in the axial direction.

Preferably the male coupling member and female coupling member are configured so that they may also be decoupled by pivoting one coupling member relative to the other coupling member through the application of a torque. In one embodiment, a torque in the range of about 16 ounce-inches to about 72 ounce-inches is required to pivot the pivoted coupling member. Preferably the pivoted coupling member comprises a lever arm of greater than or equal to about 1.0 inches and less than or equal to about 2 inches from the pivot point.

Fluid Delivery System

In another aspect, a fluid delivery system for a hydration system is provided. According to one embodiment, the fluid delivery system comprises a fluid delivery path having a proximal end adapted to be attached to a fluid reservoir so as to establish fluid communication between the fluid delivery path and the fluid reservoir, and a magnetic quick connect interposed in the fluid delivery path.

In some embodiments, the fluid delivery path further comprises a connector at the proximal end of the fluid delivery path for connecting the fluid delivery path to a fluid reservoir. The connector is preferably a male or female member of a mechanical quick connect.

Preferably the fluid delivery path is for delivering fluid from a portable fluid reservoir to a user's mouth. Further, in some embodiments, a distal end of the fluid delivery path may be included in a headset. Preferably the headset includes a support structure that is configured to support the headset on a headgear adapted to be worn on a user's head. For example, the support structure may be configured to attach to headgear that is adapted to be worn on a user's head and support the headset on the headgear once attached, or it may already be attached to a headgear, or, in still further embodiments, at least a portion of the support structure may be formed integral with the headgear.

The support structure may, for example, comprise a mounting bracket.

In some embodiments, the headgear may comprise safety headgear, such as a helmet or hard hat. In other embodiments, the headgear may comprise other common headgear such as, for example, a hat, head bracket, or any other garment or device intended to be worn on a person's head. When the applicable headgear is safety headgear, the support structure may be configured to attach to the safety headgear, it may already be attached to the safety headgear, or at least a portion of the support structure may be formed integral with the safety headgear. Further, the headset of the fluid delivery system may be mounted to, or integrated with, any type of helmet, including, for example, motorcycle helmets (half, three quarter, open face, and full face), auto racing helmets, cycling helmets, snowboarding and skiing helmets, mountain climbing helmets, military and other tactical helmets, fire helmets, safety helmets, and rescue helmets.

In some embodiments, the proximal end of the headset comprises the magnetic quick connect. The magnetic quick connect preferably comprises a male coupling member and a female coupling member. In some embodiments that include a headset with a support structure, the support structure is further configured to support the headset on the headgear so that when the headgear is worn on a user's head, at least a portion of the magnetic quick connect is disposed behind the user's ear. Preferably, at least the upstream coupling member is disposed behind the user's ear, but in some embodiments the entire magnetic quick connect may be disposed behind the user's ear.

The portion of the fluid delivery path that extends between the proximal end of the fluid delivery path and an upstream end of the magnetic quick connect may comprise a hose in some embodiments. Preferably, the hose is configured so that when the proximal end of the hose is connected (directly or indirectly) to a fluid reservoir and a user is wearing the headset or when a user is wearing headgear to which the headset is mounted turns his or her head it does not cause the coupling members of the magnetic quick connect to uncouple from one another. This may be accomplished, for example, by using a hose with a suitable length, wall thickness, outer diameter, and/or Shore Durometer hardness. Preferably the hose has a Shore Durometer hardness in the range of about 50 A to 70 A on the Shore A scale. Further, the hose is preferably food grade, more preferably food grade polyvinylchloride.

Preferably male and female coupling members are configured so that an axial pull force that is greater than 48 ounce-force and less than 128 ounce-force between the male coupling member and female coupling member is required to decouple the coupling members in the axial direction. In preferred embodiments, the male coupling member and female coupling member are also configured so that they may be decoupled by pivoting one coupling member relative to the other coupling member through the application of a torque. In some embodiments, a torque in the range of about 16 ounce-inches to 72 ounce-inches is required to be applied to the pivoted coupling member to decouple it from the other coupling member. To facilitate uncoupling, the pivoted coupling member may comprise a lever arm of greater than or equal to about 1.0 inches and less than or equal to about 2 inches from the pivot point.

In some embodiments a pump is interposed in the fluid delivery path between a mechanical connector at the proximal end of the fluid delivery path and the magnetic quick connect. Preferably the mechanical connector is a male or female member of a mechanical quick connect and is configured to couple with a mating member provided on a portable fluid reservoir. The male or female member of the mechanical quick connect may be mounted in a pump housing disposed around the pump and the connector. Preferably the housing is shaped such that the mounted male or female member can still be coupled with, and decoupled from, a mating member of the mechanical quick connect.

Magnetic Quick Connect

An object of another aspect of the present patent disclosure is to provide a magnetic quick connect for a fluid delivery system. The magnetic quick connect may be used in a wide variety of fluid delivery systems, including, but not limited to, the fluid delivery system of a hydration system. When used in a fluid delivery system of a hydration system, the magnetic quick connect beneficially addresses, or at least ameliorates, one or more of the problems associated with the personal hydration systems discussed above.

A magnetic quick connect according to one embodiment of the present aspect comprises a male coupling member and a female coupling member. The male coupling member comprises a first end, a second mating end, a first fluid communication path extending from the first end to the second mating end of the male coupling member, and a first magnetic material disposed about the fluid communication path in the male coupling member proximate the second mating end. Similarly, the female coupling member comprises a first end, a second mating end, the second mating end having an outer cross-sectional profile, a second fluid communication path extending from the first end to the second mating end of the female coupling member, and a second magnetic material disposed about the fluid communication path in the female coupling member proximate the second mating end.

The second mating end of the male coupling member includes a protrusion having a cross-sectional profile that is dimensioned to fit within the outer cross-sectional profile of the second mating end of the female coupling member. Further, a portion of the first fluid communication path extends through the protrusion, an O-ring is disposed about the protrusion, and the second mating end of the female coupling member includes a protrusion mating surface shaped so as to define a protrusion receiving area within the second mating end of the female coupling member so that when the male and female coupling members are coupled together, the protrusion extends into the protrusion receiving area, the first fluid communication path and second communication path are axially aligned and in fluid communication, and the O-ring is compressed between the protrusion and protrusion mating surface. Further, the first and second magnetic materials are disposed proximate the second mating end of their respective coupling members so that when the male and female coupling members are coupled together, they are detachably held together by an attractive force between the first and second magnetic materials.

The magnetic quick connects of the present patent document may be used in gas and/or liquid delivery or communication systems to connect two fluid conduits together in fluid communication with one another. The O-ring preferably forms a fluid-tight seal between the protrusion and the protrusion mating surface when the male and female coupling members are coupled together. In liquid delivery systems, this means the O-ring preferably forms a liquid-tight seal between the protrusion and the protrusion mating surface when the male and female coupling members are coupled together. In gas delivery systems, the O-ring preferably forms a gas-tight seal between the protrusion and the protrusion mating surface when the male and female coupling members are coupled together.

In some embodiments, at least one of the first magnetic material and the second magnetic material comprises a permanent magnet. Preferably each of the first magnetic material and the second magnetic material comprise a material selected from the group consisting of a ferromagnetic material and ferrimagnetic material.

The male and female coupling members (including the placement, size, and magnetic strength of the first and second magnetic materials) are preferably configured so that an axial pull force that is greater than or equal to about 48 ounce-force and less than or equal to about 128 ounce-force between the male coupling member and female coupling member is required to decouple the coupling members in the axial direction. More preferably, the male and female coupling members are configured so that an axial pull force that is greater than or equal to about 64 ounce-force and less than or equal to about 96 ounce-force, and even more preferably greater than or equal to about 72 ounce-force and less than or equal to about 88 ounce-force, between the male coupling member and female coupling member is required to decouple the coupling members in the axial direction.

In some embodiments, the protrusion comprises a body of revolution. In some embodiments, the protrusion and protrusion receiving area may be tapered. The angle of taper is preferably in the range of 15° to 50° from the axis of the protrusion, more preferably, in the range of 20° to 40°, and even more preferably 25° to 35°. Tapering the protrusion and protrusion receiving area in this manner, helps the male and female coupling members to be self-centering with respect to one another. It also allows the quality of the seal between the O-ring and the protrusion receiving surface to be increased.

The protrusion and protrusion receiving area are preferably sized so that the male coupling member and female coupling member may be decoupled by pivoting one coupling member relative to the other coupling member through the application of a torque to the pivoted coupling member. In some embodiments, the distance that the protrusion extends into the protrusion receiving area is less than the minimum diameter of the protrusion receiving area that receives the protrusion.

Preferably, the coupling members are configured so that the torque required to decouple the coupling members is in the range of about 16 ounce-inches to about 72 ounce-inches, more preferably in the range of about 35 ounce-inches to about 64 ounce-inches, and yet even more preferably in the range of about 48 ounce-inches to about 60 ounce-inches. The pivoted coupling member may comprise a lever arm of greater than or equal to about 1.0 inches and less than or equal to about 2 inches, and more preferably greater than or equal to about 1.5 inches and less than or equal to about 2 inches, from the pivot point in order to facilitate the application of a suitable torque to decouple the coupling members.

In certain embodiments, the male coupling member further comprises a first collar disposed at the second mating end of the male coupling member, and the female coupling member further comprises a second collar disposed at the second mating end of the female coupling member. In such embodiments, the first collar preferably defines at least part of a surface of the male coupling member that abuts the female coupling member when the male and female coupling members are coupled together, and the second collar preferably defines at least part of a surface of the female coupling member that abuts the male coupling member when the male and female coupling members are coupled together. Preferably the first magnetic material is disposed within the first collar and the second magnetic material is disposed within the second collar. Further, the first magnetic material and second magnetic material may be ring-shaped. In such embodiments, the first fluid communication path can be configured to extend coaxially through the first magnetic material and the protrusion, and the second fluid communication path can be configured to extend coaxially through the second magnetic material.

The first magnetic material may be disposed within an annular channel defined by the first collar, and the second magnetic material may be disposed within an annular channel defined by the second collar. Further, at least one of the first collar and second collar may define an annular channel that is open away from the abutting surfaces of the first and second collars.

In some embodiments, the first end of at least one of the male coupling member and female coupling member further comprises a hose connector, such as a barbed hose connector, to facilitate connection of the magnetic quick connect to a hose, such as a drink tube of a personal hydration system. Further, the magnetic quick connect may also comprise a removable hose collar including a tubular receiving hole sized to receive the hose connector and a hose therethrough when the hose connector is connected to a hose. In some embodiments, the annular channel is included in the coupling member that comprises the hose collar, and the hose collar includes an annular extension at one end sized to be inserted within the annular channel. Moreover, the annular extension may be sized to provide an interference fit with the annular channel.

In some embodiments, the first collar comprises a body of revolution having a first diameter at the surface of the male coupling member that abuts the female coupling member and a second diameter that is greater than the first diameter at a first location rearward of the abutting surface. The first collar may further comprise a third diameter at a second location rearward of the first location, where the third diameter is greater than the first diameter, but less than the second diameter. Moreover, the diameter of the collar may transition smoothly from the first diameter to the second diameter and from the second diameter to the third diameter.

Kit for Forming a Fluid Delivery System

In another aspect of the present patent document, a kit for forming a fluid delivery system for a hydration system is provided. In one embodiment, the kit comprises a magnetic quick connect comprising a male coupling member and a female coupling member. At least one of the male and female coupling members have a mechanical connector designed to connect to a drink tube of a hydration system. The kit may further include instructions describing how to interpose the magnetic quick connect in a fluid path that is in communication with a reservoir of a hydration system. In some embodiments, the mechanical connector comprises a barbed hose connector.

The kit may also include a drink tube having a distal end sized to connect to the hose connector, such as a barbed hose connector. In addition, the kit may include a pump housing that includes within the housing a fluid path extending from an inlet port to an outlet port and a pump interposed in the fluid path between the inlet and outlet ports, where the inlet and outlet ports are both accessible from the outside of the housing. In one embodiment, a first coupling member of a mechanical quick connect is disposed at a distal end of the pump housing, a second coupling member of a mechanical quick connect is disposed at a proximal end of the pump housing, a fluid path extends between the first coupling member and second coupling member within the housing, and a pump is enclosed within the pump housing and interposed in the fluid path. Further, a third coupling member may be disposed at a proximal end of the drink tube for connecting to the first coupling member and establishing fluid communication between the fluid path extending between the first and second coupling members and the drink tube. Moreover, the housing is preferably shaped such that the second coupling member can be coupled with, and decoupled from, a mating coupling member provided on a portable hydration reservoir.

In some embodiments, the kit may also include a headset. Preferably the proximal end of the headset comprises the magnetic quick connect, and the upstream coupling member of the magnetic quick connect comprises the connector designed to connect to the distal end of the drink tube. In addition, in some embodiments, the headset may further include a support structure that is configured to support the headset on headgear adapted to be worn on a user's head. For example, the support structure may be configured to attach to headgear that is adapted to be worn on a user's head and support the headset on the headgear once attached, or it may already be attached to the headgear. Further, in some embodiments, at least a portion of the support structure may be formed integral with the headgear.

The support structure may, for example, comprise a mounting bracket.

In some embodiments, the headgear may comprise safety headgear, such as a helmet or hard hat. In other embodiments, the headgear may comprise other common headgear such as, for example, a hat, head bracket, or any other garment or device intended to be worn on a person's head. When the applicable headgear is safety headgear, the support structure may be configured to attach to the safety headgear, it may already be attached to the safety headgear, or at least a portion of the support structure may be formed integral with the safety headgear. Further, the headset included in a kit of the present patent document may be mounted to, or integrated with, any type of helmet, including, for example, motorcycle helmets (half, three quarter, open face, and full face), auto racing helmets, cycling helmets, snowboarding and skiing helmets, mountain climbing helmets, military and other tactical helmets, fire helmets, safety helmets, and rescue helmets.

Preferably the drink tube is configured so that when (i) the third coupling member is coupled to the first coupling member. (ii) the second coupling member is coupled to a mating coupling member of a fluid reservoir. (iii) the distal end of the drink tube is connected to the hose connector, and (iv) a user is wearing headgear on which the headset is supported turns his or her head, the coupling members of the magnetic quick connect do not uncouple from one another. This may be accomplished, for example, by using a hose with a suitable length, wall thickness, outer diameter, and/or Shore Durometer hardness. Preferably the drink tube has a Shore Durometer hardness in the range of about 50 A to 70 A on the Shore A scale.

In some embodiments of the kit, the male and female coupling members are configured so that an axial pull force that is greater than or equal to about 48 ounce-force and less than or equal to about 128 ounce-force between the male coupling member and female coupling member is required to decouple the them in the axial direction. The male coupling member and female coupling member may also be configured so that they may be decoupled by pivoting one coupling member relative to the other coupling member through the application of a torque to the pivoted coupling member. Preferably the torque required to decouple the coupling members is in the range of about 16 ounce-inches to about 72 ounce-inches. Preferably, the pivoted coupling member comprises a lever arm of greater than or equal to about 1.0 inches and less than or equal to about 2 inches from the pivot point to facilitate the application of the torque.

Headset for Use in a Hydration System

In another aspect of the present patent document, a headset for use in a hydration system including a fluid reservoir and an extended length of a drink tube that is in fluid communication with the fluid reservoir at a proximal end is provided. According to one embodiment, the headset comprises a fluid conduit having a fluid inlet port at one end and a fluid outlet port at a second end. The fluid inlet port may comprise a connector, such as a barbed hose connector, adapted to permit the fluid conduit to be detachably connected to a distal end of a drink tube of a hydration system so that the fluid conduit is in fluid communication with the drink tube. The headset further comprises a first magnetic quick connect comprising a male member and a female member, the first magnetic quick connect defining a portion of the fluid conduit. The headset also includes a support structure configured to support the first magnetic quick connect and at least a portion of the fluid conduit on headgear adapted to be worn on a user's head. For example, the support structure may be configured to attached to a headgear that is adapted to be worn on a user's head and support the headset on the headgear once attached, or it may already be attached to the headgear, or, in still further embodiments, at least a portion of the support structure may be formed integral with the headgear.

The support structure may, for example, comprise a mounting bracket.

In some embodiments, the headgear may comprise safety headgear, such as a helmet or hard hat. In other embodiments, the headgear may comprise other common headgear such as, for example, a hat, head bracket, or any other garment or device intended to be worn on a person's head. When the applicable headgear is safety headgear, the support structure may be configured to attach to the safety headgear, it may already be attached to the safety headgear, or at least a portion of the support structure may be formed integral with the safety headgear. Further, a headset of the present patent document may be attached to, or integrated with, any type of helmet, including, for example, motorcycle helmets (half, three quarter, open face, and full face), auto racing helmets, cycling helmets, snowboarding and skiing helmets, mountain climbing helmets, military and other tactical helmets, fire helmets, safety helmets, and rescue helmets.

The support structure may be further configured to support the headset on the headgear so that when the headgear is worn on a user's head, at least a portion of the magnetic quick connect is disposed behind the user's ear. Preferably, at least the upstream coupling member is disposed behind the user's ear, but in some embodiments the entire magnetic quick connect may be disposed behind the user's ear. Thus, for example, in embodiments where the support structure is configured to attach to headgear, such as a hat or helmet, the support structure may be configured to attach to the headgear so that when the headset is attached to the headgear and the headgear is worn on a user's head, the first magnetic quick connect is at least partially disposed behind the user's ear.

In some embodiments of the headset, the upstream member of the first magnetic quick connect includes the fluid inlet port. Further, the fluid inlet port may comprise a hose connector, such as a barbed hose connector, formed in the upstream member of the first magnetic quick connect.

Some embodiments of the headset further comprise a second magnetic quick connect defining a portion of the fluid conduit downstream of the first magnetic quick connect. The second magnetic quick connect also comprises a male member and a female member.

The headset may further comprise a detachable mouthpiece assembly. Preferably, a first end of the detachable mouthpiece assembly comprises the downstream member of the second magnetic quick connect, and the fluid outlet port is provided at a second end of the detachable mouthpiece assembly. Further, the fluid outlet port may be provided in a detachable mouthpiece of the mouthpiece assembly. The detachable mouthpiece may, for example, comprise a bite-valve or a nozzle provided at the second end to the detachable mouthpiece assembly.

Some embodiments of the headset may also include a valve interposed in the fluid conduit between the first magnetic quick connect and second magnetic quick connect. The valve, for example, may be a check valve, or one-way valve. In addition, a valve may be interposed in the fluid conduit between the inlet port and a downstream end of the upstream member of the first magnetic quick connect.

At least a portion of the fluid conduit may be configured to be adjustable to facilitate positioning of the fluid outlet port proximate the user's mouth.

In some embodiments, the headgear may comprise a head bracket mount, and the head bracket mount may be configured to include two opposing support members connected together by a resilient U-shaped spring member. When the two opposing support members are pulled away from one another, the U-shaped spring member produces a biasing force that tends to bias the opposing support members in a direction toward one another. Further, the head bracket mount is preferably configured so that when it is worn on a user's head the two opposing support members contact opposite sides of the user's head. In some embodiments, the head bracket mount is configured so that when it is worn on a user's head the two opposing support members contact opposite sides of the user's head and the U-shaped spring member wraps around the base of the user's skull. The headset may also further comprise a neck pad disposed about at least a middle portion of the U-shaped spring member.

The support structure is preferably configured so that when the head bracket is worn on a user's head at least the upstream member of the first magnetic quick connect is disposed behind the user's ear.

Further, at least a portion of the fluid conduit downstream of the first magnetic quick connect may comprise a flexible tube. Moreover, the headset may further comprise an adjustable frame about the flexible tube so as to permit the positioning of the fluid outlet port proximate the user's mouth. Preferably the fluid outlet port is a nozzle.

In certain embodiments including a detachable mouthpiece assembly, the mouthpiece assembly comprises a shaped conduit that is configured to extend below a chin guard of a full-face helmet and position the fluid outlet port so that it is proximate to and directed toward a user's mouth when the headset is mounted to a full-face helmet and the user is wearing the helmet.

In embodiments where the detachable mouthpiece assembly includes a downstream member of the second magnetic quick connect, preferably the male and female members of the second magnetic quick connect are configured so that an axial pull force that is greater than or equal to about 32 ounce-force and less than or equal to about 54 ounce-force is required to decouple the male and female members of the second magnetic quick connect in the axial direction. The male and female members of the second magnetic quick connect are also preferably configured so that the male member and female member of the second magnetic quick connect may also be decoupled by pivoting the downstream member relative to the upstream member through the application of a torque to the detachable mouthpiece. Preferably the torque required to detach the detachable mouthpiece is in the range of about 20 ounce-inches to about 36 ounce-inches.

The male and female members of the first magnetic quick connect are preferably configured so that an axial pull force that is greater than 64 ounce-force and less than 96 ounce-force is required to decouple the male and female members of the first magnetic quick connect in the axial direction. The male member and female member of the first magnetic quick connect are also preferably configured so that they may be decoupled by pivoting one member relative to the other member through the application of a torque that is in the range of about 35 ounce-inches to 64 ounce-inches to the pivoted coupling member. To facilitate application of the decoupling torque, the pivoted member of the first magnetic quick connect comprises a lever arm of greater than or equal to about 1.0 inches and less than or equal to about 2 inches from the pivot point.

In some embodiments in which the support structure comprises a helmet mount, the helmet mount is preferably elongated in one direction and shaped to generally match the curvature of a helmet so that in a top view of the helmet mount, the centerline of the helmet mount curves inwardly from a proximal end of the helmet mount to a distal end of the helmet mount. The helmet mount is also preferably configured to hold the downstream member of the first magnetic quick connect at the proximal end of the helmet mount and the upstream member of the second magnetic quick connect at the distal end of the helmet mount. In such embodiments, a fluid conduit is provided that extends from an inlet of the upstream member of the first magnetic quick connect to the outlet of the downstream member of the second magnetic quick connect, and ultimately to the fluid outlet port of the headset.

In some embodiments, the support structure may further include at least one adhesive backed helmet pad. The at least one adhesive backed helmet pad may be configured to (i) adhesively attach to a helmet, and (ii) have the helmet mount attach thereto once the at least one helmet pad is attached to a helmet.

Detachable Mouthpiece Assembly

In another aspect of the present patent document, a detachable mouthpiece assembly is provided for a headset of a hydration system including a fluid reservoir and an extended length of a drink tube that is in fluid communication with the fluid reservoir at a proximal end of the drink tube and a fluid path extending through the headset at a distal end of the drink tube. In one embodiment, the detachable mouthpiece comprises a fluid conduit extending from an entrance port to an outlet port. A downstream coupling member of a magnetic quick connect defines the entrance port and at least a portion of the fluid conduit. The downstream coupling member is configured to couple with a mating upstream coupling member disposed at a distal end of the headset so that when coupled the fluid conduit will be in fluid communication with the fluid path. In some embodiments, the mating upstream coupling member will be disposed at a distal end of a helmet mount of the headset.

The detachable mouthpiece assembly may further comprise a detachable mouthpiece at the distal end of the fluid conduit. In such embodiments, the fluid outlet port is provided in the detachable mouthpiece. Further, the detachable mouthpiece may comprise a bite-valve or a nozzle. Preferably the detachable mouthpiece is adjustable so that the angle and/or height of the fluid outlet port can be adjusted relative to the downstream coupling member.

In certain embodiments, the downstream coupling member is a female coupling member.

Further, in some embodiments, the downstream coupling member includes an abutting surface with an indexing feature, and the abutting surface is configured to abut a surface of the mating upstream coupling member that has a matching indexing feature when the downstream coupling member and mating upstream coupling member are coupled together. The indexing feature provides a means of setting the amount of angular rotation of the downstream coupling member of the magnetic quick connect relative to the upstream coupling member. The indexing pattern may, for example, comprise a saw tooth pattern or a rectangular tooth pattern.

In some embodiments, the detachable mouthpiece assembly further comprises a shaped conduit defining at least a portion of the fluid conduit distal to the downstream coupling member. Further, the shaped conduit may be configured to (i) extend the fluid conduit below a chin guard of a full-face helmet when coupled to the mating upstream coupling member of a headset mounted to a full-face helmet, and (ii) position the fluid outlet port so that it is proximate to and directed toward a user's mouth when wearing the helmet.

Preferably, the downstream coupling member is configured so that when the downstream coupling member is coupled to a mating upstream coupling member, an axial pull force that is greater than 32 ounce-force and less than 54 ounce-force is required to decouple the coupling members in the axial direction. The downstream coupling member is also preferably configured so that the downstream coupling member and mating upstream coupling member may also be decoupled by pivoting the downstream coupling member relative to the mating upstream coupling member through the application of a torque to the detachable mouthpiece. The torque required to decouple the downstream coupling member from the upstream mating coupling member is preferably set in the range of about 20 ounce-inches to about 36 ounce-inches.

In some embodiments of the detachable mouthpiece assembly, the downstream coupling member comprises a female coupling member. Further, the female coupling member may comprise a first end, a second mating end having an outer cross-sectional profile, and a fluid communication path extending from the first end to the second mating end of the female coupling member. In addition, a magnetic material is preferably disposed about the fluid communication path in the female coupling member proximate the second mating end. The second mating end of the female connector may include a protrusion mating surface that defines a protrusion receiving area within the second mating end of the female coupling member. The protrusion mating surface may be shaped to match an outer surface of a protrusion on the mating upstream coupling member so that when the female coupling member and mating upstream coupling member are coupled together, the protrusion is received within the protrusion receiving area.

Further, the magnetic material may be disposed about the fluid communication path proximate the second mating end of the female coupling member so that when the female coupling member and mating coupling member are coupled together, they are detachably held together by an attractive force between the magnetic material and a mating magnetic material included in the mating coupling member.

The magnetic material may comprise, for example, a material selected from the group consisting of a ferromagnetic material and ferrimagnetic material. In some embodiments, the magnetic material comprises a permanent magnet.

In certain embodiments in which the downstream coupling member comprises a female coupling member, the female coupling member may include a collar disposed at the second mating end of the female coupling member. Moreover, the collar is preferably configured to define at least part of a surface of the coupling member that abuts the mating upstream coupling member when the coupling members are coupled together. In such embodiments, the magnetic material is preferably disposed within the collar, the magnetic material is preferably ring-shaped, and the collar preferably defines an annular channel that is open away from the abutting surface of the collars so that the magnetic material is disposed within the annular channel defined by the collar.

Preferably the downstream coupling member is configured so that when the downstream coupling member and upstream mating coupling member are coupled together a fluid-tight seal is formed between a protrusion and the protrusion mating surface.

Wireless Actuation System

In another aspect of the present patent document, a wireless actuation system is provided for use with a hydration system including a fluid reservoir, a wirelessly controlled pump in fluid communication with the reservoir, and an extended length of a drink tube that is in fluid communication with the fluid reservoir and pump at a proximal end and an exit port at a distal end. In one embodiment, the wireless actuation system comprises a microswitch, a first mounting means provided proximate the microswitch, and a wireless transmitter operably connected to the microswitch. For example, a cable may be electrically connected to the microswitch at one end and include an electrical connector at a second end that removably mates with a mating electrical connector included in the wireless transmitter.

The first mounting means may be configured to attach the microswitch to a portion of a steering mechanism of a vehicle that is controlled by a user's hand. The wireless actuation system also preferably comprises a second mounting means that is attached to the wireless transmitter for removably attaching the wireless transmitter to the steering mechanism of a vehicle, and the wireless transmitter is preferably configured to transmit a first signal when the connector is connected to the mating connector and the microswitch is closed. The first signal may, for example, be a command signal to instruct a wireless actuated pump to deliver a fluid, such as water, from a fluid reservoir. The vehicle may be any vehicle, including, for example, an airplane, ATC, ATV, bicycle, boat, car, helicopter, motorcycle, race car, sand rail, side-by-side, tank, and truck. Thus, the vehicle may, for example, be any wheeled vehicle (motorized or non-motorized), aircraft, spacecraft, or watercraft.

The first mounting means may be further configured in some embodiments to attach the microswitch on the steering mechanism in a location proximate to where a user's hand would grip the steering mechanism to steer the vehicle and the microswitch can be operated without the hand of the user being removed from the steering mechanism. For example, for a bicycle, the microswitch may be mounted on the handlebars adjacent the hand grips. On a motorcycle, the microswitch can be mounted on a clutch or brake lever so that it can be operated by the index finger of a rider's left or right hand, respectively. With respect to a car, truck, or race car, the microswitch may be mounted in a suitable location on the steering wheel or steering wheel hub so that it can be operated with an index finger or thumb of a user without the user removing his or her hand from the steering wheel. With respect to an airplane or helicopter, the microswitch may be provided on the joy stick of the plane or helicopter.

The first mounting means may comprise a pair of cable ties and an elongated piece of heat shrink tubing. For example, the heat shrink tubing may be disposed around the microswitch and a portion of the cable. A pair of slits may be provided in the shrink tubing on opposite sides of the microswitch so that each slit extends in an axial direction of the heat shrink tubing. Each cable tie is positioned to extend through one of slits.

The second mounting means may comprise a pair of straps in some embodiments. Each strap may be attached to opposite sides of the wireless transmitter at one end, and the other end of each of the straps may comprise a hook and a loop fastener, respectively.

Preferably, the wireless transmitter comprises a Blue Tooth transmitter. Further, the wireless transmitter may include an on/off switch and/or an indicator light, where the indicator light is configured to signal whether the first signal is being transmitted. In some embodiments, the wireless transmitter may be configured to transmit a second signal when the connector is connected to the mating connector and the microswitch is open. The second signal may, for example, be a command signal to instruct a wireless actuated pump to stop pumping, or delivering a fluid.

In some embodiments, the wireless transmitter has a single button, and when the wireless transmitter is configured to transmit the first signal when the single button is depressed and the second signal when the single button is not depressed and the microswitch is open (e.g., not depressed) when the connector is connected to the mating connector. Further, the wireless transmitter is preferably configured to transmit the second signal when the single button is not depressed, and when the connector is not connected to the mating connector.

In some embodiments, the wireless transmitter may have both a first button and a second button. When the connector is connected to the mating connector and the microswitch is open, the wireless transmitter is preferably configured to transmit a first signal when a first button is depressed, a second signal when neither the first or second buttons are depressed, and a third signal when the second button is depressed. The third signal may, for example, be a command signal to instruct a wireless actuated pump to pump in a reverse direction so as to deliver fluid from a refill reservoir to the portable fluid reservoir. Thus, the portable fluid reservoir can be filled (or refilled) in this manner. The wireless transmitter may be configured to transmit the same signals when the connector is disconnected from the mating connector.

In still another embodiment, the wireless transmitter may have a first button, a second button, and a third button. When the connector is connected to the mating connector and the microswitch is open, the wireless transmitter is preferably configured to transmit a first signal when a first button is depressed, a second signal when none of the first, second, or third button is depressed, a third signal when the second button is depressed, and a fourth signal when the third button is depressed. The fourth signal may, for example, be a command signal to instruct a wireless actuated pump to pause. For example, the wireless actuated pump may be configured to ignore (or not respond to) any signal received from the wireless transmitter until, for example, a resume command signal is received. The wireless transmitter may be configured to transmit the same signals when the connector is disconnected from the mating connector.

In some embodiments, the wireless transmitter includes a keychain loop to permit the transmitter to be suspended, for example, from a hydration backpack.

Vehicle Including a Personal Hydration System

In another aspect of the present patent document, a vehicle including a personal hydration system is provided. In one embodiment, the vehicle comprises a frame; a powertrain supported by the frame, and including a final drive mechanism; a hand operated steering mechanism supported by the frame; a fluid reservoir supported by the frame; a fluid communication path connected at a proximal end to the fluid reservoir and having an outlet port at its distal end, the fluid communication path having a length sufficient to extend from the reservoir to a location proximate a user's mouth; a pump interposed in the fluid communication path; a microswitch operably connected to the pump, the microswitch disposed on the steering mechanism in a location sufficiently proximate to where a user's hand would grip the steering mechanism to steer the vehicle so that the microswitch can be operated without a user removing his or her hand from the steering mechanism. A first signal instructing the pump to begin pumping may be communicated to the pump when the microswitch is closed (e.g., depressed), and a second signal instructing the pump to stop pumping may be communicated when the microswitch is open (e.g., not depressed). The pump may, for example, be electrically connected to the microswitch through a cable or wirelessly connected to the microswitch via a wireless transmitter. In some embodiments, the outlet port may be provided in a mouthpiece provided at the distal end of the fluid communication path. In other embodiments, various other suitable designs for the outlet port may be employed, including, for example, using the end of a drink tube as the outlet port.

With the foregoing arrangements, the operator of the vehicle may effortlessly remain hydrated without having to take his or her hand of the steering mechanism.

As a result, the above arrangement of a vehicle can provide important safety and/or performance benefits for the professionals involved in may sports and/or occupations, including, for example, the professional cyclist, the professional race car, truck, and/or motorcycle driver, as well professional pilots, such as military fighter and/or helicopter pilots, and tank drivers. Safety and/or performance benefits of the vehicle according to the present patent document, however, may also be realized by the avid enthusiast, as well as the casual vehicle operator.

The vehicle may be any vehicle, including, for example, an airplane, ATC, ATV, bicycle, boat, car, helicopter, motorcycle, race car, sand rail, side-by-side, tank, and truck. Thus, the vehicle may, for example, be any wheeled vehicle (motorized or non-motorized), aircraft, spacecraft, or watercraft.

The microswitch may be disposed in a variety of locations on the steering mechanism of the vehicle so that the microswitch can be operated without the hand of the user being removed from the steering mechanism. For example, for a bicycle, the microswitch may be disposed on the handlebars adjacent the hand grips so that it can be operated by a thumb or index finger of the user. On a motorcycle, for example, the microswitch can be disposed on a clutch or brake lever so that it can be operated by the index finger of a rider's left or right hand, respectively. With respect to a car, truck, or race car, the microswitch may be disposed in a suitable location on the steering wheel or steering wheel hub so that it can be operated with an index finger or thumb of a user without the user removing his or her hand from the steering wheel. With respect to an airplane or helicopter, the microswitch may be disposed on the joy stick of the plane or helicopter.

The vehicle may also include a first mounting means provided proximate the microswitch to mount the microswitch on the steering mechanism. Further, in embodiments where a wireless pump is employed, a wireless transmitter including a second mounting means attached thereto may be operably connected to the microswitch. For example, a cable may be electrically connected to the microswitch at one end and include an electrical connector at a second end that is adapted to removably mate with a mating electrical connector provided in the wireless transmitter. The second mounting means may be configured to removably attach the wireless transmitter to the steering mechanism of the vehicle. Further, the wireless transmitter may be configured to transmit the first signal when the connector is connected to the mating connector and the microswitch is closed and the second signal when the microswitch is open.

The first and second mounting means may comprise any suitable attachment mechanism, including one or more straps or a mounting bracket. In one embodiment, the first mounting means comprises a pair of cable ties and an elongated piece of heat shrink tubing. The heat shrink tubing is disposed around the microswitch and a portion of the cable and includes a pair of slits on opposite sides of the microswitch. Each slit extends in an axial direction of the heat shrink tubing and each cable tie extends through one of slits and encircles a portion of the steering mechanism. The second mounting means, in a preferred embodiment, comprises a pair of straps, each strap attached to opposite sides of the wireless transmitter at one end, and the other end of each of the straps comprises a hook and a loop fastener, respectively.

The wireless transmitter preferably comprises a Blue Tooth transmitter and/or an on/off switch. The wireless transmitter may also have an indicator light, and the indicator light may be configured to signal whether the first signal is being transmitted.

As described above in connection with the wireless actuation system, the wireless transmitter may be a single button, two button, or three button transmitter. Further, the wireless transmitter may be configured to output one or more of a first, second, third, and fourth signal. The first signal may, for example, be a command signal to instruct a wireless actuated pump to deliver a fluid, such as water, from a fluid reservoir. The second signal may, for example, be a command signal to instruct a wireless actuated pump to stop pumping, or delivering a fluid. The third signal may, for example, be a command signal to instruct a wireless actuated pump to pump in a reverse direction so as to deliver fluid from a refill reservoir to the portable fluid reservoir. The fourth signal may, for example, be a command signal to instruct a wireless actuated pump to pause. For example, the wireless actuated pump may be configured to ignore (or not respond to) any signal received from the wireless transmitter until, for example, a resume command signal is received. The wireless transmitter may be configured to transmit at least one of the first, second, third, and fourth signals when the connector is connected to the mating connector and the microswitch is open and/or when the connector is disconnected from the mating connector.

In embodiments where the vehicle steering mechanism comprises a handlebar, the first and second mounting means may be configured to attach the microswitch and the transmitter to the handlebar, respectively. For example, for a motorcycle, the first mounting means may be configured to attach the microswitch on the clutch lever attached to the handlebar of the motorcycle. For a vehicle including a steering wheel, the first mounting means may be configured to attach the microswitch to the steering wheel and the second mounting means may be configured to attach the wireless transmitter to a rear side of a hub of the steering wheel. Alternatively, the microswitch may be attached to a front side of a hub of the steering wheel, and the transmitter may be attached to a rear side of the hub.

Magnetic Connector Rest

In another aspect of the present patent document, a magnetic connector rest is provided for a portable hydration system including a fluid reservoir, a headset including a magnetic quick connect at a proximal end of the headset, and a drink tube that is in fluid communication with the fluid reservoir at a proximal end of the drink tube and a fluid path extending through the headset at a distal end of the drink tube, where the magnetic quick connect comprises an upstream coupling member that includes a hose connector at its proximal end, a downstream coupling member that detachably couples with the upstream coupling member through a magnetic force, and the drink tube is in selective fluid communication with the fluid path through the headset by being connected to the hose connector at the proximal end of the upstream coupling member of the magnetic quick connect.

In one embodiment, the magnetic connector rest comprises a landing pad; a first magnetic material supported by the landing pad; and a base coupled to the landing pad and configured to be removably secured to a desired structure. The landing pad and/or first magnetic material are preferably arranged to define a mating surface configured to mate with a mating end of the upstream coupling member. The first magnetic material is preferably disposed on the landing pad so that when the upstream coupling member is brought into proximity with the landing pad, an attractive force between the first magnetic material and a second magnetic material included in the upstream coupling member will cause the mating end of the upstream coupling member to mate with the mating surface of the landing pad and detachably hold the upstream coupling member against the mating surface. In this way, the upstream coupling member and the mating surface of the landing pad may readily be connected by a user with a single hand without having to be able to view the upstream coupling member or the landing pad when attaching the upstream coupling member to the magnetic connector rest.

In some embodiments, the mating surface is configured to protect the mating end of the upstream coupling member from dirt and other debris when mated with the mating surface. Further, the mating surface may include a shelf with a mating male or female structural feature for mating with a corresponding female or male structural feature, respectively, on the mating end of the upstream coupling member. In such embodiments, the first magnetic material may be ring-shaped and the mating feature may be arranged coaxial with the first magnetic material. For example, the mating surface may comprises a shelf with a recess defining a protrusion receiving area, and the first magnetic material may be disposed about the recess. Preferably, the first magnetic material is ring-shaped and the protrusion receiving area extends coaxially through the first magnetic material.

Preferably, the first magnetic material of the magnetic connector rest comprises a material selected from the group consisting of a ferromagnetic material and ferrimagnetic material. Even more preferably, the first magnetic material comprises a permanent magnet.

The first magnetic material may be sized so that an axial pull force that is greater than about 32 ounce-force and less than about 128 ounce-force between the landing pad and the upstream coupling member is required to decouple the upstream coupling member from the mating surface of the landing pad in the axial direction. More preferably, an axial pull force that is greater than about 64 ounce-force and less than about 96 ounce-force, and even more preferably an axial pull force that is greater than about 72 ounce-force and less than about 88 ounce-force, is required to decouple the upstream coupling member from the mating surface of the landing pad in the axial direction.

In some embodiments, the upstream coupling member comprises a male coupling member and the mating end of the male coupling member includes a protrusion that comprises a body of revolution. In such embodiments, the mating surface may include a shelf with a recess defining a protrusion receiving area, and the first magnetic material may be disposed about the recess. The protrusion receiving area is preferably sized so that the male coupling member may be decoupled from the mating surface by pivoting the coupling member relative to the mating surface through the application of a torque. The mating surface may be configured, for example, so that the distance that the protrusion extends into the protrusion receiving area is less than the minimum diameter of the portion of the protrusion receiving area that receives the protrusion.

Further, in some embodiments, the first magnetic material is preferably sized so that the upstream coupling member may also be decoupled by pivoting the upstream coupling member relative to the landing pad through the application of a torque. Preferably the torque required to be applied to the upstream coupling member to decouple it from the landing pad is in the range of about 16 ounce-inches to about 72 ounce-inches. More preferably the torque is in the range of about 35 ounce-inches to about 64 ounce-inches, and even more preferably in the range of about 48 ounce-inches to about 60 ounce-inches to the upstream coupling member.

In some embodiments, the base may comprise a mounting bracket. Further, the mounting bracket may comprise a clip. The clip may, for example, be generally C-shaped with two opposing resilient arms that are anchored at a common end and include opposing extensions that extend toward one another at their opposite ends. The opposing resilient arms may be configured to define a backpack strap receiving area therebetween that can be accessed through an adjustable gap provided between the opposing extensions. The opposing resilient arms are preferably configured so that when they are in an unbiased state the adjustable gap between the opposing extensions is sized to prevent straps of a predetermined size from accessing the strap receiving area. Further, the resilient opposing arms are preferably configured so that when the opposing resilient arms are pulled away from one another, a biasing force tends to bias the opposing resilient arms in a direction toward one another, and the adjustable gap can be made to be of sufficient width to allow straps of the predetermined size to access (or be removed from) the strap receiving area so that once a strap of the predetermined size is inserted in the strap receiving area and the opposing arms are no longer pulled away from one another they will clamp onto the strap of the predetermined size.

In some embodiments, the base may further comprise a hook or loop fastener strip disposed on the back side of the base for mounting on a corresponding fastener strip disposed on a shoulder strap. In still other embodiments, the base may include a pair of opposing straps, where each strap is attached at one end to opposite sides of the base at one end, and the other end of each of the straps comprises a hook and a loop fastener, respectively.

Fluid Control Unit

In another aspect of the present patent document, a fluid control unit of a fluid delivery system for a hydration system is provided. In one embodiment, the fluid control unit comprises: a housing; a pump disposed within the housing; a controller operably connected to the pump to control the pump; and a power source in electrical communication with the pump via the controller. The controller is configured to process one or more command signals received from a wireless transmitter in wireless communication with the controller. An inlet of the pump is in fluid communication with a first coupling member of a first mechanical quick connect and an outlet of the pump is in fluid communication with a second coupling member of a second mechanical quick connect. For example, in some embodiments, an inlet tube may be connected to the inlet of the pump at one end and the first coupling member of the first mechanical quick connect on the other end, and an outlet tube may be connected to the outlet of the pump at one end and the second coupling member of the second mechanical quick connect on the other end.

In some embodiments, the first coupling member of the first mechanical quick connect comprises a male connector, and the housing comprises a recess extending from a bottom wall of the housing to a horizontal support wall. A portion of the male connector extends through a hole in the horizontal support wall. For example, in some designs, a hose connector at one end of the male connector may extend through the hole in the horizontal support wall so that a connector portion of the male connector is disposed on the exterior of the housing and the hose connector of the male connector is disposed on the inside of the housing and the inlet tube is connected thereto. The recess is preferably sized to receive an outlet spout of a hydration reservoir bag, where the outlet spout includes a mating female mechanical quick connector disposed at the end of the outlet spout. The recess is also preferably sized so as to permit a user to access a release on the mating female quick connector when the male connector and mating female connector are connected so as to permit a user to uncouple them. With the foregoing design, the fluid control unit may lie flat against a conventional fluid reservoir bag, such as a CAMELBAK™ reservoir bag, and still fit within a conventional hydration backpack.

Further aspects, objects, desirable features, and advantages of the various inventions that are the subject of the present disclosure will become manifest and be better understood from the following description considered in connection with accompanying drawings in which various embodiments of the disclosed inventions are illustrated by way of example. It is to be expressly understood, however, that the drawings are for the purpose of illustration only and are not intended as a definition of the limits of any of the disclosed inventions.

BRIEF DESCRIPTION OF THE DRAWINGS

FIG. 7C is a top view of the headset of FIG. 7A with male and female coupling members of magnetic quick connects included in the headset being separated.

FIG. 7D is a cross-sectional view of the mounted headset of FIG. 7C taken along the line 7D-7D.

FIG. 8A is an isometric cross-sectional view through one embodiment of a magnetic quick connect along its centerline.

FIG. 8B is another cross-sectional view through the magnetic quick connect of FIG. 8A along its centerline.

FIG. 9A is an exploded isometric view of a magnetic quick connect from the male side of the quick connect.

FIG. 9B is an exploded isometric view of the magnetic quick connect of FIG. 9A from the female side of the quick connect.

FIG. 9C is an isometric view of assembled male and female connectors of the magnetic quick connect shown in FIG. 9A, but with the two connectors separated.

FIG. 9D is an isometric view of assembled male and female connectors of the magnetic quick connect shown in FIG. 9B, but with the two connectors separated.

FIG. 9E is an assembled isometric view of the magnetic quick connect of FIG. 9D showing the female and male connectors connected.

DETAILED DESCRIPTION

While it should be understood that the inventions described herein are described in connection with particular examples, the scope of the inventions are not limited to the specific examples. Rather, those skilled in the art will appreciate after reviewing the present disclosure that the following teachings can be used in a much wider variety of applications than the examples specifically mentioned herein.

Figure 1:
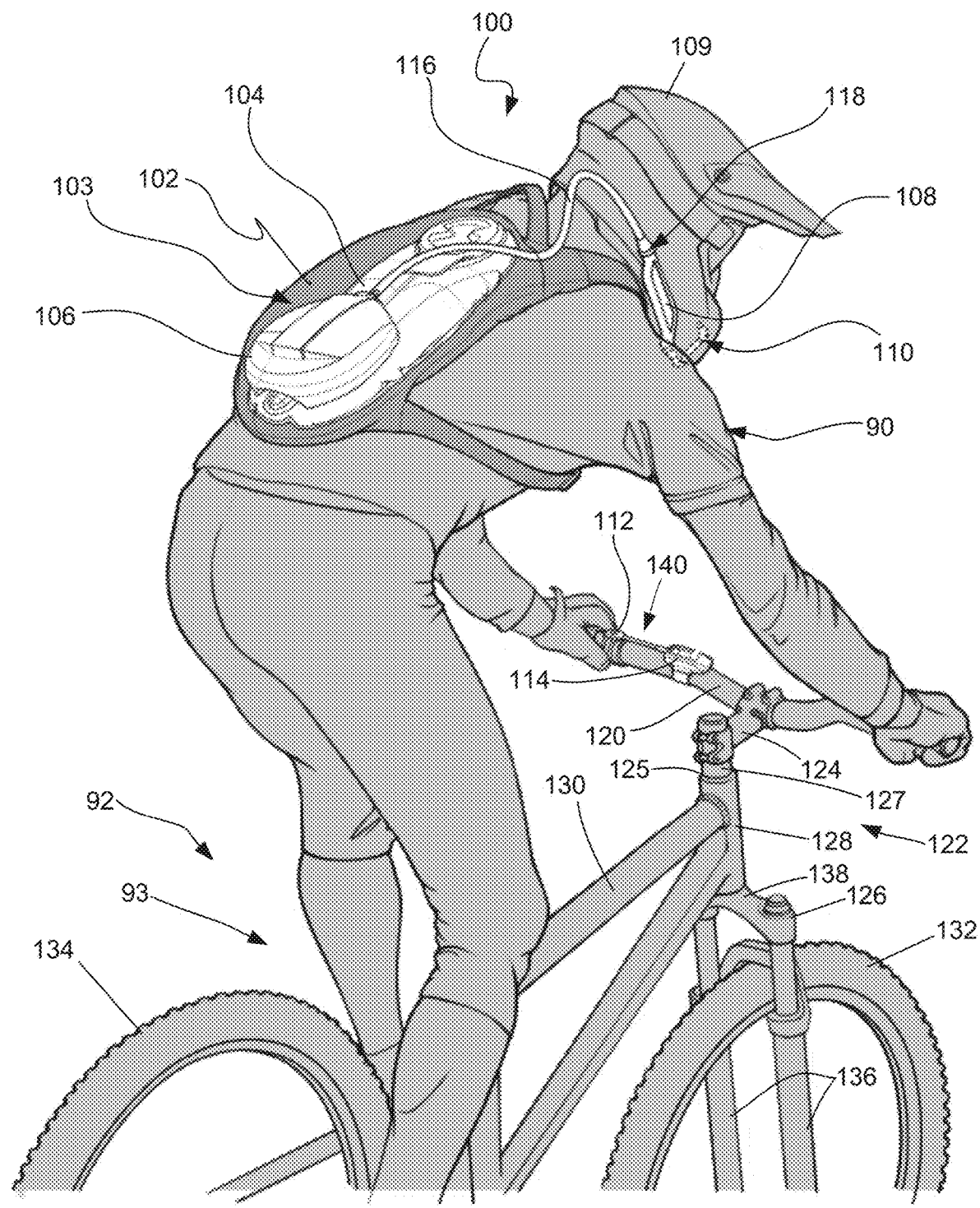
FIG. 1 illustrates one application of a personal hydration system that includes a fluid delivery system including a fluid control unit, a headset, a magnetic quick connect, and a wireless actuation system.

Referring now to the drawings in which like reference numerals designate like or corresponding components throughout the drawings, there is shown in FIG. 1 a schematic illustration of a vehicle 92 and a personal hydration system 100 according to the present patent disclosure. Vehicle 92 and the personal hydration system 100 each incorporate a number of distinct aspects. Distinct aspects of the personal hydration system include, for example, its fluid delivery system 103, fluid control unit 106, headset 108, mouthpiece assembly 110, magnetic quick connect 118, and wireless actuation system 140. It is to be expressly understood that each of these various aspects, as well as other inventive features of the vehicle 92 and personal hydration system 100 described below, both individually as well as in combination, all form distinct and separately patentable inventions contemplated by the present disclosure. Thus, for example, while each of these distinct aspects have all been incorporated into an illustrative embodiment of a personal hydration system 100, it is to be expressly understood that because each of these aspects are separately patentable, they can be used individually or collectively in many other fluid delivery systems, including fluid delivery systems for other hydration systems and other vehicles, without departing from the spirit of the present disclosure. Thus, it is also to be expressly understood that the present patent disclosure is not restricted to the personal hydration system embodiments described herein. Indeed, as will become apparent to those skilled in the art after reviewing the present disclosure, one or more aspects of the vehicle 92 and personal hydration system 100 may readily be incorporated into other vehicles, personal hydration systems and/or fluid delivery systems without departing from the scope of the present disclosure. By way of illustration, but not limitation, the magnetic quick connects of the present disclosure, may, for example, be used in a host of fluid delivery systems unrelated to personal hydration systems, including in gas delivery systems rather than liquid delivery systems.

Figure 2:
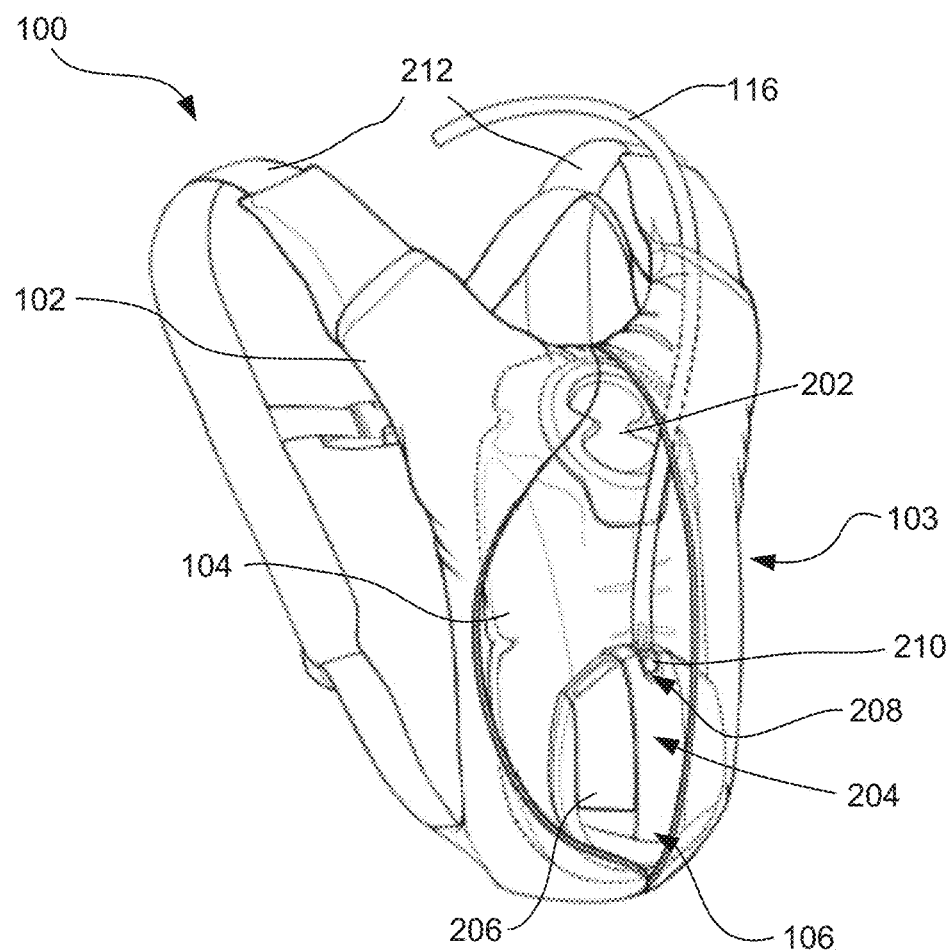
FIG. 2 is a schematic illustration of components of a personal hydration system.

Referring to FIGS. 1 and 2, a user 90 is shown with a personal hydration system 100 while using a vehicle 92, which in the illustrated embodiment is a bicycle 93. Personal hydration system 100 includes a fluid reservoir 104 that is in fluid communication with a fluid delivery system 103, which provides a fluid communication or delivery path from (and in some embodiments to) the reservoir. A magnetic quick connect 118 is preferably interposed in the fluid deliver path of fluid delivery system 103. Interposing magnetic quick connect 118 into the fluid delivery path of fluid delivery system 103 allows the upstream components of the fluid delivery system 103 to readily be attached to and detached from downstream components of the fluid delivery system 103.

In the embodiment shown in FIGS. 1 and 2, fluid delivery system 103 includes a fluid control unit 106, dispensing hose 116, and headset 108, all of which are in fluid communication with each other and fluid reservoir 104. Fluid delivery system 103 also preferably includes a wireless actuation system 140. Fluid control unit 106 and wireless actuation system 140 collectively form a wireless pump system.

Fluid control unit 106, which is illustrated in FIGS. 1-6, includes a pump 306 that is disposed within a housing 204. As described in detail below, wireless actuation system 140 wirelessly and remotely controls the actuation of the pump 306.

In order to remotely control the actuation of pump 306, wireless actuation system 140 is in wireless communication with a controller 428 provided on circuit board 408 within housing 204 of fluid control unit 106. Controller 428 is in turn electrically and operably connected to pump 306 and power source 423 so as to provide the necessary power to drive the motor of pump 306 when instructed by the wireless actuation system 140. As a result, wireless actuation system 140 may be used to wirelessly control the operation of pump 306 via controller 428.

While in the illustrated embodiment a wireless actuation system 140 is employed to control the operation of pump 306, in other embodiments a switch 112 that is electrically connected to pump 306 or controller 428 may be used. As will be appreciated from the teachings of the present patent document, however, in addition to eliminating the need for at least two conductors to electrically connect the switch 112 to the pump 306 or controller 428, the wireless actuation system 140 provides a number of advantages over a switch 112 that is electrically connected to pump 306 or controller 428.

As shown in FIGS. 1 and 2, the fluid reservoir 104 and portions of the fluid delivery system 103 are held within a backpack 102 worn on the back of user 90. More particularly, backpack 102 includes left and right shoulder straps 212 for securing backpack 102 to the left and right shoulders of user 90 in a conventional manner so that the reservoir 104 is positioned over the back of user 90 when the user 90 is wearing the backpack 102.

Flexible reservoirs such as those provided by CAMEL-BAK™ are particularly well suited for use as fluid reservoir 104 of the hydration system 100 of the present patent document. As seen best in FIG. 2, such reservoirs fit well within the conventional hydration backpack 102 along with a number of other components of the fluid delivery system 103, including the fluid control unit 106 and the proximal end of dispensing hose 116.

As used herein, unless otherwise specified, the terms "proximal" and "distal" are used in relation to fluid reservoir 104. Thus, for example, the proximal end of dispensing hose 116 would be the end of dispensing hose 16 closest to the outlet port (not shown) of reservoir 104, while the distal end of dispensing hose 116 would be the end of dispensing hose furthest away from the outlet port of fluid reservoir 104.

Fluid reservoir 104 includes a fill cap 202 through which a desired hydration fluid, such as water or a sports drink, may be added to reservoir 104. As is conventional, in order to fill reservoir 104 through the fill port sealed by fill cap 202, the reservoir 104 is preferably removed from backpack 102, the fill cap removed, and then the desired fluid added to the reservoir 104. However, when a flexible reservoir 104, such as a conventional CAMELBAK™ reservoir, is filled through fill port in this manner, the reservoir cannot be filled to its maximum capacity because fluids will begin to spill out of the fill port before the reservoir 104 is stretched to its maximum capacity. Further, once reservoir 104 is filled in this manner, it can be difficult to stuff it back into backpack 102.

The reservoir 104 may be removed from, and put back into, backpack 102 through a closeable opening provided in backpack 102 in a conventional manner. The closeable opening may be provided by any conventional closing mechanism, including, for example, a zipper or a flap closure that may be closed with a variety of closure mechanisms, including, for example a strap and corresponding buckle or hook and loop fasteners.

Although flexible hydration reservoirs, such as those provided by CAMELBAK™, are particularly well suited for use as fluid reservoir 104 in the hydration system 100 of the present patent document, any suitable sealable container can be used for fluid reservoir 104. For example, depending on the application reservoir 104 may be made from rigid, semi-rigid, or flexible material. Furthermore, in some applications, it may be desirable to use a reservoir that is insulated, such as an insulated bottle or jug, for the reservoir 104. Alternatively, the reservoir 104 may be included within an insulated sleeve in some embodiments.

Regardless of the particular form of reservoir 104, the material or materials used in its construction (particularly any that will come in contact with the fluids contained within reservoir 104) should be suitable for contact with liquids that are intended for human consumption. This is also true with the other portions of hydration system 100 that may come in contact with fluid that is transported from the reservoir 104 through fluid delivery system 103 to the user 90.

Backpack 102 may comprise any suitable conventional personal hydration backpack. In addition, backpack 102 may comprise other backpacks suitable for holding the hydration reservoir 104 and the illustrated components of the fluid delivery system 103. Further, in still other embodiments, the fluid reservoir 104 and illustrated components of the fluid delivery system may be carried by the user using a variety of other suitable means, including for example, a waist pack or chest pack.

Figure 25:
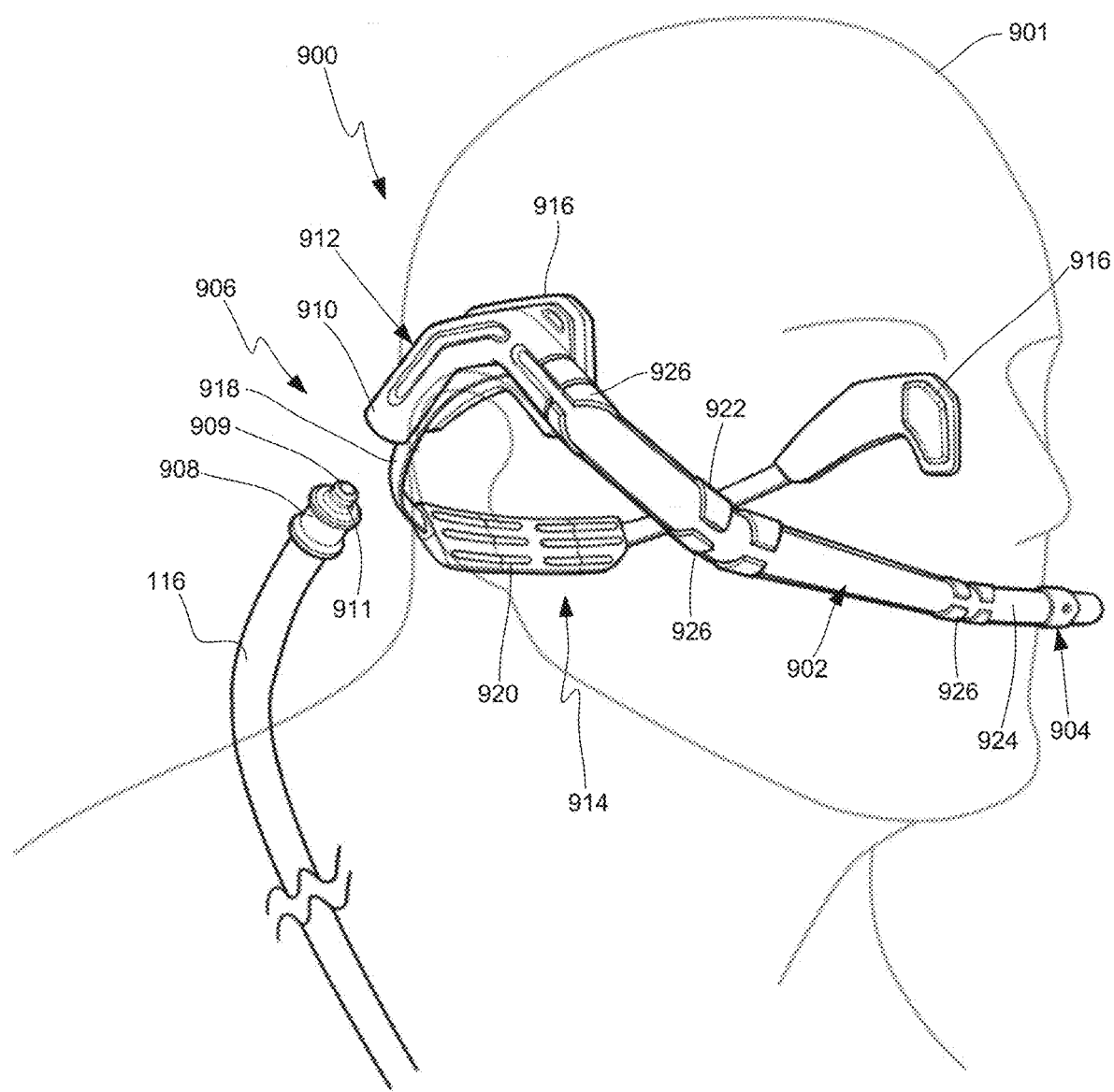
FIG. 25 is perspective view of an alternative embodiment of a headset that may be used in a fluid delivery system.
Figure 26:
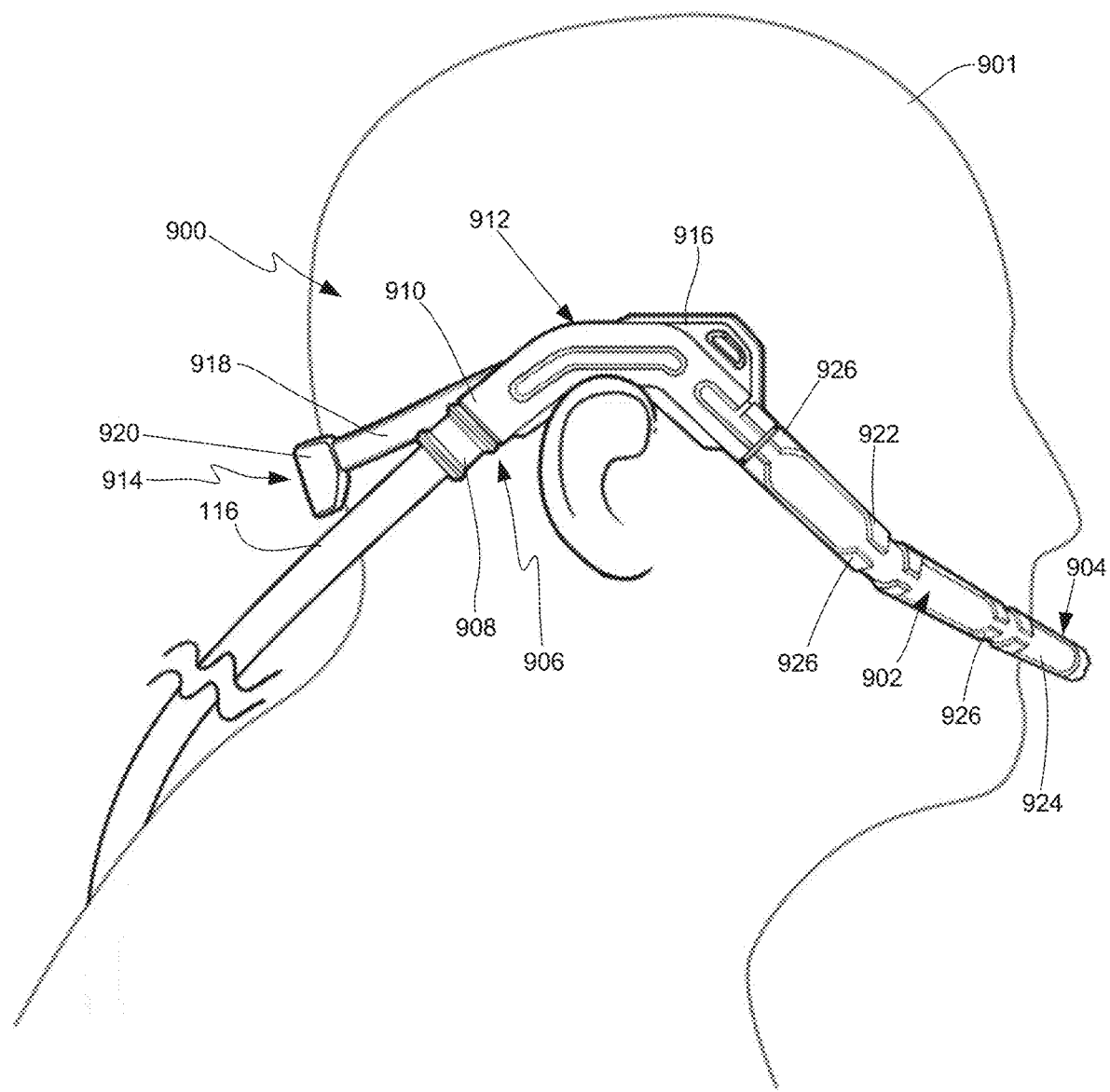
FIG. 26 is a side view of the headset of FIG. 25.

Those skilled in the art will also appreciate from reviewing the present patent document that by changing the headset 108 to another form of headset, such as headset 900 shown in FIGS. 25 and 26, for example, the hydration system 100 can be used in a wide variety of applications not requiring a headset to be attached to a full face motorcycle helmet or even a helmet. Indeed, with the headset 900, a user 901 can use the hydration system 100 according to the present patent document in a wide variety of non-helmeted and/or non-vehicle related applications. Illustrative potential applications of a headset, such as headset 900, that is not required to be mounted to a helmet include, by way of example, backpackers, joggers, hikers, climbers, workers, firefighters, police, and military personnel.

The various embodiments of headsets of the present patent disclosure preferably include a support structure configured to support the headset on headgear adapted to be worn on a user's head. The support structure may, for example, comprise a mounting bracket, such as mounting bracket 710 shown in FIGS. 7A-F or mounting bracket 912 shown in FIGS. 25 and 26. The mounting bracket may be (i) attached to headgear (e.g., helmet 109 shown in FIGS. 1, 13 and 14; helmet 871 shown in FIG. 16; head bracket 914 shown in FIGS. 25 and 26; or other headgear) adapted to be worn on a user's head, or (ii) configured to attach to headgear (e.g., a helmet 109 shown in FIGS. 1, 13 and 14; helmet 871 shown in FIG. 16; hat or other headgear) that is adapted to be worn on a user's head. In this way the support structure of the headset may either be already attached to headgear or it may be configured so as to attach to headgear and support the headset on the headgear once attached. In still further embodiments, at least a portion of the support structure may be formed integral with the headgear. This, for example, may be desirable for certain safety headgear like helmets and hard hats, as is illustrated with the integrated headset 938 of helmet 109 shown in FIG. 28.

Figure 13:
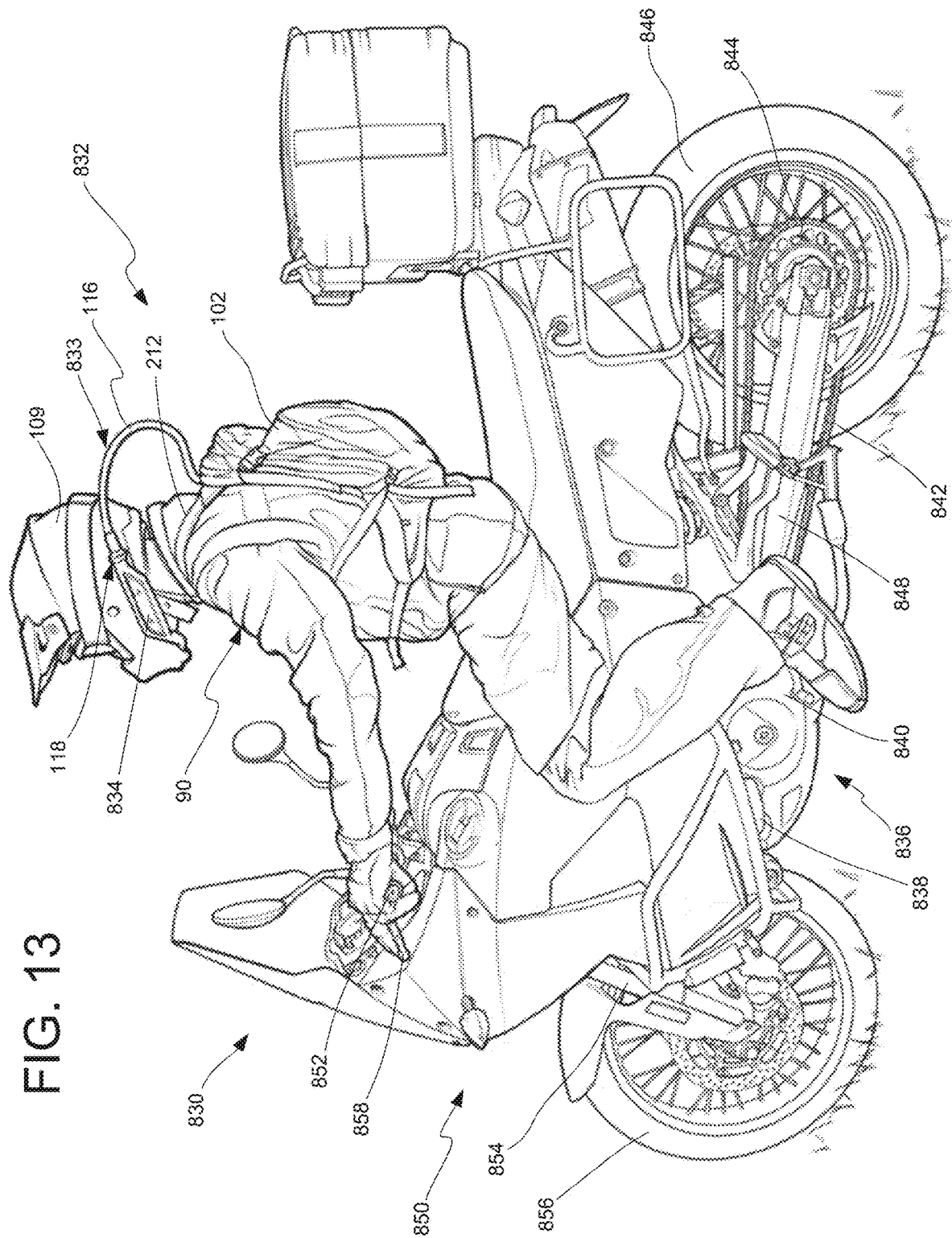
FIG. 13 illustrates a motorcycle with a personal hydration system that includes a fluid delivery system including a fluid control unit, a headset, and a magnetic quick connect.
Figure 16:
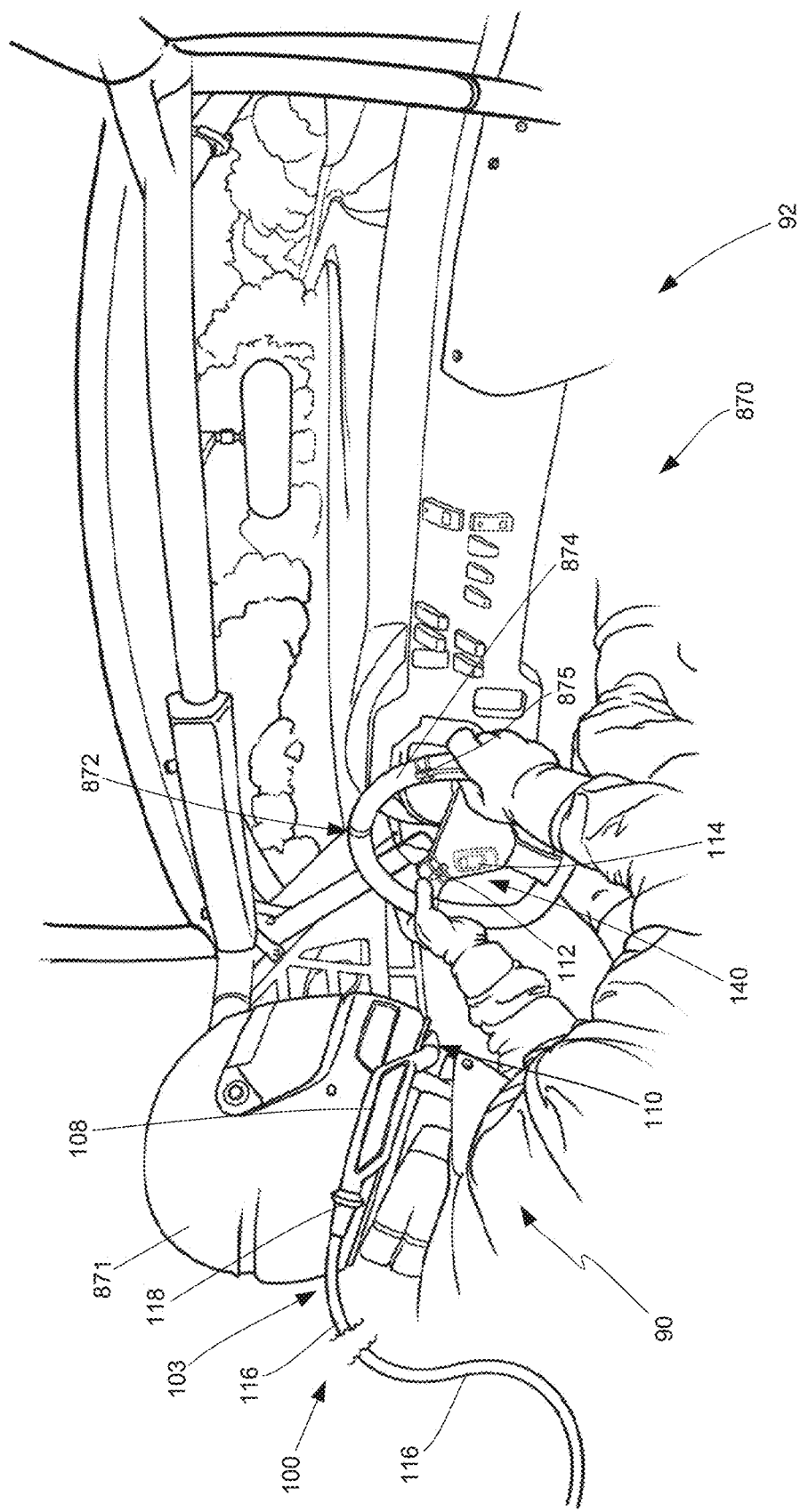
FIG. 16 illustrates an exemplary race car with a personal hydration system.

Although motorcycle helmet 109 shown in FIGS. 1 and 13 and the auto racing helmet 871 shown in FIG. 16 are each full face helmets, the headsets described in the present patent document may be attached to, or integrated with, any type of helmet, including, for example, motorcycle helmets (half, three quarter, open face, and full face), auto racing helmets (open face or full face), cycling helmets, skateboarding helmets, snowboarding and skiing helmets, mountain climbing helmets, military and other tactical helmets, fire helmets, safety helmets, and rescue helmets.

Referring back to FIGS. 1 and 2, the fluid reservoir 104 of the hydration system 100 is in fluid communication with fluid delivery system 103. The fluid delivery system 103 of hydration system 100 defines a fluid communication or delivery path that extends from the proximal end of the fluid delivery system 103 to the distal end of the fluid delivery system 103. The proximal end of the fluid communication path provided by the fluid delivery system 103 is adapted to connect, preferably removably connect, to the outlet port (not shown) of the reservoir 104. Therefore, when the proximal end of the fluid communication path is connected to the outlet port of the fluid reservoir 104, the fluid communication path within the fluid delivery system 103 will be in fluid communication with the reservoir 104.

As seen in FIGS. 3A and 7A-F, the distal end of the fluid communication path defined by the fluid delivery system 103 includes an outlet port 348 for delivering a hydration fluid, such as water or a sports drink, to user 90 from fluid reservoir 104. The fluid communication path provided by the fluid delivery system 103 should thus have a length sufficient to extend from the reservoir 104 to a location proximate the mouth of user 90. This will mean that the overall length of the fluid delivery system may need to vary depending on where the reservoir 104 is located in relation to the user 90 and the height of the user 90. However, the length of the fluid path provided by the fluid delivery system 103 is readily adjustable by, for example, adjusting the length of the dispensing hose 116.

In the present embodiment, outlet port 348 is provided in the distal end of a mouthpiece 346 that is provided at the distal end of the fluid delivery system 103. In other embodiments, the outlet port 348 of the fluid communication path may be provided by other suitable structures, including, for example, the distal end of dispensing hose 116 in some embodiments.

Referring to FIGS. 2 through 5 the fluid communication or delivery path of the fluid delivery system 103 is provided by a series of components that are each connected so that they are in fluid communication with one another. For example, in the illustrated embodiment, the fluid communication path is provided by inlet male quick connector 314 which in turn is connected to inlet tube 310. Inlet tube 310 is in turn connected to the inlet of pump 306 and the outlet of pump 306 is then connected to outlet tube 312. Outlet tube 312 is in turn connected to a female quick connector 322 which in turn is connected to a mating male quick connector 328 provided at the proximal end of dispensing hose 116. The distal end of hose 116 is in turn connected to the proximal end of a fluid conduit 704 (shown in FIGS. 7B and 7D) that extends from a proximal end of headset 108 to a distal end of headset 108 where it terminates with outlet port 348.

In the illustrated embodiment, magnetic quick connect 118 forms the proximal end of headset 108, but in other embodiments, magnetic quick connect 118 may be interposed in the fluid delivery path of fluid delivery system 103 in a different location. Moreover, in some embodiments, a second magnetic quick connect, such as magnetic quick connect 340 may be included in the fluid delivery path defined by fluid delivery system 103.

The components defining the fluid delivery path of fluid delivery system 103 shown in FIGS. 1-7 are exemplary in nature, and in other embodiments of fluid delivery system 103, additional components, fewer components, or completely different components may be used to form the fluid delivery path of fluid delivery system 103. In general terms, however, the fluid delivery system 103 will typically include a fluid delivery path having a proximal end adapted to be attached to fluid reservoir 104 so that fluid communication between the fluid delivery path and the fluid reservoir 104 may be established. In addition, the fluid delivery path will include an outlet port, such as outlet port 348, for delivering hydration fluid to user 90 from fluid reservoir 104. In preferred embodiments, a magnetic quick connect, such as magnetic quick connect 118, is interposed in the fluid delivery path of the fluid delivery system 103.

Although magnetic quick connect 118 may be interposed in the fluid delivery path of fluid delivery system 103 in a variety of locations, as best seen in FIGS. 1, 3A, 7B and 7D, for improved user safety the proximal end of headset 108 preferably comprises magnetic quick connect 118. As a result, the proximal end of the fluid conduit 704 provided within headset 108 is preferably defined by the male and female coupling members 334, 336 of magnetic quick connect 118. The upstream end of magnetic quick connect 118 may include a hose connector 714 for connecting to distal end of dispensing hose 116. Preferably the hose connector 714 comprises a hose connector, such as a barbed hose connector, that permits the dispensing hose to be removably connected to magnetic quick connect 118 of headset 108.

Magnetic quick connector 118 may also comprise a removable hose collar 338. Hose collar 338 includes a tubular receiving hole sized to receive the hose connector 714 and dispensing hose therethrough. Hose collar 338 helps protect connector 714 from potential damage. It also helps prevent dispensing hose 116 from unintentionally dislodging from connector 714. For example, the tubular receiving hole may be sized so that as hose collar 338 is slid over the connection between dispensing hose 116 and barbed hose connector 714, it will compress the wall of dispensing hose 116 into the barbs of barbed hose connector 714, thereby increasing the force required to separate hose 116 from connector 714.

As explained in greater detail below, one advantage of including a magnetic quick connect 118 at the proximal end of headset 108 is that male and female coupling members 334, 336 of quick connect 118 may be configured so that the upstream components of the fluid delivery system 103 will readily disconnect from headset 108 in the event that one of the upstream components get snagged by a tree limb or other object in the environment in which the user 90 is riding.

While in the illustrated embodiment, the upstream end of magnetic quick connect 118 comprises a male coupling member 334, in other embodiments the upstream end of the magnetic quick connect 118 may comprise a female coupling member 336.

The mechanical female quick connector 322 and mating male quick connector 328 collectively form a mechanical quick connect 208. A number of suitable mechanical quick connectors exist on the market that may be used for quick connect 208. For example, connectors provided by Cold Products Company ("CPC"), located at 1001 Westgate Drive, St. Paul, MN 55114, under parts numbers APCD17004SH and APC22004 may be used for female connector 322 and male connector 328, respectively, of mechanical quick connect 208. CPC's APCD17004SH comprises a valved female in-line coupling body with a shroud on one end and a ¼ inch barbed hose connector on the other end. CPC's APC 22004 comprises a non-valved in-line male coupling insert on one end and a ¼ inch barbed hose connector on the other end. Both CPC connectors are made from acetal, or polyoxymethylene. The connectors corresponding to CPC parts numbers APCD17004SH and APC22004 may be found at the following URLs, respectively: http://www.cpcworldwide.com/product-list/Series/1/Product/293 and http://www.cpeworldwide.com/product-list/Series/l/Product/275.

The female and male connectors 322, 328 of mechanical quick connect 208 may be quickly and repeatedly connected and disconnected from one another. However, once connected, in order for the female and male connectors 322, 328 to be disconnected from one another the quick connect release button 210 must be pressed. Without the release button 210 being pressed, the male and female quick connectors 322, 328 will remain firmly engaged with one another thereby ensuring a strong connection between the mating connectors 322, 328 and that the mating connectors 322, 328 may only be disconnected when the user 90 intends them to be disconnected by the pressing of the quick connect release button 210.

Inlet male quick connector 314 is selected so as to mate with a mating female quick connector, such as those provided on the outlet port of a number of conventional CAMELBAK™ reservoirs. As a result, the fluid control unit 106 of the fluid delivery system 103 may be quickly connected to and disconnected from the outlet port of reservoir 104 in the manner just described for mechanical quick connect 208. Further, a suitable inlet male quick connector 314 may be obtained from the same source as female quick connector 322 and mating male quick connector 328 of mechanical quick connect 208. Indeed, the connector corresponding to CPC's part number APC22004 that is used for male quick connector 328 may also be used for male quick connector 314.

While a male quick connector 314 is provided at the distal end of the fluid delivery path of fluid delivery system 103, in other embodiments a female quick connector 322 may be used instead. This may be desirable, for example, where fluid reservoir 104 employs a male quick connector instead of a female quick connector on its outlet port.

Preferably the distal end of inlet male quick connector 314 and proximal end of outlet female quick connector 322 are provided with a hose connector, such as barbed hose connectors 320, 324, for removably connecting to the proximal end of inlet tube 310 and distal end of outlet tube 312, respectively. Similarly, the distal end of inlet tube 310 and proximal end of outlet tube 312 are preferably removably connected to the inlet and outlets of pump 306, respectively, using for example, standard barbed hose connectors. Male quick connector 322 is likewise preferably removably connected to the proximal end of hose 116 via a hose connector, such as barbed hose connector 330. Other suitable connectors may also be used in place of the various barbed hose connectors shown in the figures and described herein.

Although barbed hose connectors, such as barbed hose connectors 320, 324, 330, and 714 permit a hose or tube to be removably connected thereto while also establishing a fluid-tight seal, as those skilled in the art will appreciate, the attachment and detachment of a hose or tube from a barbed hose connector does not occur with the same ease as the coupling and decoupling of male and female connectors of a mechanical quick connect, such as mechanical quick connect 208. However, a mechanical quick connect 208 cannot be coupled and decoupled with the same ease as the male and female coupling members 334, 336 of magnetic quick connect 118. Indeed, including a magnetic quick connect, such as magnetic quick connect 118, in the fluid delivery path of fluid delivery system 103 provides a number of advantages to the fluid delivery system 103 that cannot be provided by a mechanical quick connect 208 or a barbed hose connector.

Barbed hose connectors, for example, tend to form a tight friction fit with the connecting hose or tube that is typically difficult to establish or release. As a result, barbed hose connectors are not optimal in terms of both providing a fluid-tight seal and permitting components downstream of the reservoir 104 to be quickly and repeatedly coupled and uncoupled by a user 90. They also require a user 90 to employ two hands to attach or detach a hose or tube to the connector. And while a mechanical quick connect, such as mechanical quick connect 208, may be quickly and easily coupled and uncoupled, one drawback of mechanical quick connects is that once its male and female connectors are connected they can only be disconnected by pressing a release button, such as release button 210. As a result, neither friction fit barbed hose connectors nor mechanical quick connects are designed to permit components downstream of the reservoir to be easily and safely disconnected in the event of an emergency or in the event of something snagging one of the components of the fluid delivery system, such as hose 116. As a result, a fluid delivery system that only includes barbed hose connectors and/or mechanical quick connects can pose a significant safety problem in a number of sporting and work related activities.

Another drawback of mechanical quick connects 208 is that depending on the location of the mechanical quick connect in the fluid delivery system 103, two hands may actually be required to connect and/or disconnect the female and male connectors 322, 328 of the quick connect provided on the mating components of the hydration system 100. Moreover, neither barbed hose connectors nor mechanical quick connect 208 are designed to permit a user 90 to attach or detach mating components without the benefit of the user visualizing the mating components when they are to be connected or disconnected.

In contrast to barbed hose connectors (e.g., 320, 324, 328, 714) or mechanical quick connects (e.g., 208), the male and female coupling members 334, 336 of magnetic quick connect 118 may be configured to permit a user 90 to couple and uncouple the coupling members 334, 336 and their associated components with a single hand and without actually viewing the coupling members 334, 336 when they are to be coupled together or uncoupled. For example, the male and female coupling members 334, 336, may be configured so that magnetic force of attraction between the two coupling members 334, 336 is such that the user 90 need only bring the two coupling members into proximity with (although not necessarily even touching) one another and the magnetic force of attraction between the two coupling members 334, 336 will automatically align and couple the members 334, 336 together in a fluid tight manner. As a result, user 90 need not be able to visualize the male and female coupling members 334, 336 of magnetic quick connect 208 when coupling or uncoupling them. Furthermore, as the strength of the magnetic force of attraction between the coupling members 334, 336 is increased, then user 90 will not need to bring the coupling members 334, 336 as close together in order for the magnetic force of attraction between the two coupling members 334, 336 to automatically align and couple the members 334, 336 together in a fluid tight manner.

The user can also rely on the haptic feedback provided by the magnetic force of attraction between the two coupling members 334, 336 to know when he or she has brought male coupling member 334 sufficiently close to, and sufficiently aligned with, coupling member 336 so as to release coupling member 334 and allow the magnetic force of attraction between the two coupling members 334, 336 to finish aligning and coupling the members 334, 336 together in a fluid-tight manner. The strength of the magnetic force of attraction between the two coupling members 334, 336 can also be set so that when the two coupling member 334, 336 couple together as a result of the magnetic force of attraction that a distinct, audible noise, such as an audible "clacking" noise, will be made due to the two coupling members coming together in a fluid-tight manner. As a result, user 90 can listen for the clacking or other distinct noise to verify that coupling members 334, 336 have been properly coupled together in a fluid-tight manner without ever visualizing the two coupling members when coupling them together.

Furthermore, the inclusion of a magnetic quick connect 118 in the fluid delivery path of fluid delivery system 103 also substantially increases the safety of hydration system 103 over conventionally known hydration system designs for a wide variety of uses or applications. For example, while the male and female coupling members 334, 336 may be configured so that magnetic force of attraction between the two coupling members 334, 336 is sufficient to automatically align and couple the members 334, 336 together when they are brought into proximity to one another, the force of attraction may also be set so that the amount of force required to disconnect the male and female coupling members 334, 336 is such that the coupling members will disconnect without injuring the user 90 in the event that a portion of dispensing hose 116 is snagged on an object, such as a tree limb, while user 90 is riding bicycle 93 or motorcycle 830 (shown in FIG. 13). Similarly, in the event user 90 crashes car 870 (shown in FIG. 16) or some other emergency occurs that requires user 90 to exit the cabin of car 870 quickly, the male and female coupling members 334, 336 will easily and automatically disconnect (without a release button 210 having to be pressed or a friction connection having to be undone) as the user 90 removes himself from the car 870, or the user 90 is extracted from the car 870 by a race track crew. These safety features may be particularly important in the event of a fire within the cabin of car 870 or a spinal injury to user 90.

At the same time, the strength of the magnetic force of attraction may be set and the material used for drink hose 116 (including its dimensions) may be selected so that when the proximal end of hose 116 is connected to a fluid reservoir 104 and a user, such as user 90, is wearing a headset or wearing headgear (e.g. helmet 109) to which the headset is mounted turns his or her head it does not cause the coupling members 334, 336 of the magnetic quick connect 118 to uncouple from one another. In this regard, hose 116 preferably has a Shore Durometer hardness in the range of about 50 A to 70 A on the Shore A scale.

Referring to FIGS. 7B, 7D, 8 and 9, the magnetic force of attraction between coupling members 334, 336 maybe increased, for example, by (i) increasing the thickness of the first and/or second magnetic materials 720, 734; (ii) increasing the cross-sectional area of the pole of the first and/or second magnetic materials 720, 734 that faces the other magnetic material ("the mating cross-sectional area"); (iii) increasing the flux density (B) and/or magnetization (A) of the first and/or second magnetic material 720, 734; and/or (iv) decreasing the thickness and/or magnetic permeability ($\mu$) of any non-magnetic material between the first and second magnetic materials 720, 734 and the mating surfaces of mating ends 716, 730 of male and female coupling members 334, 336, respectively. Conversely, the magnetic force of attraction between coupling embers 334, 336 may be decreased, for example, by adjusting parameters (i)-(iv) in the opposite direction.

As best seen in FIGS. 1, 3A, 4A and 4B, pump 306 is interposed in the fluid communication path of the fluid delivery system 103 so as to be able to pump fluids from reservoir 104 to outlet port 348. Switch 112, preferably a microswitch, is operably connected to the pump 306 so that operation of the microswitch 112 controls the operation of the pump 306.

In some embodiments microswitch 112 may be operably connected to the motor and pump assembly 306 by being hard wired to controller 428 (shown in FIG. 4B) provided on circuit board 408. The controller 428 is in turn operably connected to the pump 306 so as to control the operation of pump 428. In more preferred embodiments, however, the micoswitch 112 is operably connected to the pump/motor assembly 306 via a wireless connection between controller 428 and a wireless transmitter 114 that is removably mounted on the steering mechanism 122 proximate the microswitch 112.

In the embodiment shown in FIG. 1, the microswitch 112 is mounted on the handlebar 120 of steering mechanism 122 in a location sufficiently proximate to where a hand of user 90 would grip the handlebar 120 of steering mechanism 122 to steer the bicycle 92 so that user can operate the microswitch 112 without the user 90 removing his or her hand from the handlebar 120. In the embodiment illustrated in FIG. 1, the microswitch is mounted sufficiently proximate the left handlebar grip that user 90 can operate switch 112 with his or her thumb without removing his or her hand from the handlebar grip. In other embodiments, the microswitch 112 may be mounted on a front or rear break lever attached to the handlebar 120 of the steering mechanism 122 so that user 90 can operate the microswitch 112 with an index finger without removing his or her hand from the handlebar 120.

With the foregoing arrangements, the user 90 of the vehicle 92 may effortlessly remain hydrated without having to take his or her hand off the steering mechanism 122.

In the embodiment illustrated in FIG. 1, the fluid reservoir 104 is indirectly supported by the frame 130 of the bicycle 93 via the back pack 102 and the body of the user or rider 90. The same would also be true if the fluid reservoir were supported in a waist or chest pack carried by the user 90. In some embodiments, however, it may be desirable to support, either directly or indirectly, the fluid reservoir 104 on the frame of a vehicle 92 without the user 90 having to carry the reservoir on his or her person. For example, in the context of bicycle 93 this may be accomplished by directly hanging the reservoir 104 from the frame 130 or including it within a bag that is in turn strapped to or suspended from the frame 130.

Although vehicle 92 comprises a bicycle 93 in the embodiment shown in FIG. 1, the hydration system 100 may be used in connection with, as well as included with, any vehicle. For example, vehicle 92 may be any wheeled vehicle (motorized or non-motorized), aircraft, spacecraft, or watercraft. Thus, for example, vehicle 92 may be an airplane, ATC, ATV, bicycle, boat, car, helicopter, motorcycle, race car, sand rail, side-by-side, tank or truck.

Thus, for example, FIG. 16 illustrates a user 90 driving a vehicle 92 in the form of a race car 870. A hydration system 100 is included in the race car 870. Instead of being suspended in some form of pack from the user 90, however, the reservoir 104 (which is not shown in FIG. 16) of hydration system 100 is disposed within the cabin of race car 870 so as to be supported directly or indirectly by the frame of race car 870 at a location behind user 90. This also further illustrates that the fluid reservoir 104 may be supported directly or indirectly on the frame of a vehicle 92 without the user 90 having to carry the reservoir on his or her person.

Before continuing to describe additional details and variations of the hydration system 100, some structural details of bicycle 93 are first described. Referring back to FIG. 1, bicycle 93 includes a powertrain supported by frame 130. The powertrain of bicycle 93 includes, as is conventional, user or rider 90, a crank, front sprocket, chain, rear sprocket, and the rear wheel 134, which is the driven wheel of bicycle 93 and acts as the final drive mechanism for the powertrain of bicycle 93.

Hand operated steering mechanism 122 of bicycle 93 is also operably supported by the frame 130. The steering mechanism 122 of bicycle 93 includes handlebar 120, handlebar stem 124, headset 125, front fork 126, and front wheel 132. Handlebar 120 is mechanically connected to the steer tube 127 of front fork 126 via the handlebar stem 124 and headset 125 in a conventional manner. The steer tube 127 of the front fork 126 extends through the head tube 128 of frame 130, and the headset 125 rotatably secures steer tube 127 to the head tube 128. The axle of front wheel 132 is also rotatably secured to opposing fork blades 136 of the front fork 126 in a conventional manner. Fork blades 136 are joined together on their upper end by a fork crown 138 from which the steer tube 127 extends.

The above structure allows bicycle 93 to be steered by turning the handlebar 120 to angle front wheel 132 via the steering mechanism 122 in the desired direction.

Wireless Actuation System and Wireless Transmitters

Figure 10:
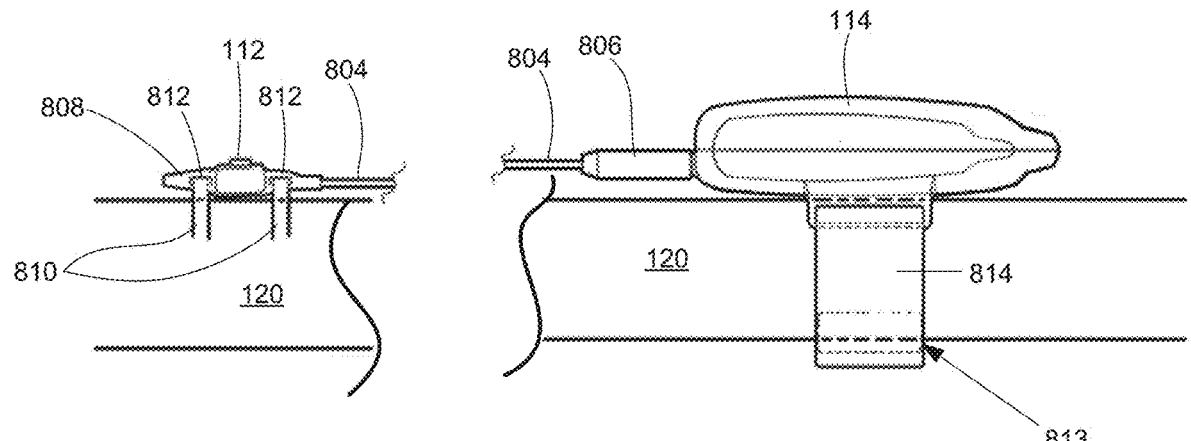
FIG. 10 is a side elevational view of a switch and transmitter that can be used to control the fluid control unit.
Figure 11:
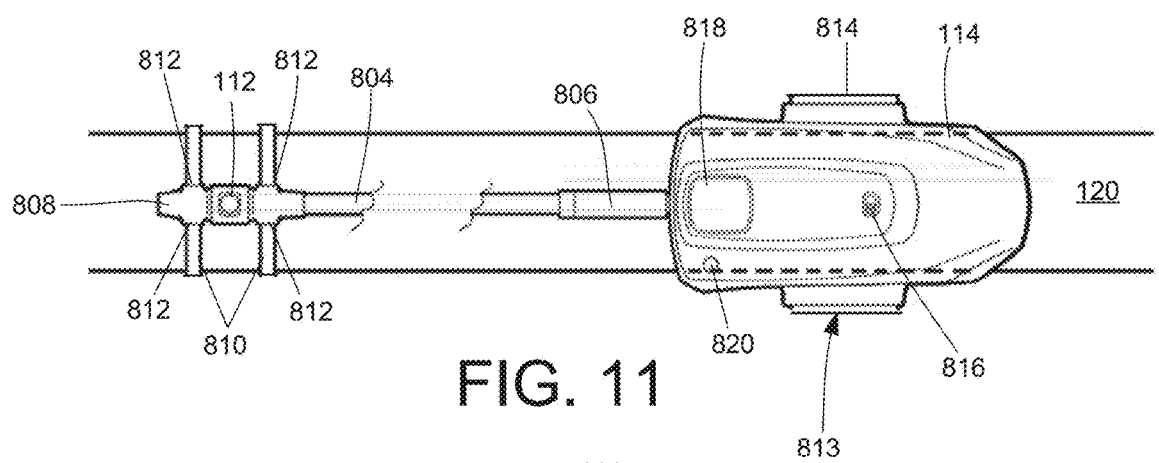
FIG. 11 is a top view of a switch and transmitter that can be used to control the fluid control unit.

As best seen in FIGS. 1, 10 and 11, a cable 804 electrically couples the microswitch 112 to the transmitter 114 to form wireless actuation system 140. Cable 804 in the illustrated embodiment is electrically connected to the microswitch 112 at one end and includes an electrical connector 806, such as a conventional tip sleeve mini jack or cable jack, at a second end for selectively electrically coupling the microswitch 112 to the transmitter 114 via a mating electrical connector (such as a mating socket connector) provided in one end of the transmitter 114. The mating electrical connector provided on one end of the wireless transmitter 114 removably receives the electrical connector 806.

In other embodiments, switch 112 and transmitter 114 may be operably connected in another suitable way.

The wireless transmitter 114 is preferably in the form of a FOB and may, for example, be a Bluetooth transmitter, and more preferably a Bluetooth Low Energy ("BLE") transmitter.

In some embodiments, the wireless transmitter 114 is configured to transmit a first signal when the connector 806 is connected to the mating electrical connector of the wireless transmitter 114 and the microswitch 112 is closed. Preferably microswitch 112 is a normally open switch so that it is closed when the user 90 depresses the button of the microswitch 112 and is open when the user releases the button of the microswitch 112. The first signal may, for example, instruct controller 428 to send power to the pump/motor assembly 306 in order to pump fluids from the fluid reservoir 104 through the fluid delivery system 103 to the user 90. The wireless transmitter 114 may also be configured to transmit a second signal when the connector 806 is connected to the mating connector of the wireless transmitter 114 and the microswitch is open. The second signal may, for example, instruct controller 428 to not send power to the pump/motor assembly 306. When controller 428 receives the second signal it will stop sending power to pump 306 if it was previously sending power to pump 306, thereby stopping the pumping of fluids from the fluid delivery system 103 to the user 90. On the other hand, if controller 428 had previously received the second signal, such that it had already stopped sending power to pump 306, then the controller 428 will simply continue to not send power to pump 306. Then when the first signal is again transmitted to the controller 428 from the wireless transmitter 114, the controller will again send power to the pump/motor assembly 306 so that it again begins to pump fluids from the reservoir 104 through the fluid delivery system to the user 90. In this way, the user 90 can control the delivery of fluid from the fluid reservoir 104 on demand by simply pressing and releasing microswitch 112.

Controller 428 may be configured to provide fluids as long as the user 90 is pressing the microswitch 90, or, alternatively, it may be configured to provide a defined aliquot of fluids each time the controller 428 receives the first command signal (e.g., when the user 90 presses the microswitch 112, regardless of how long the user holds down the microswitch). The aliquot, for example, may be a squirt of a certain duration or volume.

Importantly, in the illustrated embodiment, the user 90 can press and release the microswitch 90 without ever having to remove his or her hand from the handle bar 120, so that regardless of how fast the user 90 is traveling on bicycle 93 or the difficulty of the terrain being traversed, the user 90 is able to instruct the hydration system 100 to deliver the hydration fluid contained within fluid reservoir 104 as desired while maintaining both hands on the handlebar 120 and steering the bicycle 93. Further, with the aliquot or dose implementation described above, the user 90 is not required to hold the button down as long as may be required to deliver the desired aliquot.

In view of the fact that user 90 can safely and conveniently operate microswitch 112 while riding bicycle 90 under any conditions, it is much more likely that the user 90 will drink fluids from reservoir 104 more regularly, thereby allowing the user 90 to remain hydrated during his or her bicycle ride, race, etc.

The microswitch 112 may be mounted to the handle bar 120 using a first mounting means 810, 808 provided proximate the microswitch 112. The wireless transmitter 114 may include a second mounting means 813 attached thereto for removably attaching the wireless transmitter 114 to the handle bar 120.

Figure 12:
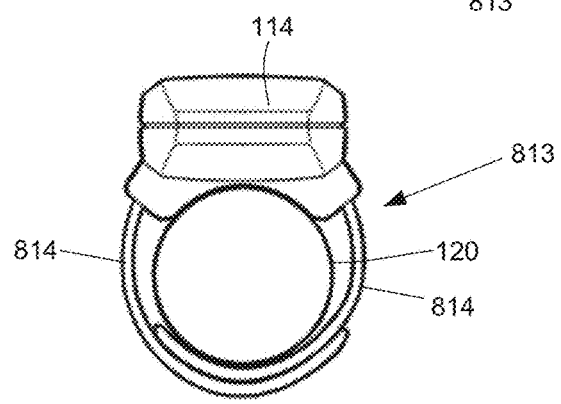
FIG. 12 is an end view of a transmitter attached to a handlebar of a bicycle.

In the embodiment illustrated in FIGS. 1, 10, and 11, the first mounting means comprises a pair of cable ties 810 and an elongated piece of heat shrink tubing 808. The heat shrink tubing 808 is disposed axially around the microswitch 112 and a portion of the cable 804 and fixed in place by heat shrinking it. As best seen in FIG. 12, heat shrink tubing 808 includes a hole for the actuation button of microswitch 112 to extend through. In addition, the heat shrink tubing 808 includes two pairs of slits 812 on opposite sides of the microswitch 112. Each pair of slits 812 extends in an axial direction of the heat shrink tubing 808. Further, a cable tie 810 extends through each one of the pairs of slits 812. The cable ties 810 can then be used to attach the microswitch 112 in an appropriate location on the steering mechanism 122 of vehicle 92, for example, the handlebar 120 of bicycle 93, as described above.

In other embodiments, the first mounting means may comprise other suitable structures for mounting microswitch 112 in the desired location. In addition to the illustrated cable ties, suitable mounting structures may include, for example, brackets, fasteners, hook and loop fasteners, and clips, as well as a combination of the above.

In the embodiment illustrated in FIGS. 1, 10-12, the second mounting means 813 comprises a pair of straps 814 each strap being attached to opposite sides of the wireless transmitter 114 at one end, and the other end of each of the straps 814 comprises a hook and a loop fastener, respectively, with each being disposed on opposing sides of straps 814. Referring to FIG. 12, the straps 814 of the second mounting means 813 are of a sufficient length so that they may wrap around handlebar 120 of steering mechanism 122 and so that the opposing hook and loop fasteners provided on the respective ends of the straps 814 will overlap with one another so as to securely hold the wireless transmitter 114 to the handlebar 120 when they are fastened together. As a result, the wireless transmitter 114 may be removably attached to the handlebar 120 of steering mechanism 122 in a location sufficiently proximate the microswitch 112 so that the connector 804 on the end of cable 804 can be removably connected to the mating connector provided on one end of the wireless transmitter 114.

The wireless transmitter 114 preferably includes an on/off switch 816. The wireless transmitter 114 may also comprise an indicator light 820. The indicator light 820 may be configured to signal a variety of states. For example, indicator light 820 may signal that the wireless transmitter 114 is powered on. The indicator light 820 may also be configured to signal when wireless transmitter 114 of the wireless actuation system 140 is paired with controller 428 of fluid control unit 106. In addition, the indicator light 820 may be configured, for example, to signal when a signal, such as the first signal, is being transmitted from the wireless transmitter 114.

The wireless transmitter 114 of FIGS. 1, 10-12 has a single button 818. The wireless transmitter 114 may thus also be configured to transmit the first signal when the button 818 is depressed, regardless of whether the connector 806 is connected or not. Moreover, the transmitter 114 may also be configured to transmit the second signal when the button 818 is not depressed, either when the connector 806 is connected to the mating connector and the microswitch 112 is open or when the connector 806 is not connected to the mating connector.

In other embodiments, a wireless transmitter may be employed that has additional buttons. For example, the wireless transmitter 860 shown in FIGS. 14 and 15 has two buttons, a first button 862 and a second button 864. Another illustrative embodiment of a wireless transmitter is shown in FIGS. 18-21. The wireless transmitter 880 shown in FIGS. 18-21 is a three button wireless transmitter, with a first button 862, a second button 864, and a third button 882. Both transmitters 860 and 880 are preferably a FOB Bluetooth transmitter, more preferably a FOB BLE transmitter, like wireless transmitter 114. The microswitch 112 may electrically connect to transmitters 860 and 880 in the same manner using cable 804 and connector 806, which is removably received within a mating connector provided in one end of each of transmitters 860 and 880. Furthermore, the transmitters 860 and 880 are preferably configured to work in the same manner with microswitch 112 as described above with respect to transmitter 114.

By employing a transmitter with additional buttons, the FOB transmitter may be configured to transmit additional signals, beyond the first and second signals produced by transmitter 114, when one of additional buttons is depressed.

For example, transmitter 860 may be configured so that when (i) the connector 806 is connected to the mating connector provided in the end of transmitter 860 and the microswitch 112 is open or (ii) when the connector 804 is disconnected from the mating connector in the end of transmitter 860, the wireless transmitter 860 will transmit the first signal when the first button 862 is depressed, the second signal when neither the first button 862 or second button 864 is depressed, and a third signal when the second button 864 is depressed.

The three button transmitter 880 may be configured so that (i) when the connector 806 is connected to the mating connector provided in the end of transmitter 880 and the microswitch 112 is open or (ii) when the connector 806 is disconnected from the mating connector provided in the end of transmitter 880, the wireless transmitter 880 transmits the first signal when the first button 862 is depressed, the second signal when none of the first button 862, second button 864, or third button 882 are depressed, the third signal when the second button 864 is depressed, and a fourth signal when the third button 882 is depressed.

Although in the above description, the depression of each button of a transmitter is used to generate one control signal, it should also be appreciated that the various transmitters may be configured so that the depression of one or more of the transmitter buttons will generate multiple control signals based on the duration of how long a particular button is depressed. For example, transmitter 880 may be configured so as to generate the fourth signal when the third button 882 is depressed for more than 1 second, but less than 2 seconds and a fifth signal when it is depressed for 2 seconds or more. Alternatively, the transmitter may be configured so that one or more of the transmitter buttons generate multiple control signals based on how a particular button is depressed. For example, transmitter 880 may be configured so as to generate a fourth signal when the third button 882 is depressed for more than 1 second, and so as to generate a fifth signal when it is depressed for less than one second and then depressed again within 1 second. If desired, a button may be configured to generate control signals based both on how long it is depressed and how it is depressed. For example, transmitter 880 may be configured so as to generate a fourth signal when the third button 882 is depressed for more than 1 second, and a fifth signal may be generated when it is depressed for less than one second and then depressed again within 1 second for 2 seconds or more.

As discussed above with respect to microswitch 112, the first signal may, for example, instruct controller 428 to send power to the pump/motor assembly 306 in order to pump fluids from the fluid reservoir 104 through the fluid delivery system 103 to the user 90. The second signal may, for example, instruct controller 428 to not send power to the pump/motor assembly 306. The third signal may, for example, instruct controller 428 to send power with reverse polarity to pump/motor assembly 306 in order to drive it in the reverse direction. The fourth signal may, for example, instruct controller 428 to enter a stand by or pause mode. The fifth signal may, for example, be a resume command that instructs controller 428 to resume normal operation in response to the receipt of first, second, and/or third signals.

Because the second mounting means 813 releasably attaches the wireless transmitter 114 (or 860 or 880 in other embodiments) to the steering mechanism 122 of a vehicle 92, such as bicycle 93, after finishing his or her activity with vehicle 93, the user 90 can detach the FOB transmitter and take it with him or her. In this way, the user can continue to use the FOB transmitter (e.g., 114, 860, or 880) to control the controller 428 of fluid delivery system 103 even when not using a vehicle 92. Furthermore, the second mounting means 813 may be used to attach the wireless transmitter to the shoulder strap 212 so that it is readily accessible by the user.

Figure 15:
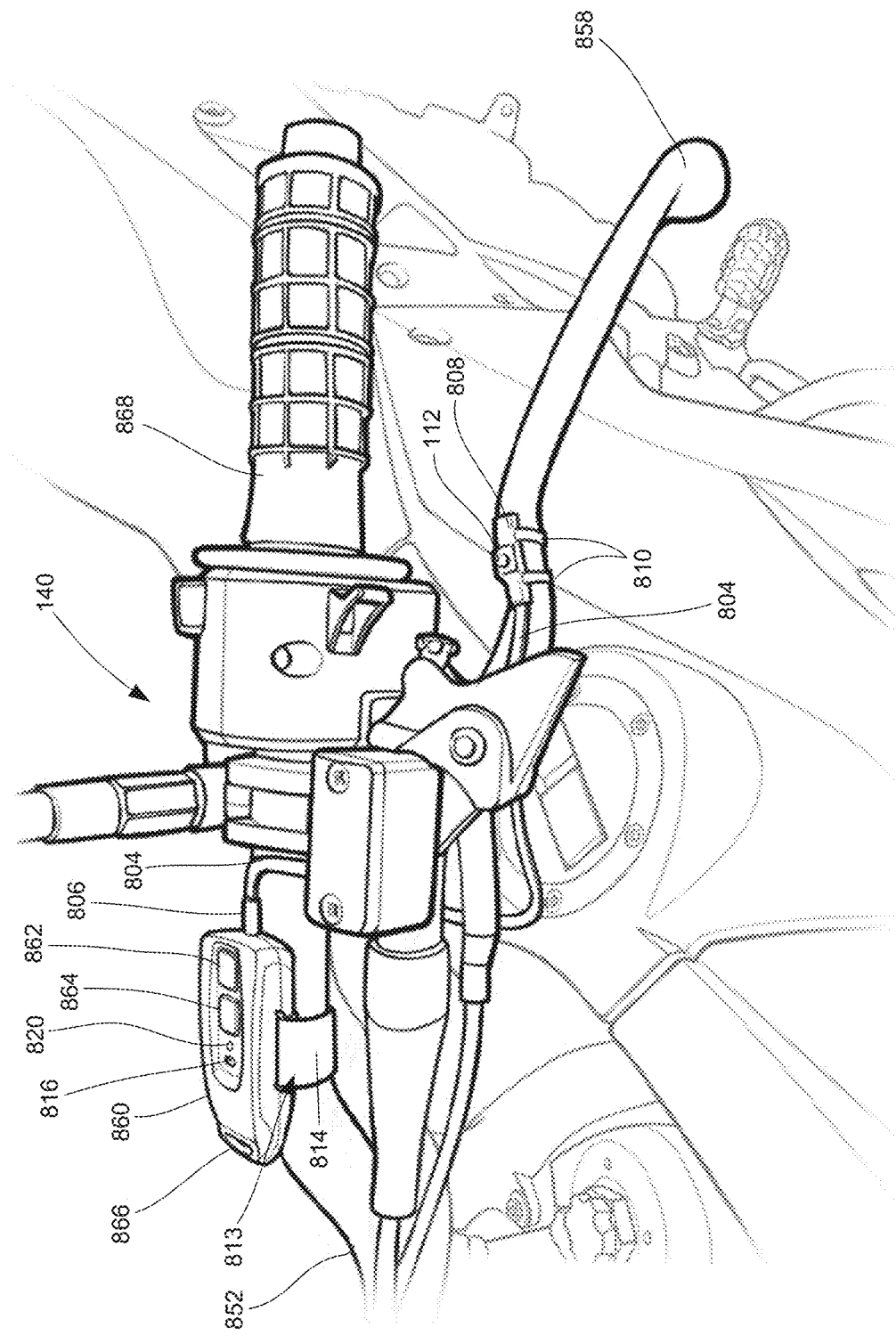
FIG. 15 is a close up view of the left hand side of the handlebar of the motorcycle of FIG. 13.
Figure 19:
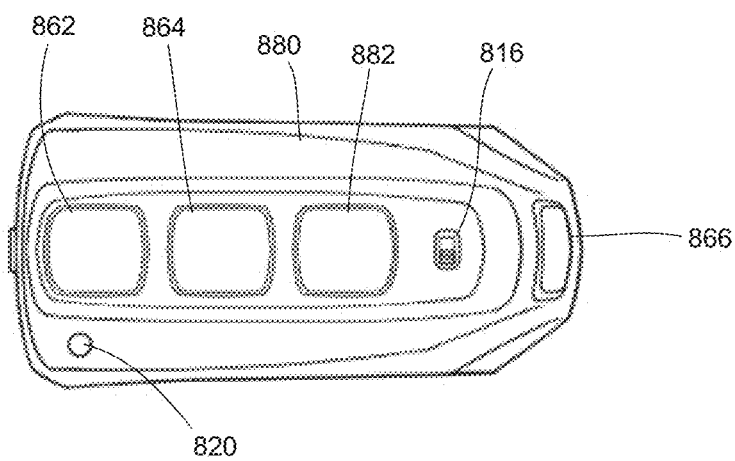
FIG. 19 is a top view of the transmitter of FIG. 18.
Figure 20:
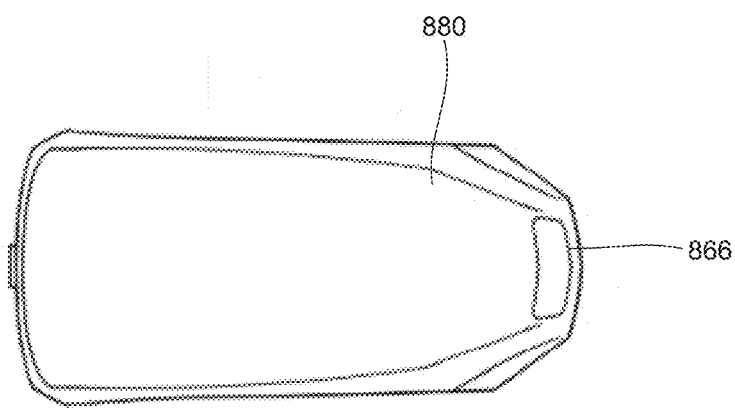
FIG. 20 is a bottom view of the transmitter of FIG. 18.

Alternatively, as best seen in FIGS. 15, 19, and 20, the wireless transmitter may be provided with a keychain loop 866. Keychain loop 866 may be used to attach the wireless transmitter to backpack 102 using, for example, a key chain ring. For example, keychain loop 866 may be used to attach a FOB transmitter to one of the shoulder straps 212, so that it is readily accessible by user 90 to control the fluid delivery system 103 even when engaging in an activity that does not involve a vehicle 92. And while a key chain loop is included in wireless transmitter 860 shown in FIG. 15 and wireless transmitter 880 shown in FIGS. 19 and 20, the key chain loop 866 may also be included in other wireless transmitters, including transmitter 114, that may be used to control the fluid control unit 106 of the present patent document.

The fluid delivery system 103 shown in FIGS. 1 and 2 may also include multiple wireless transmitters. For example, one wireless transmitter 114 may be removably attached to the steering mechanism 122 of vehicle 92 as shown in FIG. 1 and another may be attached to a shoulder strap 212 of backpack 102 so that the user 90 does not need to remove the wireless transmitter from the steering mechanism 122.

Fluid Control Unit

The fluid control unit 106 of the illustrated embodiment is now described in greater detail in connection with FIGS. 3-6.

The fluid control unit 106 may comprise a housing 204, a pump 306 disposed within the housing, a controller 428 operably connected to the pump to control the pump 306, a power source, such as battery 423, is in electrical communication with the pump 306 via the controller 428.

Controller 428 is operably configured to respond to one or more commands signals received from a wireless transmitter, such as wireless transmitter 114, that is in wireless communication with the controller 428. An inlet of the pump 306 is in fluid communication with a first coupling member of a first mechanical quick connect and an outlet of the pump is in fluid communication with a second coupling member of a second mechanical quick connect. For example, in some embodiments, an inlet tube 310 may be connected to the inlet of the pump 306 at one end and a hose connector, such as a barbed hose connector 320, of inlet male quick connector 314 at the other end. Further, an outlet tube 312 may be connected to the outlet of the pump 306 at one end and a hose connector, such as barbed hose connector 324, of an outlet female quick connector 322 on the other end.

While controller 428 may be configured to communicate with wireless transmitter 114, it may also be configured to communicate with a host of other wireless transmitters, including, for example, wireless transmitters 860 and 880. As described above, each of these wireless transmitters may be configured to communicate one or more command signals in response to one or more inputs, respectively.

Controller 428 may include a wireless transceiver to establish a wireless communication link with the wireless transmitters used to send command signals to the controller. Preferably the wireless transceiver included in controller 428 is a Bluetooth transceiver, and more preferably a Bluetooth Low Energy ("BLE") transceiver. Although controller 428 may include the wireless transceiver, the wireless transceiver may also be provided as a separate component on circuit board 408 that is in turn operably connected to controller 428.

Housing 204 should generally be sized to be small enough to fit within backpack 102 while being large enough to house pump 306, circuit board 408, and battery 423, as well as the associated electrical wiring, fluid circuitry to route fluids from the fluid inlet of the housing 204 to the fluid outlet for the housing 204, and related structural components. The fluid inlet for housing 204 is provided by connector 314 while the fluid outlet for housing 204 is provided by connector 322.

While housing 204 is disc shaped in the illustrated embodiment, housing 204 may comprise other shapes. One advantage of employing a housing 204 that is generally disc shaped is that it will not have any sharp edges or corners that may puncture a fluid reservoir 104 or potentially injure user a user during use. For example, a housing 204 with corners or sharp edges could potentially injure a user 90 in the event of a crash he or she otherwise falls on backpack 102 while it contains control unit 106.

Housing 204 may comprise multiple pieces. For example, in the illustrated embodiment, housing 204 includes a back housing cover 302, a front housing cover 350, and a battery or power source cover 206. In other embodiments, housing 204 may comprise fewer or more pieces. Housing 204 may be made out of any suitable material. Plastic will be suitable in most applications. Further, the various housing pieces may be manufactured using any suitable technique, including injection molding and 3D printing.

As explained more fully below, battery source power cover 206, back housing cover 302, front housing cover 350 may include a variety of features to facilitate the positioning of the items that are to be contained within the housing 204.

Controller 428, for example, is provided on a circuit board 408 that is disposed within housing 204. In the illustrated embodiment, circuit board 408 is supported on a circuit board mount 410 that is attached to an interior side of back housing cover 302. Circuit board mount 410 may include legs 412 for attaching the circuit board mount to the back housing cover 302. Brackets 332 may be provided on the interior surface of the back housing cover 302 to facilitate the positioning of where legs 412 are attached to cover 302.

The back and front cover housings may also include mounting brackets 308, 352, respectively for positioning the pump 306 in a side-to-side or horizontal direction within housing 204. Further, a motor stop 356 may be provided in the front housing cover 350 to position the motor 306 in the vertical direction within housing 204. Motor stop 356 includes a main body 358 and a spacer 360. Spacer 360 spaces the bottom of motor 306 off the main body 358 of the motor stop 356 by a predetermined distance so as to provide a space for motor terminals 417 between the motor and the main body 358 of the motor stop.

Figure 3A:
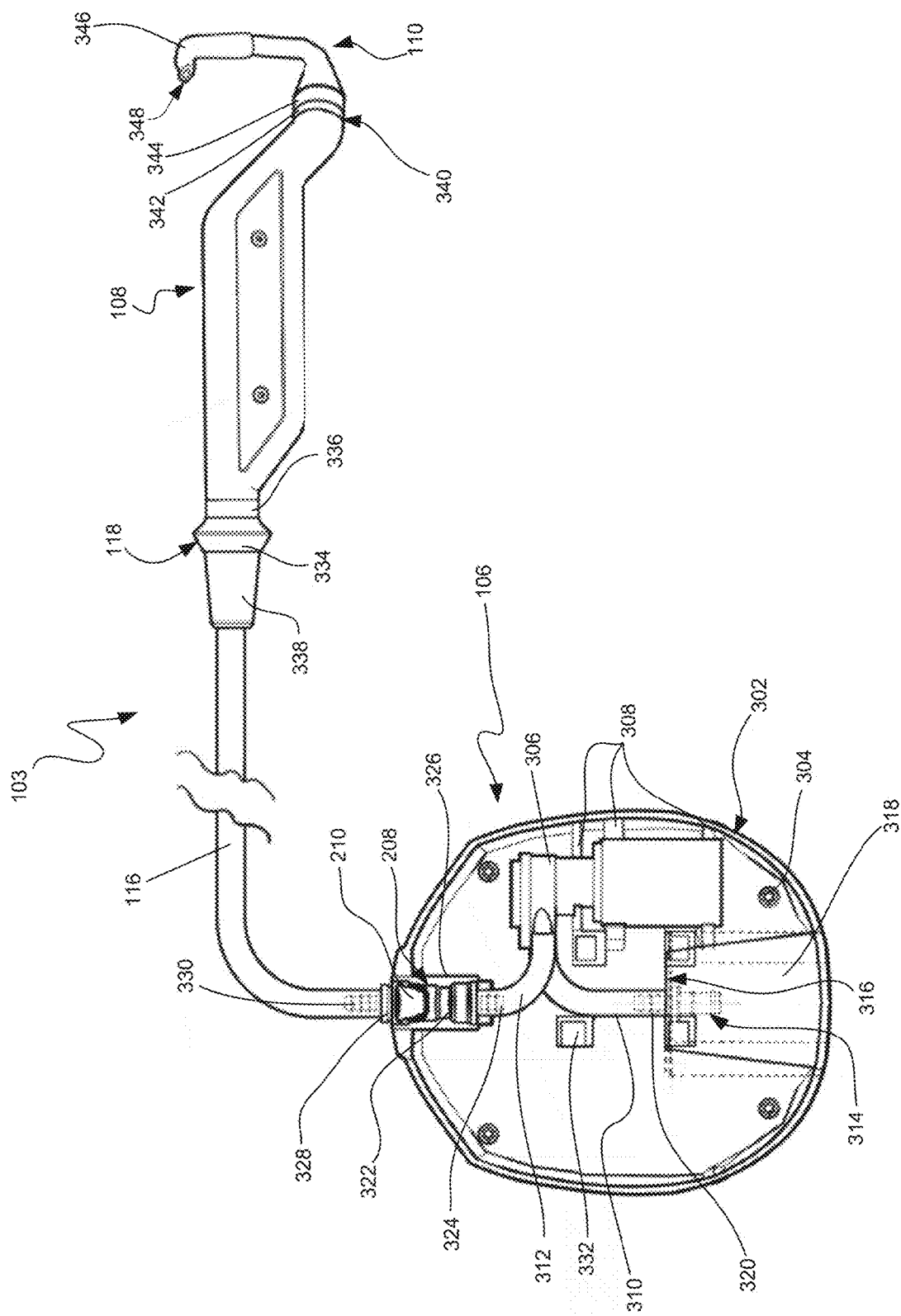
FIG. 3A is a schematic illustration of a fluid delivery system of FIG. 1 with the front housing cover removed from the fluid control unit.

Front housing cover 350 includes a matching recess 368 for receiving female quick connector 322 at an upper end. Matching recess 368 substantially matches the outer profile of female quick connector 322. In addition, a cutout 370 is provided at the top of recess 368 so that when female quick connector 322 is seated in recess 368, the release button 210 will extend therethrough as best seen in FIGS. 2 and 3A so that it may be pressed from outside housing 204 to release male quick connector 328 from female quick connector 322. Further, a hose recess 372 is provided at the bottom of recess 368 for outlet tube 312 and hose connector 324 to extend through into housing 204.

The opposite side of female quick connector 322 is received within a recess 434 provided in a support 326. Recess 434 is configured to match the other outer profile of the other side of female quick connector 322 so that connector 322 will seat therein.

The back surface 407 of support 326 is flat and disposed adjacent support boss 430, which is also flat, when back housing 302 is attached to front housing 350. This results in the female quick connector 322 being sandwiched between support 326 and front housing cover 350 in recesses 434 and 368, respectively, with release button 210 extending through front housing cover 350.

Figure 4A:
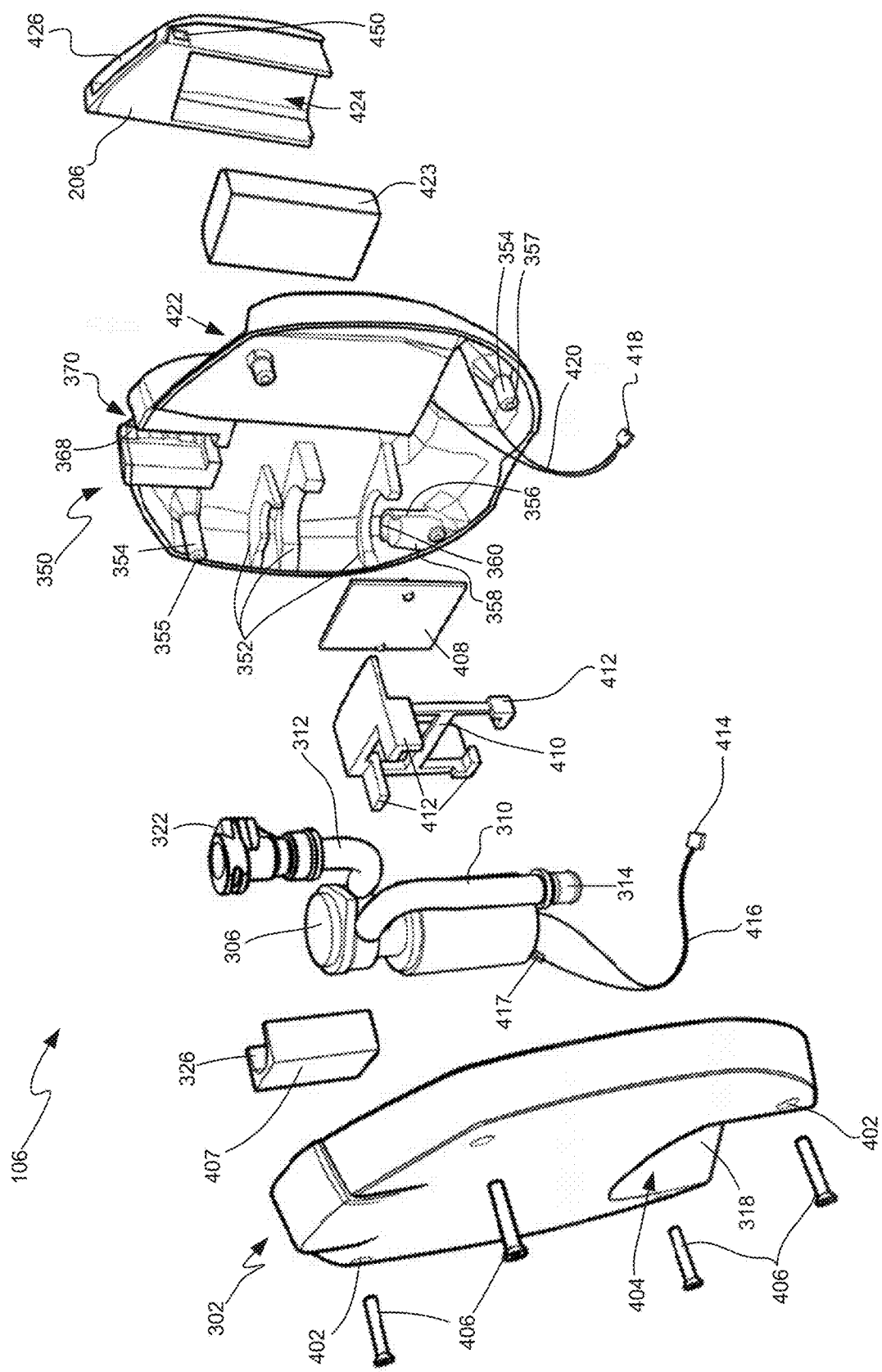
FIG. 4A is a rear exploded isometric view of a fluid control unit.
Figure 4B:
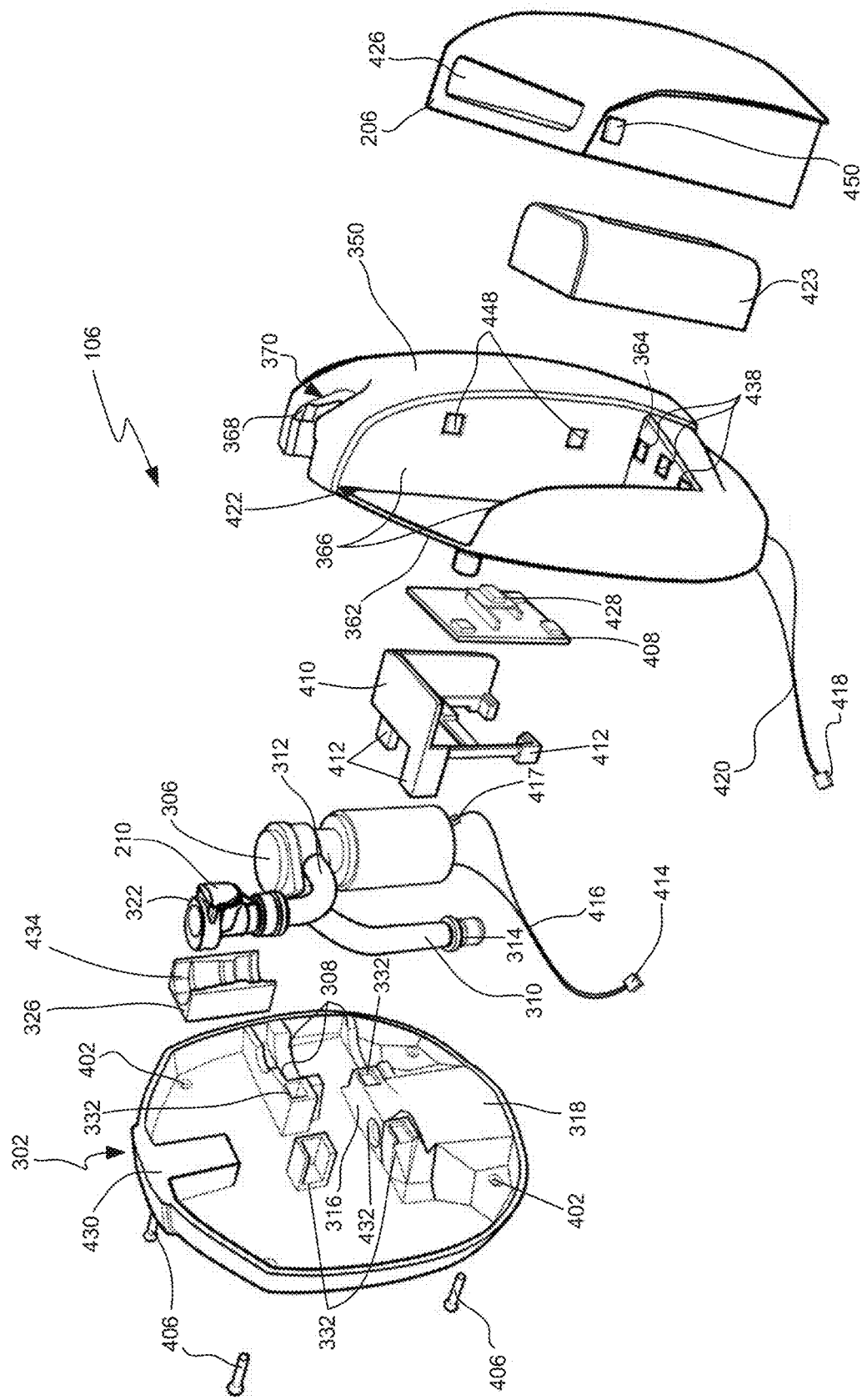
FIG. 4B is a front exploded isometric view of a fluid control unit.

Back housing cover 302 may be attached to front housing cover 350 using any suitable fastener or attachment technique. For example, as illustrated in FIGS. 4A and 4B, the two covers may be attached using screw fasteners 406. Each screw 406 extends through a corresponding hole 402 extending through back housing cover 302 and attaches to a corresponding threaded hole 355 provided on the interior surface of front housing cover 350. Preferably each threaded hole 355 is provided in a mating end 357 of a support stand off 354. In this way, the housing covers 302, 350 will be more resistant to collapse or damage due to the overtightening of screws 406. Each mating end 357 of a support standoff 354 may engage with a corresponding recess area 304 provided on the interior surface of back housing cover 302.

In the illustrated embodiment, there are four screws 406, four holes 402 in back housing cover 402 for them to extend through, and four standoffs 354 each with a threaded hole 355 provided in its mating end 357 for a screw 406 to engage with. In other embodiments, however, more or fewer fasteners may be employed. Because four screw fasteners 406 are employed with four corresponding standoffs, four recessed areas 304 are provided on the interior of back housing cover 302. One for each mating end 357 of each support standoff to be positioned in as screw fasteners 406 are tightened.

In other approaches, back housing cover 302 may be adhesively bonded to front housing cover 350 or, depending on the material used to make the housing covers, welded to one another. Attachment techniques that may be more permanent in nature, however, may be less desirable to the extent it is desirable to be able to access the contents of housing 204.

Power source cover 206 is configured to fit within a battery compartment 422 formed in the front housing cover 350. Cover 206 is formed so that when it is received (with or without battery 423) within recess 422 the exterior walls of the cover 406 generally follow the exterior contour lines of the front housing cover 350.

The power source cover 206 may include an indent 426 on its exterior surface. Indent 426 is preferably sized to receive a user's finger or fingers and thereby facilitate the separation of cover 206 from front housing cover 350.

Figure 5:
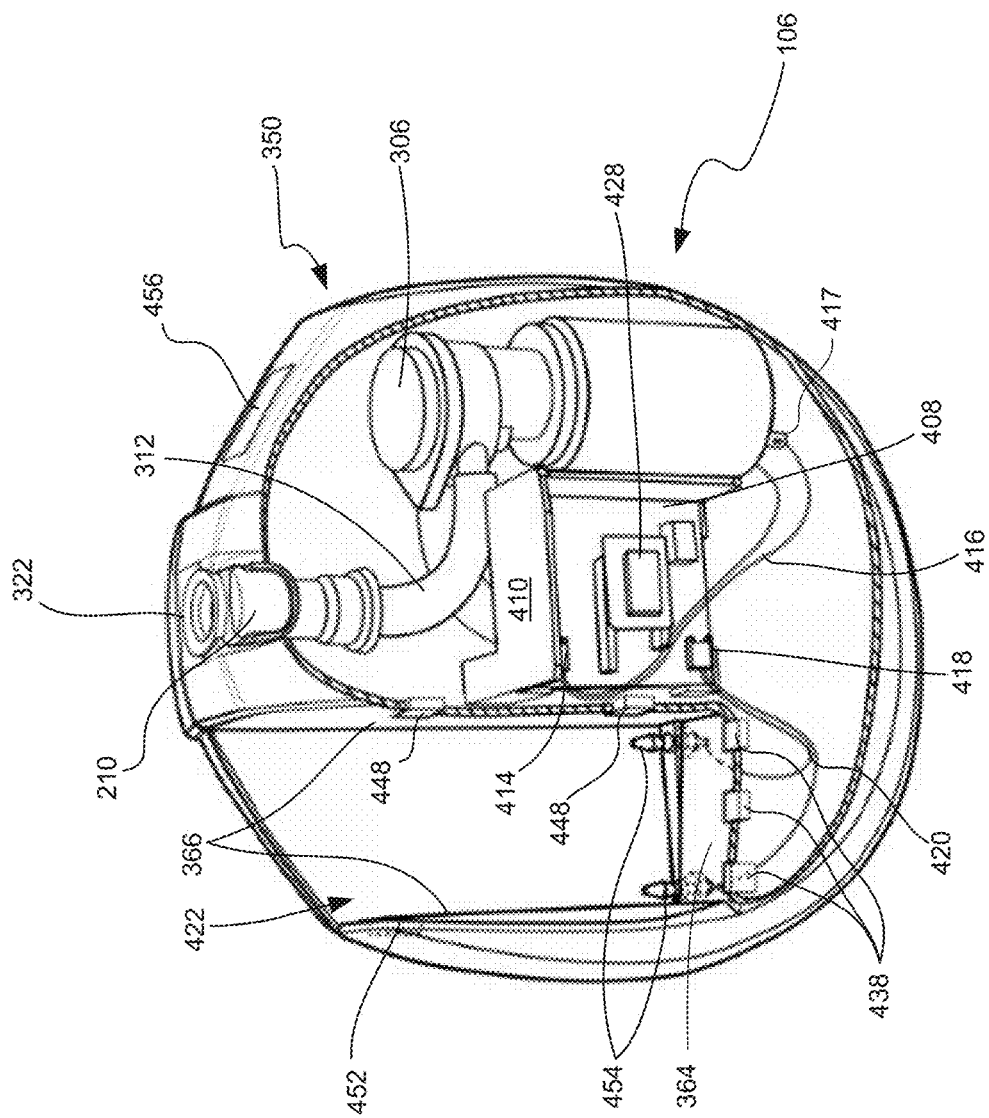
FIG. 5 is a fluid control unit with its front hosing cover partially cut-away and the battery and power source cover removed.

Battery compartment 422 is formed by an inwardly recessed wall 362, bottom wall 364, and side walls 366, all of which are provided in front housing cover 350. Power source cover 206 includes a recess 424 that is formed on a backside thereof for receiving battery 423. Recess 424 of cover 206 is preferably configured so that battery 423 may only be inserted in an operable orientation. Further, as best seen in FIGS. 5 and 6C, recess 424 is also preferably configured so that when battery 423 is inserted therein and the cover 206 is inserted into battery compartment 422, the battery contacts 454 that extend through the bottom wall 364 align with and make electrical contact with battery terminals 460 that are provided on battery 423.

Figure 6B:
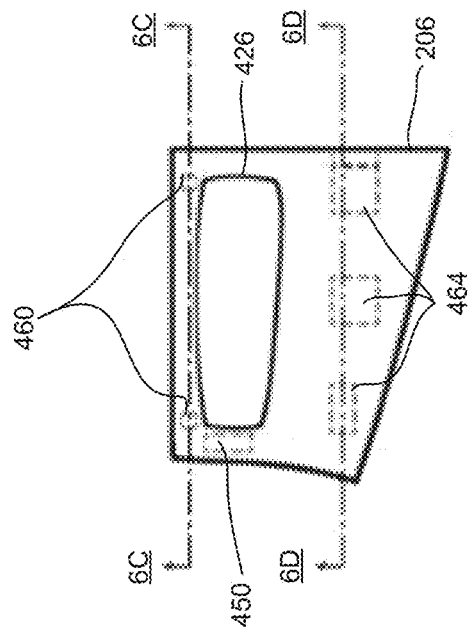
FIG. 6B is a top plan view of the power source cover of FIG. 6A.
Figure 6A:
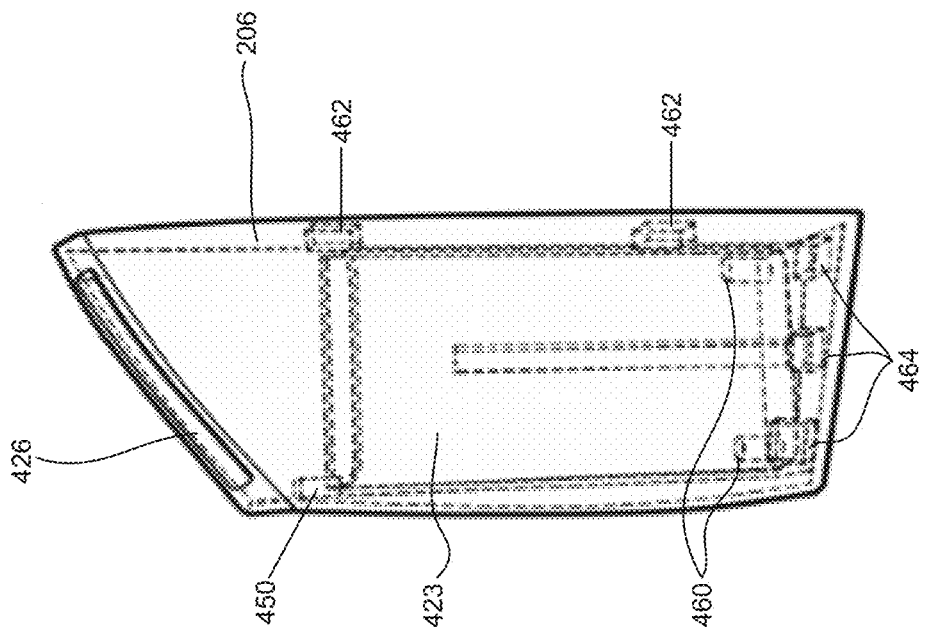
FIG. 6A is a front elevation view of a power source cover and battery.
Figure 6D:
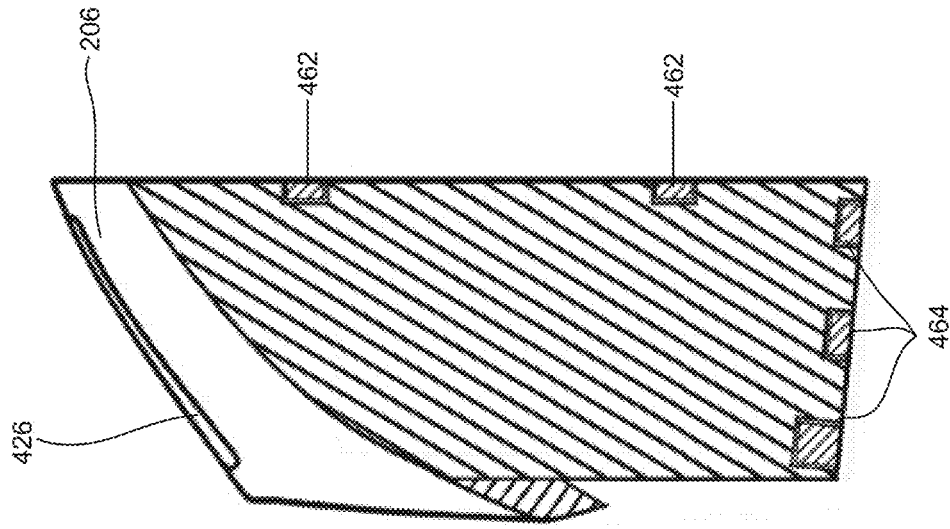
FIG. 6D is a cross-sectional view of the power source cover shown in FIG. 6B taken along the line 6D-6D.
Figure 6C:
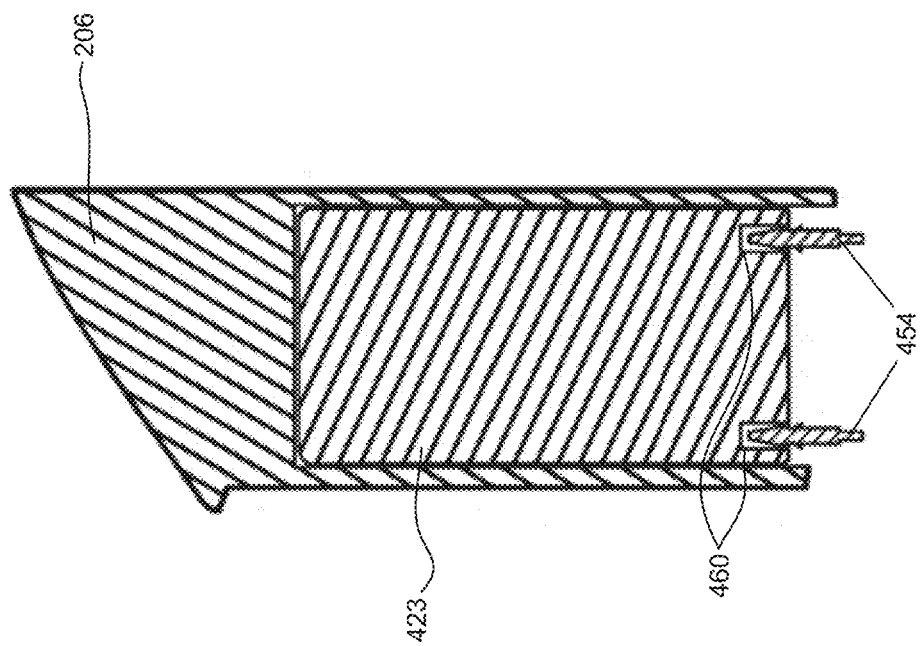
FIG. 6C is a cross sectional view of the power source cover shown in FIG. 6B taken along the line 6C-6C.

FIG. 6C is a sectioned view through cover 206 and battery 423 taken along cut-line 6C-6C. As shown in FIG. 6C, battery contacts 454 are actually received within battery terminals 460 when battery 423 is received in recess 424 and cover 206 is inserted into battery compartment 422.

Power source cover 206 may be held in place by a clip or other suitable fastener. In the illustrated embodiment, cover 206 is magnetically held in place within battery compartment 422. For example, permanent magnets 450 and 462 are provided in recesses provided in opposing side walls of cover 206 and magnets 464 are provided within recesses provided in a bottom wall of cover 206. In the illustrated embodiment, a single magnet 450 is provided on one sidewall of cover 206, while two magnets 462 are provided on the other sidewall of cover 206, and three magnets 464 are provided in the bottom wall of cover 206. In other embodiments, a different arrangement of magnets may be used.

Corresponding permanent magnets are provided in front cover 350. In the present embodiment, a magnet 452 is provided in one sidewall 366 of battery compartment 422, two magnets 448 are provided in the other sidewall 366, and three magnets 438 are provided in the bottom wall 364 of battery compartment 422. Magnet 452 is positioned in one sidewall 366 so that it will be opposite magnet 450 when cover 206 is inserted within battery compartment 422. Magnets 448 are each positioned within the other sidewall 366 so that each one will be opposite one of the magnets 462 provided in the opposing sidewall of cover 266 when cover 206 is inserted within battery compartment 422. Further, magnets 464 are each located within the bottom wall 364 so that each one it will be opposite one of the magnets 438 when cover 206 is inserted in place.

Magnets 450, 462, and 464 may be adhesively set within the recesses provided in the walls of cover 206. Likewise, the magnets 438, 448, and 452 may be adhesively set within recesses provided in their respective walls of the battery compartment 422.

Although magnets 450, 462, and 464 in cover 206, and corresponding magnets, 438, 448, and 452 in cover 350 are all permanent magnets in the present embodiment, in other embodiments, a combination of permanent magnets and corresponding pieces of magnetic material may be employed. For example, permanent magnets may be used in one cover, and corresponding pieces of magnetic material (such as a ferromagnetic material) may be used in the other cover.

FIG. 6D is a sectioned view through cover 206 and battery 423 taken along cut-line 6D-6D. As seen best from FIGS. 6B and 6D, magnets 464 and 462 are disposed along the same plane in cover 206, while magnet 250 is disposed on a different plane. This is due to the fact that the rounded nature of the housing 204 (and thus cover 206) prevents magnet 450 from being located behind battery 423, whereas magnets 462 and 464 may be located behind battery 423 within cover 206.

Back housing cover 302 may include a recess 404. Recess 404 extends from a bottom wall of the back housing cover 302 to a mounting wall 316 and is defined by inwardly recessed wall 318 and mounting wall 316. As best seen in FIGS. 3A and 4A, inwardly recessed wall 318 gradually slopes inwardly along its sides from a main planar exterior surface of back housing cover 302. On the other hand, mounting wall 316 is generally perpendicular to the main planar exterior surface of back housing cover 302 and extends inwardly towards and meets with inwardly recessed wall 318 at an upper end of the latter. Mounting wall 316 forms a support wall that extends horizontally across the back of back housing cover 302.

A portion of the inlet male quick connector 314 extends through a hole 432 provided in the mounting wall 316. For example, in some designs, a hose connector, such as barbed hose connector 320, provided at one end of the male quick connector 314 may extend through the hole 432 in mounting wall 316 so that a connector portion of the male quick connector 314 is disposed on the exterior of the housing 204 and the hose connector 320 of the male quick connector 314 is disposed on the inside of the housing 204 and the inlet tube 310 may be connected thereto. The recess 404 is preferably sized to receive an outlet spout of a hydration reservoir bag that may be used for fluid reservoir 104. Frequently the outlet spouts of conventional hydration reservoir bags include a mating female mechanical quick connector disposed at the end of the outlet spout (not shown). The recess 404 is also preferably sized so as to permit a user to access a release, similar to quick connect release 210, on the mating female quick connector when the male quick connector 314 and mating female connector on the outlet spout of the hydration bag are connected. In this way, a user may uncouple fluid control unit 106 from the outlet spout of fluid reservoir 104 once it has been coupled. Moreover, with this design, the fluid control unit 106 may lie flat against a conventional fluid reservoir bag 104, such as a CAMELBAK™ reservoir bag, and still fit within a conventional hydration backpack 102.

Power is provided from battery 423 to controller 420 via wires 420 and connector 418. One of each of the wires 420 is connected at one end to one of the battery contacts 454 and at the other end to connector 418. Connector 418 in turn connects to a corresponding female connector provided on circuit board 408. As a result, when battery 423 is installed within battery compartment 422, current may flow from the positive battery terminal through the corresponding battery contact 454 and wire 418 to circuit board 408 where it is subjected to a load. The battery circuit is completed by the other wire 418 which allows current to flow back to the negative battery terminal through the other battery contact 454.

Circuitry provided on circuit board 408 operably connects controller 428 to the power provided by wires 420 from battery 423. Controller 428 in turn operably connects power to pump 306 via circuitry provided on circuit board 408, connector 414, and wires 416.

In the illustrated embodiment, one of each of the wires 416 is connected to one of the terminals 417 of pump 306. When controller 428 receives a command signal from a wireless transmitter (e.g., transmitter 114, 860 or 880) to send power to the pump/motor assembly 306 in order to pump fluids from the fluid reservoir 104 through the fluid delivery system 103 to the user 90, the controller will send current through wires 416 to pump 306 in a forward polarity direction. On the other hand, when controller 428 receives a command signal instructing controller 428 to not send power to the pump/motor assembly 306, then controller 428 will stop sending current through wires 416 to pump 306. In response to a command signal instructing controller 428 to send power with reverse polarity to pump/motor assembly 306 in order to drive it in the reverse direction, then controller 428 will send current through wires 416 to pump 306 in a reverse polarity direction, thereby causing the pump to pump in the reverse direction. In response to a command signal instructing controller 428 to enter a standby or pause mode, then controller 428 will not respond to any further commands until it is instructed to exit that mode. For example, controller 428 may not respond to any further command signals until the controller 428 receives a resume command from a wireless transmitter that instructs controller 428 to resume normal operation in response to the receipt of first, second, and/or third command signals discussed above.

As noted above, controller 428 may be programed to immediately stop sending power when receiving the stop command, or it can be programmed to only stop sending power after a defined aliquot or dose of water has been delivered to the user 90. For example, controller 428 may be configured to send power to pump 306 (or provide fluids) as long as the first signal is received (e.g., as long as the user 90 is pressing the microswitch 90). Alternatively, controller 428 may be configured to provide power until the pump delivers a predetermined aliquot of fluids each time the controller 428 receives the first command signal (e.g., each time the user 90 presses the microswitch 112, regardless of how long the user holds down the microswitch). This can be done by configuring the controller to send power for a set period of time after receiving the first signal or until a desired volume is delivered (which may be based, for example, on a number of revolutions of the pump 306 or feedback from a separate flow meter).

Figure 30:
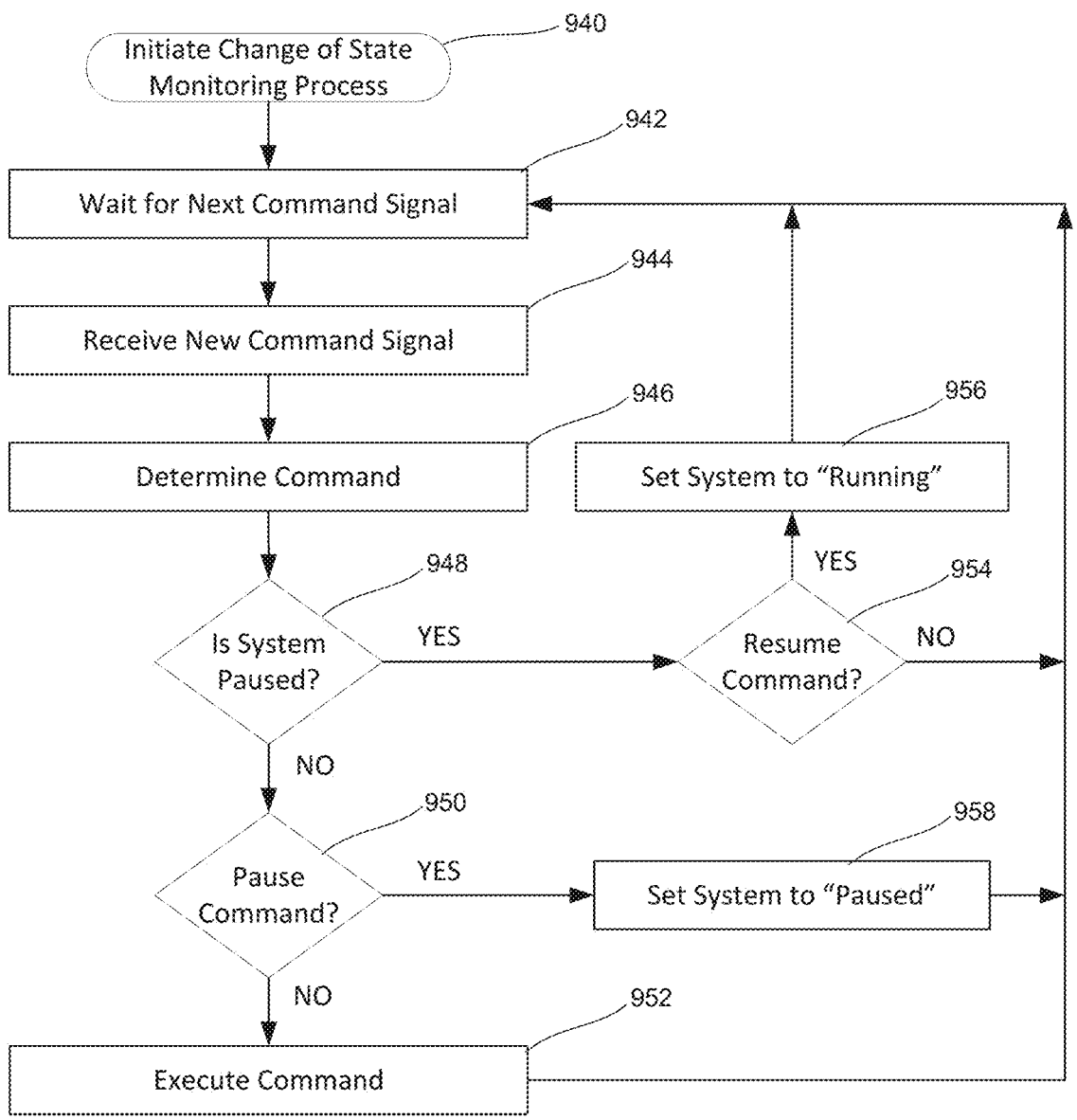
FIG. 30 is a flow diagram illustrating a process for controlling a fluid control unit.

A process flow chart illustrating the operation of controller 428 in response to command signals received from a wireless transmitter is illustrated in FIG. 30.

Initially at step 940, controller 428 is configured to enter a change of state monitoring process. This may occur, for example, when controller 428 is initially powered up and the controller conducts its initialization process. Once the controller initiates the change of state monitoring process, in step 942, controller 428 waits to receive the next command signal. In the BLE protocol, command signals are periodically sent out from the wireless transmitter (e.g. transmitter 114, 860, or 880).

In step 944, controller 428 receives the next command signal from the wireless transmitters. In step 946, controller 428 evaluates and determines the command signal it has received. In step 948, the controller 428 next determines if the system is in a paused condition. If the system is in a paused condition, then in step 954 the controller 428 determines if the command signal is a resume command. If the received signal is a resume command, then in step 956 the controller 428 sets the system to "running" and returns to step 942 to wait for the next command signal. If in step 954 it is determined that the command signal is not a resume command, then controller 428 simply returns to step 954 and waits for the next command signal without taking any further action.

If in step 948 it is determined that the system is not in the paused state, then controller 428 proceeds to step 950 where it evaluates whether the command it received is a "pause command". If the command signal controller 428 received is a pause signal, then in step 958 the controller 428 sets the system to the "Paused" condition and then returns to step 942 where controller 428 awaits the next command signal.

If in step 950 controller 428 determines that the command signal it received is not a "pause command", then controller 428 proceeds to step 952 where it executes the command signal, for example, command signal one, two, or three discussed above. After executing the command signal, controller 428 returns to step 942 where it awaits the next command signal.

In addition to receiving a refill command signal from a wireless transmitter as discussed above, fluid control unit 406 may also be provided with an auto fill or refill button 456. Refill button 456 may extend through the wall of housing 204, such as through the front housing cover 350, as illustrated in FIG. 5 so that it may be depressed by a user. Pressing refill button 456 will cause controller 428 to send current over wires 416 to pump 306 in a reverse polarity direction, thereby causing pump 306 to operate in the reverse direction and pump fluid from the distal end of dispensing hose 116 to the fluid reservoir 104.

The refill feature of the fluid control unit 106 provides a number of advantages, regardless of whether it is activated by a refill command signal from a wireless transmitter or because refill button 456 is depressed. For example, male coupling member 334 of magnetic quick connect 118 may be decoupled from female coupling member 336 as shown in FIG. 7D. Once decoupled, the male coupling member 334, or at least protrusion 722 of male coupling member 334, may be placed in a glass of water or other reservoir and pump 306 will suck the water from the glass or reservoir through the male coupling member 334, dispensing hose 116, fluid control unit 106, and into reservoir 104. As a result, reservoir 104 may be filled (or refilled) without ever removing fill cap 202. As a result, reservoir 104 can be filled with more liquid then it would be able to filled with through the fill opening in reservoir 104 closed by cap 202. Moreover, if two users of hydration system 100 are remote from water sources and one of the users runs low on water or other hydration fluid, the user low on fluid can detach coupling member 334 from headset 108 and then place the end of coupling member 334 into the reservoir 104 of the other user's system to suck water from that user's reservoir. Alternatively, the user with more water in his or her reservoir 104 can simply decouple coupling member 334 from headset 108 as discussed above and then pump water into the reservoir of the other user by removing the fill cap of the other user's hydration reservoir and placing the distal end of his or her dispensing hose 116 adjacent the exposed fill port and activating pump 306 in the forward direction.

Additional refill options that are created by the hydration systems of the present patent document are discussed below in connection with FIG. 29.

Headsets

Various aspects of headset 108 are now described in greater detail in connection with FIGS. 1, 3 and 7A-7F.

Figure 7B:
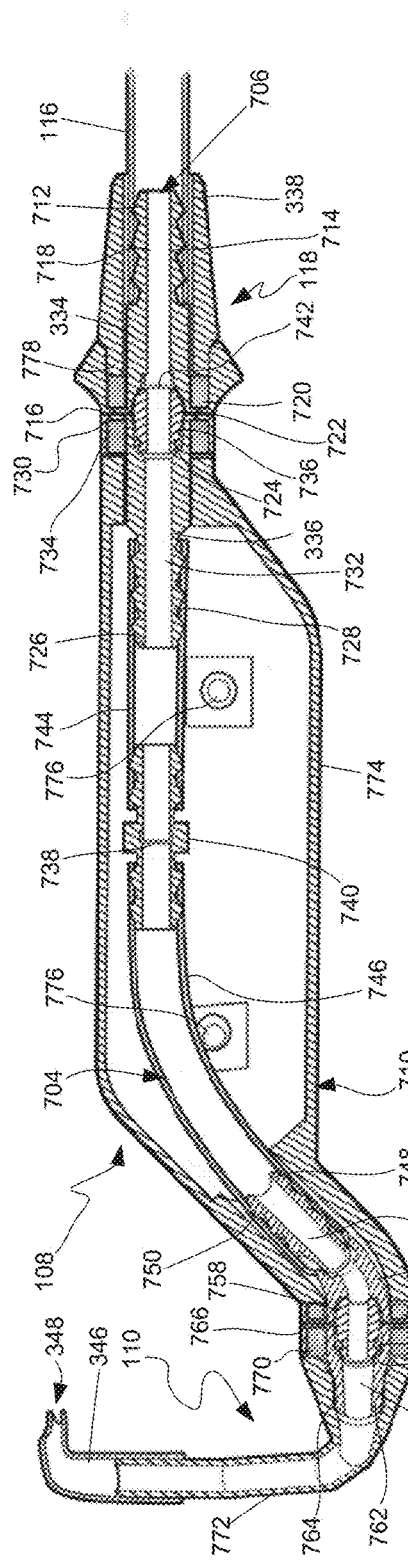
FIG. 7B is a cross-sectional view of the headset of FIG. 7A taken along the line 7B-7B.
Figure 7A:
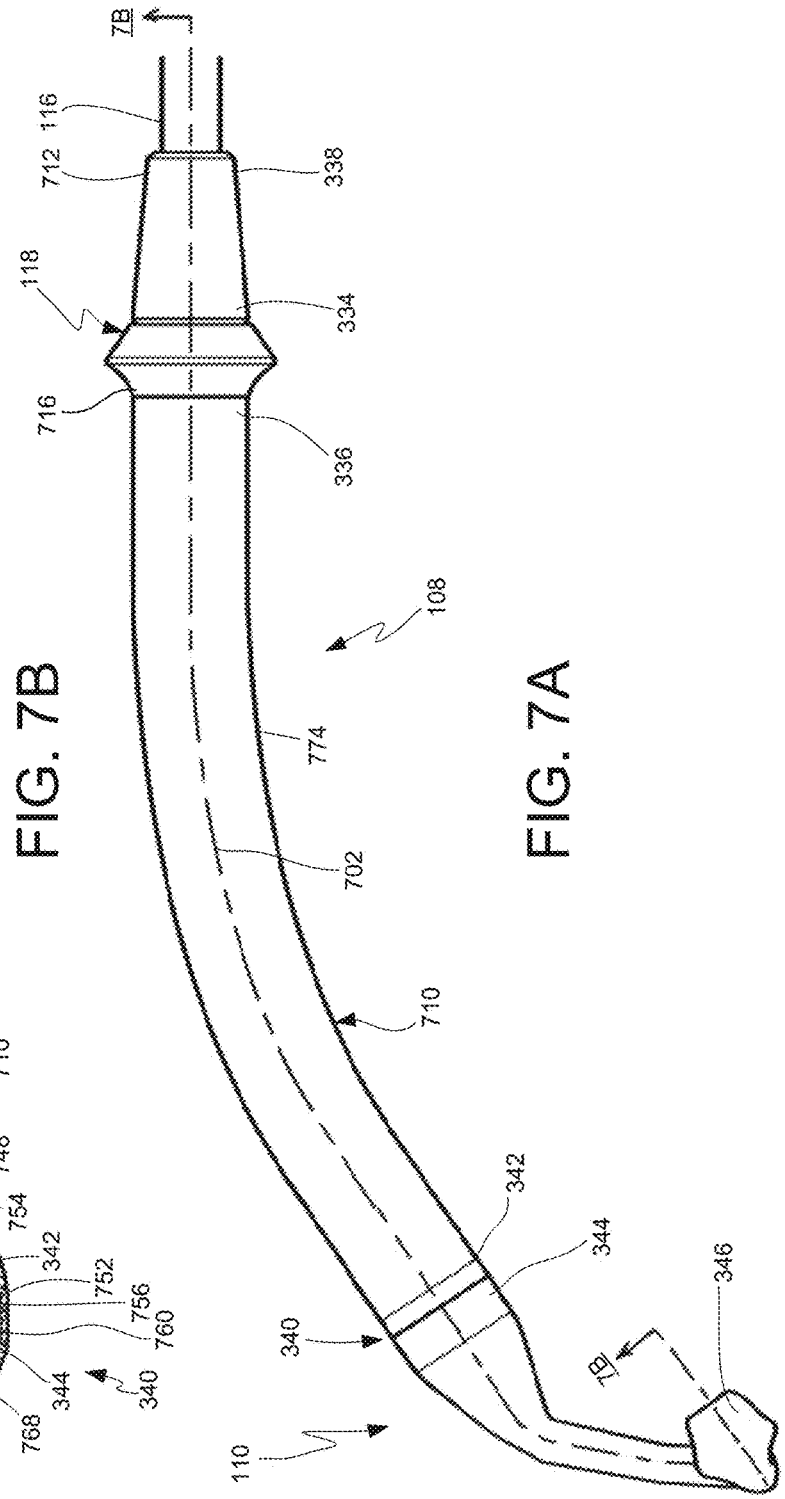
FIG. 7A is a top view of a one embodiment of a headset.
Figures 7C, 7D:
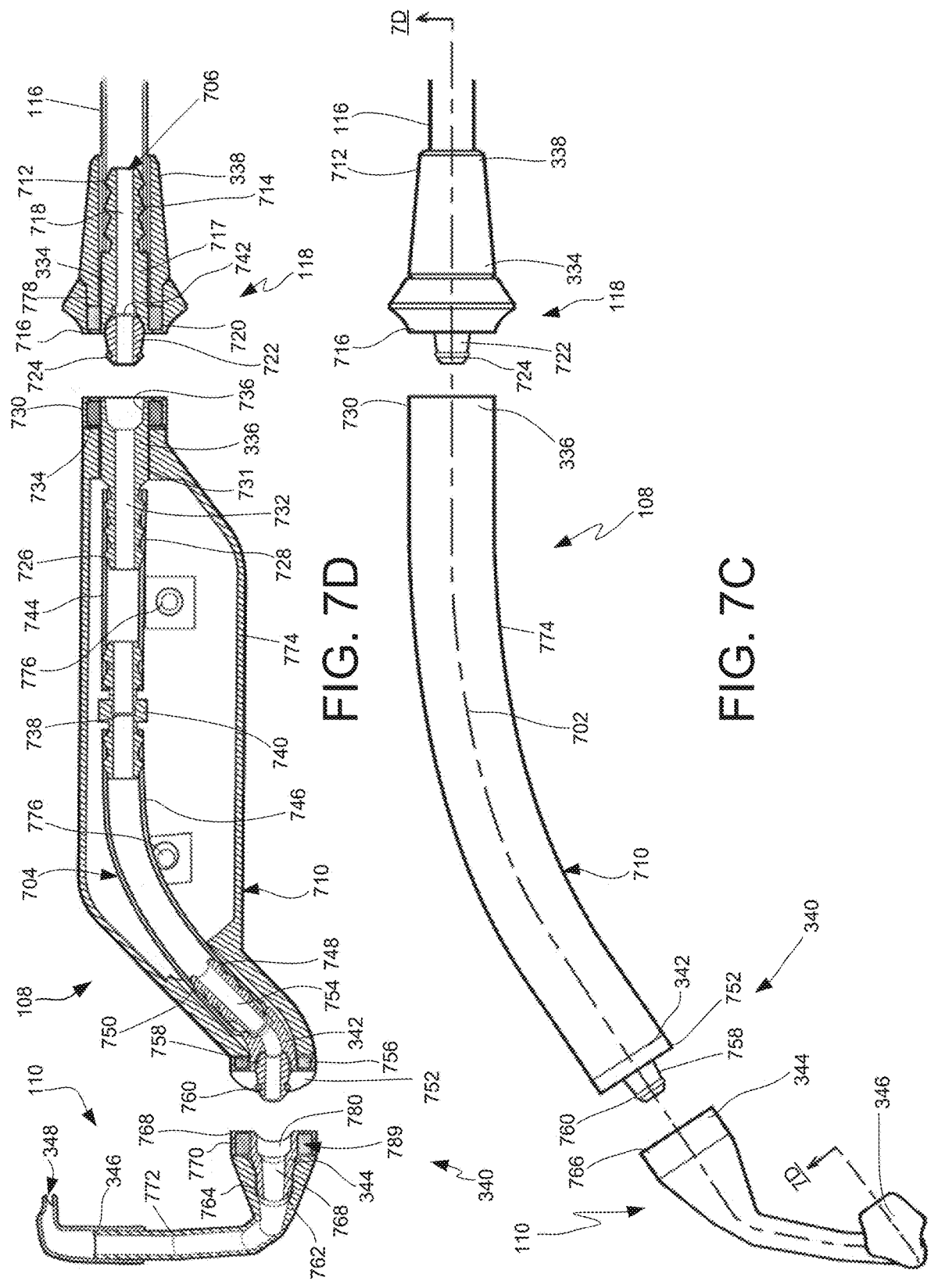
Figure 7E:
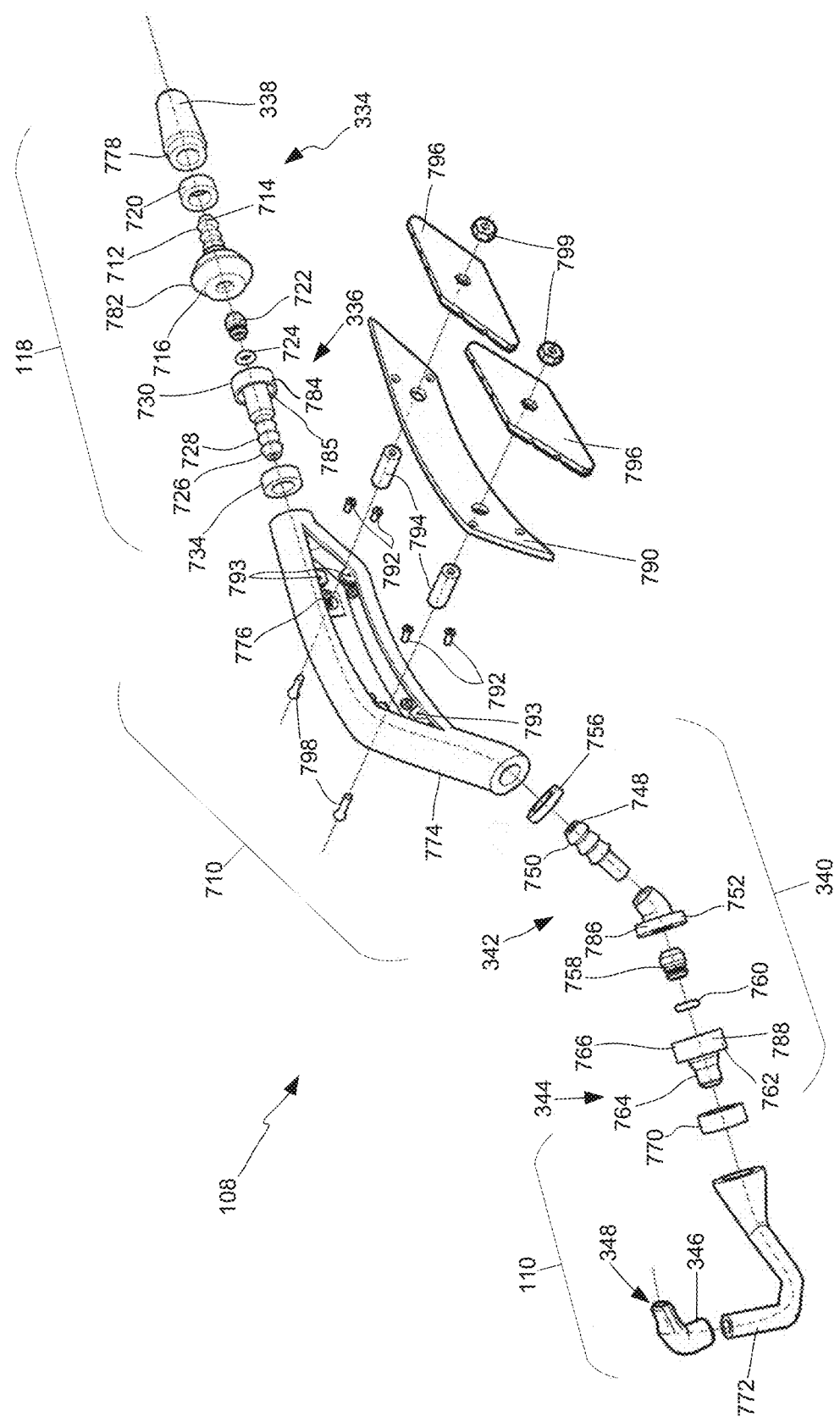
FIG. 7E is an exploded left, front isometric view of the headset of FIG. 7A.
Figure 7F:
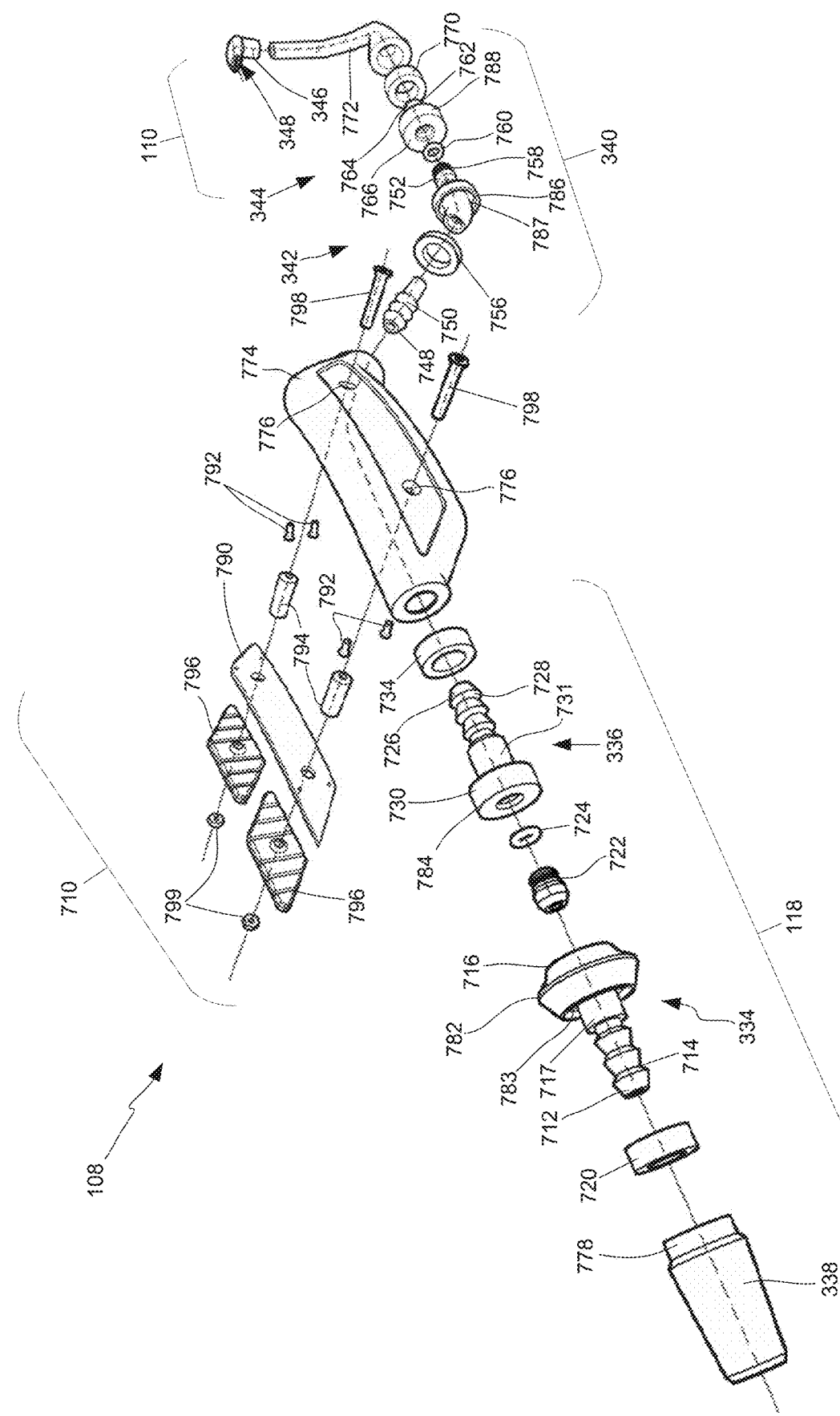
FIG. 7F is an exploded right, rear isometric view of the headset of FIG. 7A.

FIG. 7A is a top view of one embodiment of a headset 108 according to the present patent disclosure. FIG. 7C is another top view of the headset 108 of FIG. 7A, except that the male and female coupling members of magnetic quick connects 118 and 340 are shown separated. FIGS. 7B and 7D are cross-sectional views of the headsets taken along line 7B-7B in FIG. 7A and along line 7D-7D in FIG. 7C, respectively, where lines 7B-7B and 7D-7D represent the centerline 702 of headset 108. FIGS. 7E and 7F are exploded perspective views of the headset from different perspectives.

Headset 108 has a fluid conduit 704 having a fluid inlet port 706 at one end and a fluid outlet port 348 at a second end. The fluid inlet port 706 is provided in a connector 714 adapted to permit the fluid conduit to be detachably connected to a distal end of a drink tube 116 of hydration system 100. As a result, the fluid conduit 704 will be in fluid communication with the drink tube 116 when drink tube 116 is connected to hose connector 714, which in the illustrated embodiment is a barbed hose connector.

Magnetic quick connect 118, which comprises a male coupling member 334 and a female coupling member 336, defines a portion of the fluid conduit 704. In the illustrated embodiment, male coupling member is an upstream member and female coupling member 336 is a downstream coupling member. Furthermore, the fluid inlet port 706 is provided in the proximal end of hose connector 714, which also corresponds to a first or proximal end 712 of the upstream male coupling member 334. In other embodiments, female coupling member 336 may be used as the upstream coupling member and male coupling member 334 used as the downstream coupling member.

Support structure or mounting bracket 710 of the present embodiment, which will be described in more detail below. In general support structure 710 is configured to support the magnetic quick connect 118 and at least a portion of the fluid conduit 704 on helmet 109. In other embodiments in which the headset will be attached to other forms of headgear, then the support structure may be configured to support magnetic quick connect 118 and at least a portion of the fluid conduit 704 on the applicable headgear that will be worn on a user's head.

Headset 108 may also include a second magnetic quick connect 340 that defines a portion of the fluid conduit 704 downstream of magnetic quick connect 118. The second magnetic quick connect 340 also comprises a male coupling member 342 and a female member 344. In the illustrated embodiment, male coupling member 342 is the upstream member and female coupling member 346 is the downstream member. In other embodiments, male coupling member 342 may be the downstream member and female coupling member 346 may be the upstream coupling member.

Headset 108 may further comprise a detachable mouthpiece assembly 110. A first end of the detachable mouthpiece assembly 110 may comprise the downstream, or in the present embodiment, female coupling member 344 of the second magnetic quick connect 340. The fluid outlet port 348 is provided at a second, distal end of the detachable mouthpiece assembly 110. As illustrated, the detachable mouthpiece assembly 110 may further comprise a detachable mouthpiece 346 and the fluid outlet port 348 may be provided in the detachable mouthpiece. In some embodiments, the detachable mouthpiece 346 may comprise a bite-valve. In other embodiments, like that illustrated in FIGS. 3A and 7A-7E, the detachable mouthpiece may simply comprise a nozzle.

Headset 108 may also include one or more valves, such as valve 738, interposed in the fluid conduit 704 between the first magnetic quick connect 118 and the second magnetic quick connect 340. A valve 742 may also be interposed in the fluid conduit 704 between the inlet port 706 and a downstream end of the upstream coupling member of the magnetic quick connect 118, which in the present embodiment is the male coupling member 334.

Valves 738 and 742 may, for example, comprise a one-way check valve or a two-way valve. A food grade silicon dispensing valve, such as those used in non-drip squeezable condiment dispenser bottles, may be used as a suitable two-way valve for valve 738 or 742.

Regardless of whether one-way or a two-way valve is used, the valves 738 and 742 should open when a threshold cracking pressure is applied to each valve based on the pressure differential achieved in the fluid conduit 704 immediately upstream and downstream of each valve. If a two-way valve is used, then the valve will open in the appropriate direction when the required pressure differential (or cracking pressure) is achieved on either side of the valve.

Inclusion of valves in headset 108 in this manner is beneficial because it helps to keep hydration fluids in the fluid delivery system 103. In other words, it keeps fluids from receding back to the reservoir 104 after the pump 306 is turned off. This allows fluids to be delivered immediately following each activation of the pump 306, as opposed to the pump 306 first having to refill the delivery hose 116 with fluids each time the pump 306 is turned on.

Inclusion of valves 738 and 742 will also minimize the amount of hydration fluids that escape from fluid delivery tube 116 and headset 108 when the male and female coupling members 334, 336 of magnetic quick connect are decoupled from one another. This minimizes the loss of fluids from the system 100 and the leaking of fluids onto user 90.

Preferably valve 742 is a two-way valve so that fluid may flow in both directions through valve 742. In this way, when coupling member 334 is disconnected from female coupling member and then connected to another source of hydration fluids, reservoir 104 may be refilled through dispensing hose 116 using the refill feature described above. On the other hand, if a one-way valve is used for valve 742, refilling is not possible through male coupling member 334 because fluid may not flow in reverse through valve 742.

Because mouthpiece assembly 110 is attached to the headset 108 with the second magnetic quick connect 340, the mouthpiece assembly may be rotated. In addition, mouthpiece 346 may slide or telescope on shaped conduit 792 of mouthpiece assembly 110. This ability to rotate the mouthpiece assembly relative the rest of the headset as well as the ability to telescope (or adjust) the height of the mouthpiece 346 relative to the shaped conduit 772 facilitates the positioning of mouthpiece 346 and ultimately outlet port 348 next to a user's mouth.

Mouthpiece assembly 110 is more fully described in the section entitled Detachable Mouthpiece Assembly below.

One embodiment of magnetic quick connect 118 will now be described in more detail in reference to FIGS. 7 and 8.

Male coupling member 334 of magnetic quick connect 118 comprises a first end 712, a second mating end 716, a first fluid communication path 718 extending from the first end 712 to the second mating end 716, and a first magnetic material 720 disposed about the fluid communication path 718 in a position proximate the second mating end 716.

Similarly, the female coupling member 336 comprises a first end 726, a second mating end 730, a second fluid communication path 732 extending from the first end 726 to the second mating end 730, and a second magnetic material 734 disposed about the fluid communication path 732 in a position proximate the second mating end 730.

The second mating end 716 of the male coupling member 334 includes a protrusion 722 having a cross-sectional profile that is dimensioned to fit within an outer cross-sectional profile of the second mating end 730 of the female coupling member 336. Further, a portion of the first fluid communication path 718 extends through the protrusion 722, and an O-ring 724 is disposed about the protrusion. The second mating end 730 of the female coupling member 336 includes a protrusion mating surface 736 shaped so as to define a protrusion receiving area within the second mating end 730 of the female coupling member 336. The protrusion 722 and protrusion mating surface 736 are configured so that when the male and female coupling members 334, 336 are coupled together, the protrusion 736 extends into the protrusion receiving area, the first fluid communication path 718 and second communication path 732 are aligned and in fluid communication, and the O-ring 724 is compressed between the protrusion 722 and protrusion mating surface 736.

Further, the first and second magnetic materials 720, 734 are disposed proximate the second mating end 716, 730 of their respective coupling members so that when the male and female coupling members 334, 336 are coupled together, they are detachably held together by an attractive force between the first and second magnetic materials 720, 734.

The O-ring 724 preferably forms a fluid-tight seal between the protrusion 722 and the protrusion mating surface 736 when the male and female coupling members 334, 336 are coupled together.

It should be noted that while magnetic quick connect is being shown in use of a fluid delivery system 103 for a hydration system 100, its use is not so limited. The magnetic quick connects 118 of the present patent document may be used in a host of gas and/or liquid delivery or communication systems to connect two fluid conduits together in fluid communication with one another. Thus, in liquid delivery systems. O-ring 724 preferably forms a liquid-tight seal between the protrusion 722 and the protrusion mating surface 736 when the male and female coupling members 334, 336 are coupled together. On the other hand, in gas delivery systems, the O-ring 724 preferably forms a gas-tight seal between the protrusion 722 and the protrusion mating surface 736 when the male and female coupling members 334, 336 are coupled together.

In some embodiments, at least one of the first magnetic material 720 and the second magnetic material 734 comprises a permanent magnet. Preferably each of the first magnetic material and 720 the second magnetic material 734 comprise a material selected from the group consisting of a ferromagnetic material and ferrimagnetic material.

The male and female coupling members 334, 336 (including the placement, size, and magnetic strength of the first and second magnetic materials 720, 734) are preferably configured so that an axial pull force that is greater than or equal to about 48 ounce-force and less than or equal to about 128 ounce-force between the male coupling member and female coupling member is required to decouple the coupling members in the axial direction. More preferably, the male and female coupling members 334, 336 are configured so that an axial pull force that is greater than or equal to about 64 ounce-force and less than or equal to about 96 ounce-force, and even more preferably greater than or equal to about 72 ounce-force and less than or equal to about 88 ounce-force, between the male coupling member 334 and female coupling member 336 is required to decouple the coupling members in the axial direction.

The protrusion 722 preferably comprises a body of revolution. In some embodiments, the protrusion 722 and protrusion receiving area may be tapered. The angle of taper is preferably in the range of 15° to 50° from the axis of the protrusion, more preferably, in the range of 20° to 40°, and even more preferably 25° to 35°. Tapering the protrusion 722 and protrusion receiving area in this manner, helps the male and female coupling members 334, 336 to be self-centering with respect to one another. It also allows the quality of the seal between the O-ring 724 and the protrusion receiving surface 736 to be increased.

The protrusion 722 and protrusion receiving area are also preferably sized so that the male coupling member 334 and female coupling member 336 may be decoupled by pivoting one coupling member relative to the other coupling member through the application of a torque to the pivoted coupling member. The distance that the protrusion 722 extends into the protrusion receiving area may also be set to less than the minimum diameter of the protrusion receiving area that receives the protrusion 722.

Preferably, the coupling members 334, 336 are configured so that the torque required to decouple the coupling members is in the range of about 16 ounce-inches to about 72 ounce-inches, more preferably in the range of about 35 ounce-inches to about 64 ounce-inches, and yet even more preferably in the range of about 48 ounce-inches to about 60 ounce-inches. The pivoted coupling member may comprise a lever arm of greater than or equal to about 1.0 inches and less than or equal to about 2 inches, and more preferably greater than or equal to about 1.5 inches and less than or equal to about 2 inches, from the pivot point in order to facilitate the application of a suitable torque to decouple the coupling members.

Male coupling member 334 may further comprise a first collar 782 disposed at the second mating end 716. Similarly, female coupling member may further comprise a second collar 784 disposed at the second mating end 730 of the female coupling member. In such embodiments, the first collar 782 preferably defines at least part of a surface of the male coupling member 334 that abuts the female coupling member 336 when the male and female coupling members 334, 336 are coupled together. Further, the second collar 784 preferably defines at least part of a surface of the female coupling member 336 that abuts the male coupling member 334 when the male and female coupling members 334, 336 are coupled together.

The first magnetic material 720 may be disposed within the first collar 782 and the second magnetic material 734 may be disposed within the second collar 784. For example, the first magnetic material 720 may be disposed within an annular channel 783 defined by the first collar 782, and the second magnetic material 734 may be disposed within an annular channel 785 defined by the second collar 784.

Further, the first magnetic material 720 and second magnetic material 734 may be ring-shaped. In such embodiments, the first fluid communication path 718 may be configured to extend coaxially through the first magnetic material 720 and the protrusion 722, and the second fluid communication path 732 may be configured to extend coaxially through the second magnetic material 734.

At least one of the first collar 782 and second collar 784 may define an annular channel 783, 784 that is open away from the abutting surfaces of the first and second collars.

In some embodiments, the first end 712, 726 of at least one of the male coupling member 334 and female coupling member 336 further comprises a connector 714, 728, such as a barbed hose connector, to facilitate connection of the magnetic quick connect to a hose, such as drink tube 116 of hydration system 100.

As previously described, magnetic quick connect 118 may also include a removable hose collar 338. The hose collar in some embodiments may include an annular extension 778 at one end that is sized to be inserted within the annular channel 783. In such embodiments, an annular extension 778 is preferably sized to provide an interference fit with the walls of the annular channel 783 and a cylindrical portion 717 of the second end 714.

In some embodiments, the first collar 782 comprises a body of revolution having a first diameter at the surface of the male coupling member 334 that abuts the female coupling member 336 and a second diameter that is greater than the first diameter at a first location rearward of the abutting surface. The first collar may further comprise a third diameter at a second location rearward of the first location, where the third diameter is greater than the first diameter, but less than the second diameter. Moreover, the diameter of the collar may transition smoothly from the first diameter to the second diameter and from the second diameter to the third diameter.

A cylindrical portion 731 at the second end of coupling member 336 may be sized so as to create an interference fit when inserted in a corresponding receiving hole provided on the proximal end of helmet mount 774. However, coupling member 336 may also be adhesively bonded to helmet mount 774.

As best seen in FIGS. 8A, B, a preferred flow direction 802 through magnetic quick connect 118. However, fluids may also flow in the opposite direction.

Support structure 710 of the present embodiment will be described in more detail with reference to FIGS. 7E and 7F.

Figure 28:
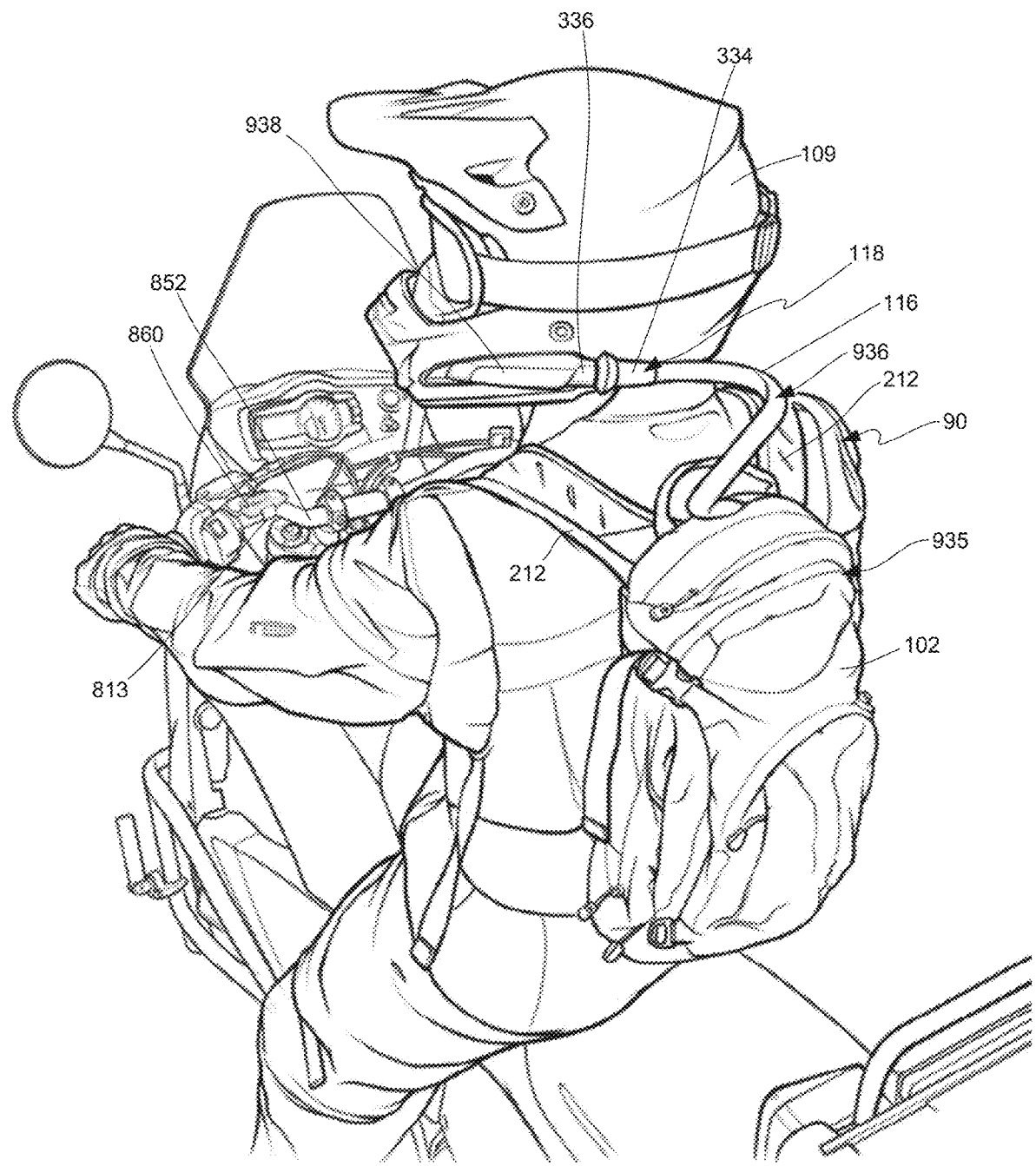
FIG. 28 is a motorcycle with another embodiment of a personal hydration system that includes a fluid delivery system including a fluid control unit and an integrated headset with a magnetic quick connect.

Generally speaking, the support structure of the headsets of the present patent document are (i) configured to attach to the headgear and support the headset on the headgear once attached, (ii) attached to the headgear, or (iii) at least partially formed integral with the headgear. For example, the support structure 710 of headset 108 is configured to attach to headgear (e.g., a helmet) as illustrated in FIGS. 7A-7F. On the other hand, in FIGS. 1 and 16 the support structure 710 of the headsets 108 is (as illustrated in those figures) already attached to headgear, namely a helmet (namely, helmet 109 in FIG. 1 and helmet 871 in FIG. 16). FIG. 28 shows a headset 938 that is formed integral with helmet 109 and thus has a support structure that is integrated with the helmet.

The support structure 710 is in effect a mounting bracket in that the components that collectively comprise the support structure 710 also mount the headset 108 to its intended headgear, which in the case of headset 108 is a helmet. Referring to FIGS. 7E and 7F, for example, mounting nuts 799 are provided in recesses on the back of adhesively backed mounting pads 796. The recesses provided on the back of adhesively backed mounting pads 796 are configured to keep nuts 796 from rotating when mounting screws 798 are attached thereto. Thus, to mount headset 108 to a helmet such as helmet 109, the protective tape of adhesive back pads 799 is removed, and the pads are pressed on to the outer shell of helmet 109 at the desired location, while nuts 799 are located in their respective recesses. Preferably the outer shell of helmet 109 is first cleaned so as to facilitate the adhesion of helmet pads 796. There are a number of suitable adhesive pads that may be used for this purpose on the market. Alternatively, pads 796 may be formed from a desired shock absorbing material, and then a double sided adhesive film attached to the back sides thereof.

Once pads 796 are located on helmet 109 at the desired location, then mounting screws 798 may be inserted through holes 776 provided in the outer wall of helmet mount 774. When fully inserted, the mounting screws will extend through their respective tubular supports 794, their respective holes provided in side plate 790, and holes provided in the respective helmet pads 796 so as to engage with a mounting nut 799. Thus, by tightening mounting screws 798 to mounting nuts 799, the helmet mount 774 will be drawn tight against the helmet pads attached to helmet 109, and the headset 108 will thereby be mounted on, or attached to, helmet 109.

Helmet mount 774 forms a hollow cavity that has an opening on the helmet side of the mount 774. After any necessary assembly steps within the cavity of the helmet mount 774, the opening may be closed with side plate 790. For example, side plate 790 may include holes for screws 792 to extend through and be screwed into corresponding threaded holes 793 provided within the cavity of helmet mount 774.

During fabrication, and before side plate 790 is attached, the cavity may be accessed to insert a portion of the fluid conduit 704 that extends between the first end 726 of female coupling member 336 and the second, mating end 752 of male coupling member 342. In the illustrated embodiment, a sub-assembly comprising two hoses 744, 766 connected together by a double hose connector 740 is inserted into the cavity of helmet mount 774. Double male hose connector includes valve 740 in its fluid pathway. In addition, it includes two hose connectors, such as barbed hose connectors at each end for connecting to hoses 744 and 746, respectively. The free end of hose 746 is connected to a hose connector, such as barbed hose connector 728, provided at the first end 726 of coupling member 336, which has previously been inserted into a receiving hole provided in a proximal end of mount 774. This puts the sub-assembly in fluid communication with the fluid communication path 732 of coupling member 336. The free end of hose 746 is connected to a hose connector, such as barbed hose connector 750, provided at the first end 748 of coupling member 342, which has been previously been inserted into a receiving hole provided in a distal end of mount 774. This puts the sub-assembly in fluid communication with the fluid communication path 754 of coupling member 342.

Another embodiment of a headset according to the present patent disclosure will now be described in connection with FIGS. 25 and 26. FIGS. 25 and 26 illustrate a user 901 wearing a headset 900. Headset 900 comprises a head bracket mount 914 adapted to be worn on a user's head and a mounting bracket 912 attached to the head bracket mount 914. Mounting bracket 912 acts as a support structure for a fluid conduit 902 having a fluid inlet port in the proximal end of male coupling member 908 of a magnetic quick connect 906 and an outlet port 904 that may be positioned adjacent the mouth of user 901. Fluid conduit 902 may comprise a number of distinct elements, including, in the present embodiment, magnetic quick connect 906 and flexible tube 924.

The drink tube 116 is connected to a connector, such as a barbed hose connector, provided on the proximal end of male coupling member 908 and which defines the inlet port of headset 900.

Male coupling member 908 includes a protrusion 909 that has an O-ring 911 disposed thereon. Male coupling member 908 is configured to couple with female coupling member 910 of magnetic quick connect so that the O-ring 911 creates a fluid-tight, or substantially fluid-tight, seal with a protrusion receiving surface provided in the proximal end of female coupling member 910.

In some embodiments, the protrusion 909 comprises a body of revolution. Further, the protrusion 909 on male coupling member 908 and protrusion receiving area in female coupling member 910 may be tapered. The angle of taper is preferably in the range of 15° to 50° from the axis of the protrusion, more preferably, in the range of 20° to 40°, and even more preferably 25° to 35°. Tapering the protrusion 909 and protrusion receiving area in this manner, helps the male and female coupling members 908, 910 to be self-centering with respect to one another. It also allows the quality of the seal between the O-ring 911 and the protrusion receiving surface to be increased.

The distal end of female magnetic quick connect 910 comprises a hose connector that is connected to the proximal end of flexible tube 924 on one end and includes an outlet port 904 on the distal end. Preferably the fluid outlet port 904 is a nozzle.

The headset 900 may also comprise an adjustable frame 922 disposed about the flexible tube 924 so as to permit the positioning of the fluid outlet port 904 proximate the user's mouth. Adjustable frame 922 may include one or more articulating joints 926 to facilitate the ability of user 901 to adjust the position of outlet port 904 to his or her desired location during use. In other embodiments, the adjustable frame 922 may comprise other structures, including, for example, an adjustable conduit made from spiraled wire.

Head bracket mount 914 includes two opposing support members 916 connected together by a resilient U-shaped spring member 918. When the two opposing support members 916 are pulled away from one another, the U-shaped spring member 918 produces a biasing force that tends to bias the opposing support members 916 in a direction toward one another.

The head bracket mount 914 may also be configured so that when it is worn on a user's head (e.g., the head of user 901), the two opposing support members 916 contact opposite sides of the user's head. In some approaches, the U-shaped spring member 916 will wrap around the base of the user's skull. At least a middle portion of the U-shaped spring member 914 may include a pad, such as neck pad 920.

As illustrated in FIGS. 25 and 26, the mounting bracket 912 is configured to support the first magnetic quick connect 906 on the head bracket mount 914 so that when the head bracket 914 is worn by a user at least a portion of the first magnetic quick connect 906 will be disposed behind the ear of user, such as user 901. In some approaches, the upstream member of the first magnetic quick connect 906 will be disposed behind the user's ear.

Detachable Mouth Piece Assembly

Various aspects of detachable mouthpiece assembly 110 are now described in greater detail in connection with FIGS. 1, 3A and 7A-7F.

In one embodiment, the detachable mouthpiece assembly 110 comprises a portion of fluid conduit 704 that extends from an entrance port to the mouthpiece assembly 110 to an outlet port 348. A downstream coupling member 344 of magnetic quick connect 340 defines the entrance port and at least a portion of the fluid conduit 704.

The downstream coupling member 344 is configured to couple with a mating upstream coupling member 342 disposed at a distal end of the headset 108 and form magnetic quick connect 340. When coupling members 342 and 344 are coupled together, the portion of the fluid conduit 704 that extends through the mouthpiece assembly 110 will be in fluid communication with the portion of the fluid conduit 704 that extends through the remainder of headset 108. While in the present embodiment downstream coupling member 344 is a female coupling member and upstream coupling member 342 is a male coupling member, in other embodiments that may be reversed.

As described above, the detachable mouthpiece assembly 110 may also include a detachable mouthpiece 346 at its distal end, and the fluid outlet port 348 may be provided in the detachable mouthpiece 346. Detachable mouthpiece 346 may include a bite-valve or a nozzle. In addition, the detachable mouthpiece 346 may be adjustable so that the angle and/or height of the fluid outlet port can be adjusted relative to coupling member 344. Detachable mouthpiece is preferably formed from a soft and pliable elastomer, such as silicon.

Coupling member 342 may include an abutting surface with an indexing feature. Further, the abutting surface may be configured to abut with a mating surface that has a matching indexing feature provided at the second end 752 of the mating coupling member 344 when the two coupling members 342, 344 are coupled together. The indexing feature may be used to provide a means of setting the amount of angular rotation of the downstream coupling member 344 of the magnetic quick connect 340 relative to the upstream coupling member 342. The indexing pattern may, for example, comprise a saw tooth pattern or a rectangular tooth pattern.

In some embodiments, the detachable mouthpiece assembly 110 may further comprise a shaped conduit 772 that defines at least a portion of the fluid conduit 704 distal to the downstream coupling member 344. The shaped conduit 772 may be configured to extend the fluid conduit 704 below a chin guard of a full-face helmet, such as helmet 109, when the mouthpiece assembly 1110 is coupled to the mating upstream coupling member 342 of headset 108 and the headset is mounted to the helmet. The shaped conduit 772 may also be configured to position the fluid outlet port 348 so that it is proximate to and directed toward the mouth of user 90 when wearing the helmet 109.

Shaped conduit 772 may mate with a mating or connector surface 764 provided at the first end 762 of coupling member 744. The shaped conduit may mate with surface 764 using an interference fit and or adhesive, or a combination of both. In some embodiments, the shaped conduit 772 may be formed integral with the coupling member 344.

Preferably, the coupling members 342, 344 are configured so that when they are coupled together, an axial pull force that is greater than 32 ounce-force and less than 54 ounce-force is required to decouple them in the axial direction. The coupling members 342, 344 are also preferably configured so that coupling member 344 may also be decoupled by pivoting it relative to the coupling member 342 through the application of a torque to the detachable mouthpiece 110. The torque required to decouple the downstream coupling member 344 from the upstream mating coupling member 342 is preferably set in the range of about 20 ounce-inches to about 36 ounce-inches.

Female coupling member 344 may comprise a first end 762, a second mating end 766, and a fluid communication path 768 extending from the first end 762 to the second mating end 768. In addition, a magnetic material 770 is preferably disposed about the fluid communication path 768 proximate the mating end 766. The mating end 766 of female connector 344 may include a protrusion mating surface 780 that defines a protrusion receiving area within the second mating end 766. The protrusion mating surface 766 may be shaped to match an outer surface of a protrusion 760 on the mating, upstream coupling member 344 so that when coupling members 342, 344 are coupled together, the protrusion 758 may be received within the protrusion receiving area.

The magnetic material 770 disposed at the second end 766 of coupling member 342 and the magnetic material 756 disposed at the second, mating end 752 of coupling member 344 are preferably disposed about the fluid communication path proximate the second mating end of their respective coupling members 342, 344 so that when the coupling members 342, 344 are coupled together, they are detachably held together by an attractive force between the magnetic material 770 and mating magnetic material 756 included in coupling member 344.

The magnetic material 770 and 756 may comprise, for example, a material selected from the group consisting of a ferromagnetic material and ferrimagnetic material. Preferably at least one of magnetic material 770 and 756 will comprise a permanent magnet.

Female coupling member 344 and its mating male coupling member 342 may each include a collar 788, 786, respectively, disposed at their second mating end 766, 752. The collars 786, 788 are preferably configured to define at least part of a surface of their respective coupling member 342, 344 that abuts the other coupling member when the coupling members 342, 344 are coupled together.

The magnetic material 756, 770 included in each coupling member 342, 344 is preferably ring shaped and disposed within their respective collars 786, 788. The collars 786, 788 also preferably each define an annular channel 787, 789 that is open away from the abutting surface of the collars 756, 770 and the first and second magnetic materials 756, 770 are disposed within the annular channel 787, 789 defined by the collar.

Preferably coupling members 342 and 344 are configured so that when they are coupled together O-ring 760 disposed on protrusion 750 is compressed between the protrusion 750 and protrusion receiving surface and fluid-tight seal is formed.

Protrusion 758 preferably comprises a body of revolution. And, for the reasons discussed above with respect to magnetic quick connect 118, the protrusion 758 of the coupling member 342 and the protrusion receiving area of coupling member 344 may be tapered. The angle of taper is preferably in the range of 15° to 50° from the axis of the protrusion, more preferably, in the range of 20° to 40°, and even more preferably 25° to 35°.

Additional Exemplary Hydration Systems and Vehicles

Figure 14:
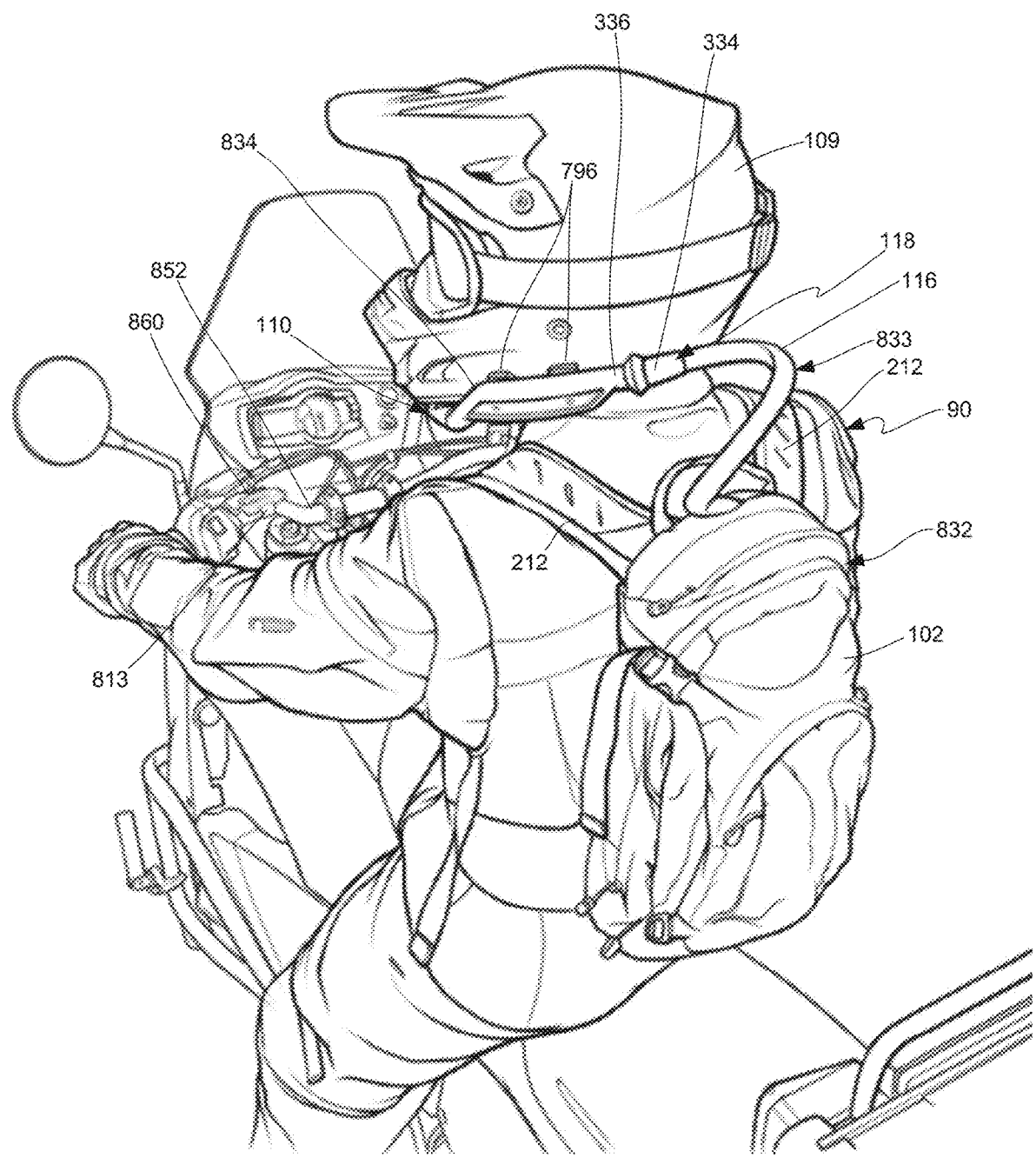
FIG. 14 is another view of the motorcycle and personal hydration system of FIG. 13.

Referring to FIGS. 13-15, a user 90 is shown with a personal hydration system 832 while operating a motorcycle 830. Personal hydration system 832 is the same as hydration system 100 previously described, except that instead of using a fluid delivery system 103, personal hydration system 832 includes a fluid delivery system 833.

Fluid delivery system 833 differs in two respects from fluid delivery system 103 previously described. First, headset 108 is replaced with a headset 834 in fluid delivery system 833. Second, two button wireless transmitter 860, which has been previously described, is substituted for the single button wireless transmitter 114 in the wireless actuation system 140 of fluid control unit 106.

Headset 834 is the same as previously described headset 108 except that the centerline 702 of the headset 834 curves to right so that headset 834 is designed to mount on the left side of helmet 109. By contrast, the centerline 702 of headset 108 curves to the left so that the headset 108 is configured to mount on the right side of a helmet 109. Otherwise headsets 108 and 834 are the same.

In the embodiment shown in FIGS. 13-15, microswitch 112 is mounted on the clutch lever 858 using the first mounting means (808, 210). Clutch lever 858 is in turn attached to handlebar 852 of the hand operated steering mechanism 850 of motorcycle 830. Microswitch 112 is mounted on the clutchlever 858 in a location sufficiently proximate to where a hand of user 90 would grip hand grip 868 on handlebar 852 so that user 90 can operate the microswitch 112 with his or her finger without the user 90 having to remove his or her hand from the hand grip 868. In other embodiments, the microswitch may be mounted in other locations sufficiently proximate the left-hand grip 868 so that user 90 can operate switch 112 with his or her thumb without removing his or her hand from the hand grip 868. In addition, the microswitch 112 could be mounted on a location proximate the right-hand grip on handlebar 852 such as on the right, hand break lever attached to the handlebar 852 so that user 90 can operate the microswitch 112 with his or her right index finger or thumb without removing his or her hand from the handlebar 852.

As best seen in FIG. 15, while switch 112 is mounted on clutch lever 858 attached to handlebar 858 for easy operation by a user's index finger during operation of motorcycle 830, wireless transmitter 860 is directly mounted more remotely on handlebar 852 using second mounting means 813. Switch 112 and transmitter 860 are operably connected via wire 804 and connector 806.

Steering mechanism 850 of motorcycle 830 includes handlebar 852, front fork 854 and front wheel 856. Handlebar 852 operably attached to front wheel 856 via front fork 854 in a conventional manner so that when the handlebar 852 is turned, the front wheel 856 is angled in the corresponding direction.

Motorcycle 830 also includes a conventional power train 836, which includes motor 838, transmission 840, drive train 842, rear sprocket 844, and driven wheel 846, all of which are operably connected together to transfer power from motor 836 to wheel 846 when transmission 840 is in gear and clutch lever 858 is released. Wheel 846 and rear sprocket 844 are rotatably supported on swing arm 848 with an axle.

Figure 17:
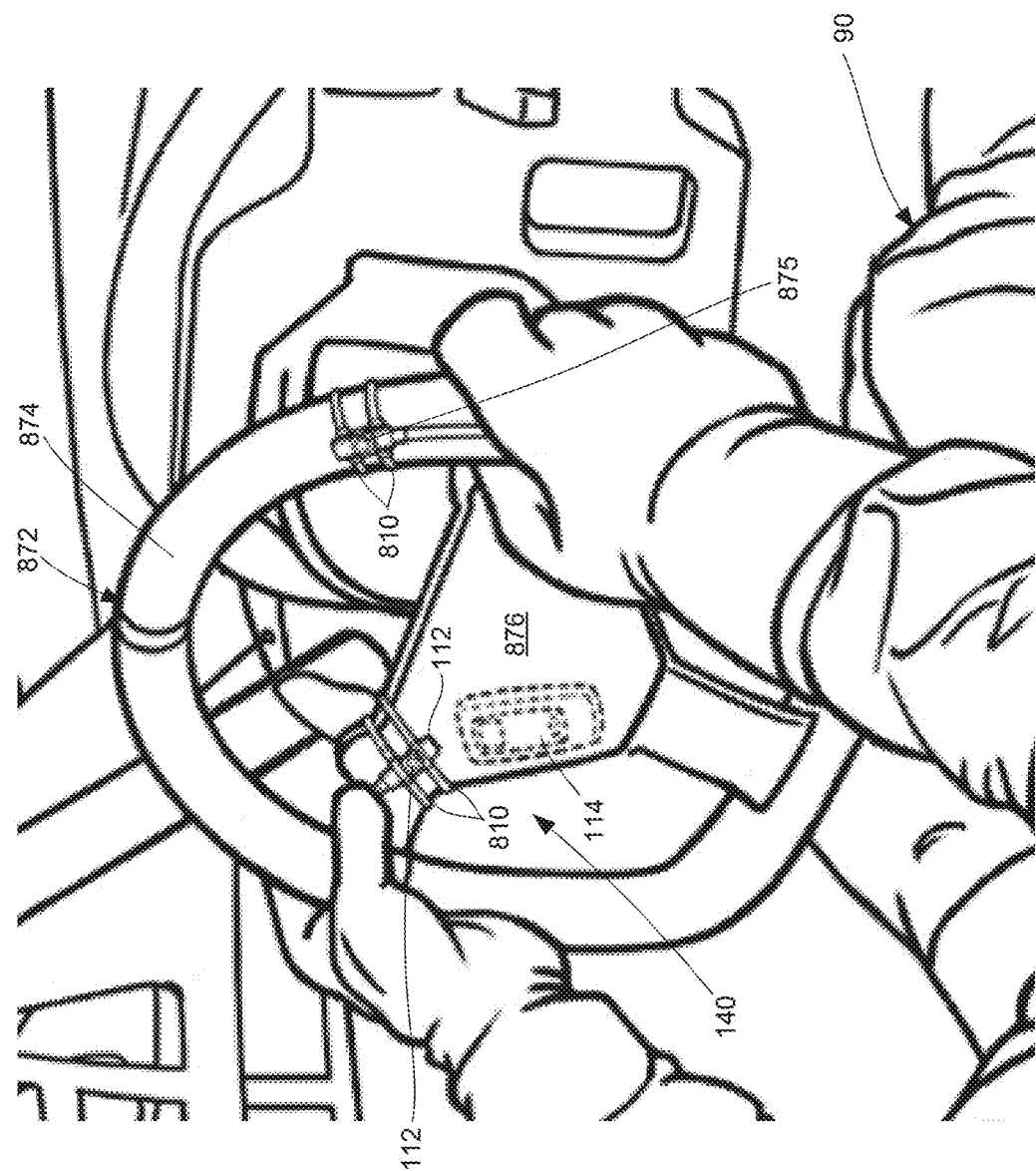
FIG. 17 is a close up view of the steering wheel of the race car of FIG. 16.
Figure 18:
FIG. 18 is a side elevational view an alternative embodiment of a transmitter that can be used to communicate with and control the fluid control unit.
Figure 21:
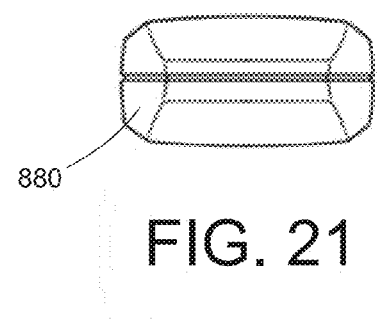
FIG. 21 is an end view of the transmitter of FIG. 18.

Referring to FIGS. 16-17, a user 90 is shown with a personal hydration system 100 while operating a racecar 870. Personal hydration system 832 is the same as hydration system 100 previously described with the variations noted below, except that instead of using a fluid delivery system 103, personal hydration system 832 includes a fluid delivery system 833.

Rather than being contained within a backpack 102, however, in the present embodiment reservoir 104 (which is not shown in FIG. 16) of hydration system 100 is disposed within the cabin of race car 870 so as to be supported directly or indirectly by the frame of race car 870 at a location behind user 90. In this way, the fluid reservoir 104 is supported on the frame of a vehicle 92 without the user 90 having to carry the reservoir on his or her person while operating vehicle 92.

In the illustrated embodiment, headset 108 of hydration system 100 is mounted on a different style of safety helmet 871. In addition, microswitch 112 is mounted on the hub 876 of steering wheel 874 of steering mechanism 872. Microswitch 112 is mounted using the first mounting means, and the wireless transmitter 114 is mounted out of the way on the rear of the hub 876 using the second mounting means. Microswitch 112 and transmitter 114 are operably connected as previously described. Microswitch 112 is mounted in location sufficiently proximate the user's left hand so that the user can operate microswitch 112 with his or her thumb without removing his or her hand from steering wheel 874.

Microswitch 112 may be mounted in other locations proximate the location of where one of the user's left or right hands would grip the steering wheel 874 so that the user can operate the microswitch 112 with a thumb or index finger without having to remove his or her hand from the steering wheel 874. For example, microswitch 875 in FIG. 17 illustrates an alternative mounting location for microswitch 112 that may be operated by the user's right thumb or index finger without having to remove his or her hand from steering wheel 874. In all other respects, microswitch 875 is the same as microswitch 112.

In other embodiments, both microswitches 112 and 875 may be provided on steering wheel 874 as shown and connected to the same transmitter 114 to provide alternative means of activating pump 306 in fluid control unit 106. Alternatively, microswitch 875 may be connected to another wireless transmitter for another hydration system 100. In this way, for example the user 90 may be able to deliver water from one hydration system and different fluid, such as a sports drink from a second hydration system controlled by microswitch 875.

Referring to FIG. 28, a user 90 is shown with a personal hydration system 935 while operating a motorcycle 830. Personal hydration system 935 is the same as hydration system 100 previously described, except that instead of using a fluid delivery system 103, personal hydration system 832 includes a fluid delivery system 936.

Fluid delivery system 936 differs from fluid delivery system 103 previously described in that it employs a headset 938 that is integrated with helmet 109 as opposed to being mounted thereon after fabrication of the helmet 109. As such, the fluid delivery path defined by the fluid delivery system 936 passes through the wall of helmet 109 as opposed to underneath the wall of helmet 109 as with headset 108 of the embodiment shown in FIG. 1. The microswitch 112 and transmitter 860 are mounted on the handlebar 852 of motorcycle 830 in FIG. 28 in the same manner as described above in connection with FIGS. 13-15.

Beneficially, the user 90 of each of the vehicles 92 of the foregoing embodiments of a vehicle including a hydration system may effortlessly remain hydrated without having to take his or her hand off the steering mechanism of the vehicle being operated to activate the hydration system.

Magnetic Connector Rest

An embodiment of a magnetic connector rest in accordance with the present patent disclosure will now be described in reference to FIGS. 22-24.

Magnetic connector rest 890 may be used in combination with a portable hydration system that includes a magnetic quick connect interposed in the fluid delivery path such that upstream coupling member of the magnetic quick connect is connected to the drink tube of the hydration system. Thus, for example, magnetic connector rest 890 may be used in combination with the fluid delivery system 103 of hydration system 100 described above.

In the illustrated embodiment, the magnetic connector rest comprises a landing pad 894. A magnetic material 734 is supported by the landing pad 894. Further, a base 891 is coupled to the landing pad 894 and configured to be removably secured to a desired structure.

Figures 22, 23, 24:
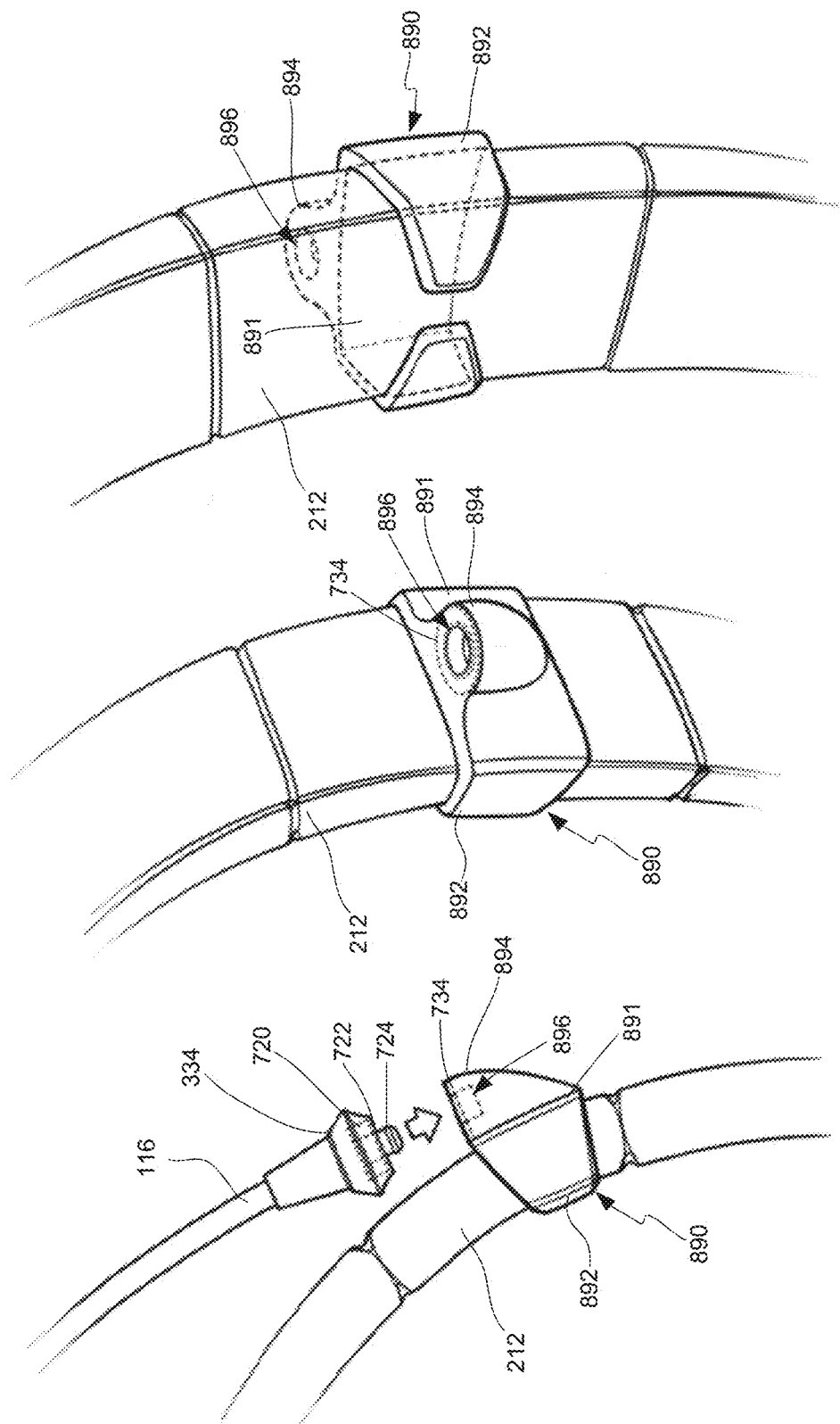
FIG. 22 is a side view of one embodiment of a magnetic connector rest for a coupling member of a magnetic quick connect.
FIG. 23 is a front perspective view of the magnetic connector rest of FIG. 22.
FIG. 24 is a rear perspective view of the magnetic connector rest of FIG. 22.

FIG. 22 illustrates the upstream, male coupling member 334 of magnetic quick connect 118 interacting with the landing pad 894 of the connector rest 890. As shown, coupling member 334 is attached at its proximal end to dispensing hose 116, and its distal, or mating, end interacts with the landing pad 894 as described more fully below.

The landing pad 894 and/or magnetic material 734 are preferably arranged to define a mating surface configured to mate with a mating end of the upstream coupling member 334. The magnetic material 734 is preferably disposed on the landing pad 894 so that when the upstream coupling member is brought into proximity with the landing pad 894, an attractive force between the magnetic material 734 and magnetic material 720 included in the coupling member 334 will cause the mating end of the coupling member 334 to mate with the mating surface of the landing pad 894 and detachably hold the coupling member 334 against the mating surface. In this way, the upstream coupling member 334 and the mating surface of the landing pad 894 may readily be connected by a user with a single hand without having to be able to view the coupling member 334 or the landing pad 894 when attaching the upstream coupling member to the magnetic connector rest 890.

The mating surface may be configured to protect the mating end of the coupling member 334 from dirt and other debris when mated with the mating surface of landing pad 894. In addition, the mating surface may include a shelf with a mating structural feature 896 for mating with a corresponding feature on the mating end of the upstream coupling member 334. Because coupling member 334, landing pad 894 is provided with a protrusion receiving area in the present embodiment. However, in other embodiments, a female coupling member, such as coupling member 336, may be the upstream coupling member instead of male coupling member 334. In such embodiments, the landing pad 894 may be provided with a protrusion 722, instead of a protrusion receiving area as the mating structural feature 896.

Magnetic material 734 is preferably ring-shaped and so that it can be disposed on landing pad 894 so that mating feature 896 is coaxial with the magnetic material 734. For example, as shown, the protrusion receiving area extends coaxially through the magnetic material 894.

Magnetic material 734 may comprise a material selected from the group consisting of a ferromagnetic material and ferrimagnetic material, but preferably comprises a permanent magnet.

The magnetic material 734 may be sized-like magnetic material 734 of female coupling member 336—so that an axial pull force that is greater than about 32 ounce-force and less than about 128 ounce-force between the landing pad 894 and the coupling member 334 is required to decouple the upstream coupling member 334 from the mating surface of the landing pad 894 in the axial direction. More preferably, an axial pull force that is greater than about 64 ounce-force and less than about 96 ounce-force, and even more preferably an axial pull force that is greater than about 72 ounce-force and less than about 88 ounce-force, is required to decouple the coupling member 334 from the mating surface of the landing pad 894 in the axial direction.

The protrusion receiving area 896 is preferably sized so that the coupling member 334 may be decoupled from the mating surface by pivoting the coupling member 334 relative to the mating surface through the application of a torque. The mating surface may be configured, for example, so that the distance that the protrusion 722 extends into the protrusion receiving area 896 is less than the minimum diameter of the protrusion receiving area 896 that receives the protrusion 722.

The magnetic material may also be sized so that the coupling member 334 may be decoupled by pivoting the coupling member 334 relative to the landing pad 894 through the application of a torque in the range of about 16 ounce-inches to about 72 ounce-inches. More preferably the torque is in the range of about 35 ounce-inches to about 64 ounce-inches, and even more preferably in the range of about 48 ounce-inches to about 60 ounce-inches.

In some embodiments, the base 891 may include a mounting bracket. In the embodiment shown in FIGS. 22-24, the base 891 includes a mounting bracket in the form of a clip 892. Clip 892 may, for example, be generally C-shaped clip with two opposing resilient arms that are anchored at a common end and include opposing extensions that extend toward one another at their opposite ends. The opposing resilient arms may, for example, be configured to define a backpack strap receiving area therebetween that can be accessed through an adjustable gap provided between the opposing extensions. The opposing resilient arms are preferably configured so that when they are in an unbiased state the adjustable gap between the opposing extensions is sized to prevent a strap, such as strap 212, of a predetermined size from accessing (or leaving) the strap receiving area. Further, the resilient opposing arms are preferably configured so that when the opposing resilient arms are pulled away from one another, a biasing force tends to bias the opposing resilient arms in a direction toward one another, and the adjustable gap can be made to be of sufficient width to allow straps of the predetermined size, such as shoulder strap 212 of backpack 102, to access (or be removed from) the strap receiving area so that once a strap of the predetermined size is inserted in the strap receiving area and the opposing arms of clip 892 are no longer pulled away from one another they will clamp onto the strap 212.

While the illustrated embodiment uses a clip 892 as a mounting bracket, in other embodiments, the base 891 may include other types of mounting brackets or fastener means. For example, base 891 may further comprise a hook or loop fastener strip disposed on the back side of the base 891 for mounting on a corresponding fastener strip disposed on a shoulder strap 212. In still other embodiments, the base 891 may include a pair of opposing straps, where each strap is attached at one end to opposite sides of the base 891, and the other end of each of the straps comprises a hook and a loop fastener, respectively.

Further, in the illustrated embodiment, the desired structure to which the magnetic connector rest 890 is attached is shoulder strap 212 of backpack 102. However, in other embodiments, the magnetic connector rest may be configured to be removably secured to a different structure from which a user may conveniently place the coupling member 334 when the fluid delivery system 103 of hydration system 100 is not in use, or conveniently access coupling member 334 when getting ready to use the hydration system 100.

Alternative Microswitch and Mounting Means

Figure 27:
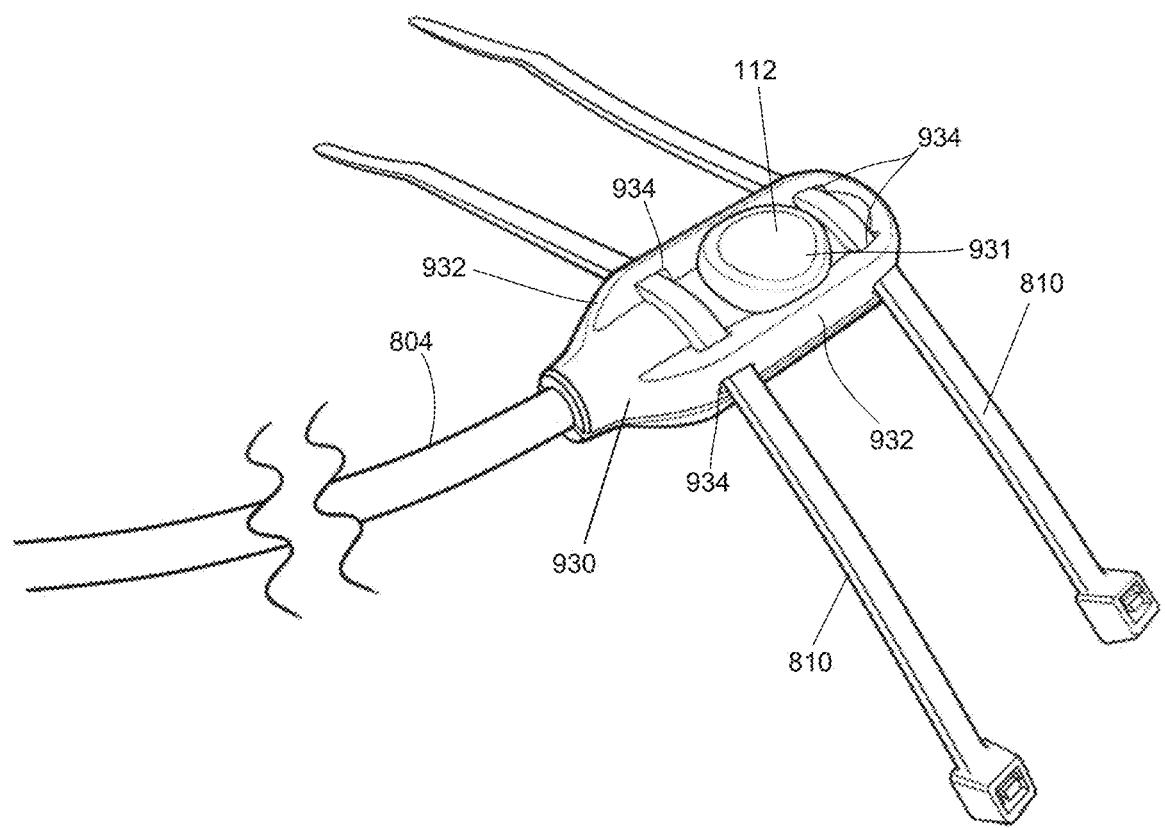
FIG. 27 is a schematic view of an alternative embodiment of a microswitch and first mounting means that may be used in connection with various aspects of the present patent document, including the fluid delivery systems and fluid control units of the present patent document.

FIG. 27 illustrates another embodiment of a microswitch 112 and first mounting means. Instead of employing heat shrink tubing 808 and cable ties 810 for the first mounting means as was the case in the embodiments illustrated in FIGS. 1, 15, and 17, in the embodiment illustrated in FIG. 27, the first mounting means includes the body 930 of the microswitch 112 and a pair of cable ties 810 or other straps. The body 930 of the microswitch 112 is formed to include one or more slots 934 on opposing sides of the actuation button 931 of switch 112 for receiving a strap, such as a cable tie 810, therethrough. In the embodiment illustrated in FIG. 27, the body 930 of microswitch 112 includes a pair of opposing longitudinal extensions 932 that generally extend longitudinally on opposite sides of the actuation button 931 of switch 112 upward from the body 930. Each of the longitudinal extensions 932 include a pair of slots 934 located on opposite sides of the actuation button 931 of switch 112. As illustrated in FIG. 27, the slots 934 formed in each of the longitudinal extensions 932 are preferably sized and located so that one cable tie 810 (or other strap) can be inserted through each of the opposing slots 934 formed in the pair of opposing longitudinal extensions 932 that are formed on one side of the actuation button 931 and another cable tie 810 may be inserted through each of the opposing slots 934 formed in the pair of opposing longitudinal extensions 932 that are formed on the other side of the actuation button 931. The pair of cable ties 810 may then be used to attach the microswitch 112 to the desired portion of a hand operated steering mechanism, such as hand operated steering mechanism 122, 850, or 872, as described above. In other embodiments, other configurations of body 930 may be employed to receive cable ties or other fastening straps or mechanisms to attach microswitch 112 to a desired portion of a hand operated steering mechanism. In addition, the microswitch 112 may also be attached to structures other than steering mechanisms. For example, switch 112 may be attached to a passenger hand bar, so that the passenger of a vehicle 92 may also use a hydration system 103 according to the present patent document event though the passenger is not operating the vehicle.

Refill System

Figure 29:
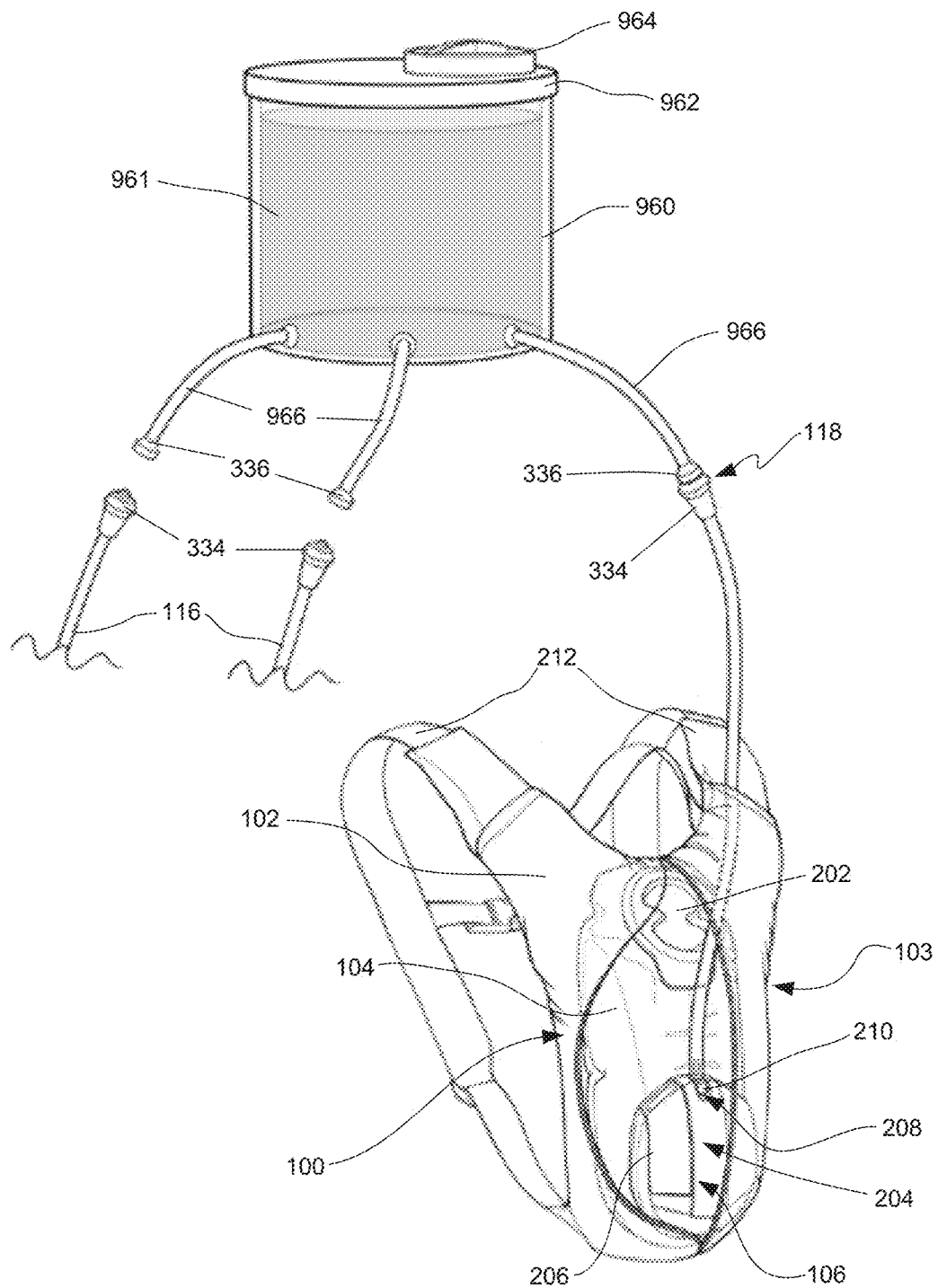
FIG. 29 is a schematic illustration of a refill station that may be used to refill a portable hydration system.

FIG. 29 illustrates one embodiment of a refill system according to the present patent document. The illustrated refill system includes a refill reservoir 960 to which one or more refill hoses 966 are attached at their proximal ends so as to be in fluid communication with the inside of reservoir 960. The distal end of each refill hose 966 is provided with a magnetic coupling member. The magnetic coupling member should be configured to mate with the upstream coupling member of a magnetic quick connect 118 that is disposed at the distal end of dispensing hose 116 of hydration system 100 that refill system is to service.

In the illustrated embodiment, refill reservoir 960 includes a lid 962 having a refill cap 964, which in combination form a closure to the top of reservoir 960. The refill systems of the present patent document, however, can take on any suitable form, and depending on the application may be made out of rigid, semi-rigid, or flexible material. For example, it may be desirable to employ a flexible or semi-rigid reservoir 960 for a refill system to be included in a troop carrier, tank, or fire truck. Regardless of the rigidity of the reservoir 960, or its shape, the material selected for reservoir 960 should be compatible with the hydration liquid held by the reservoir.

In the embodiment shown in FIGS. 1 and 3A, the upstream coupling member of magnetic quick connect 118 of hydration system 100 corresponds to a male coupling member 334. Thus, the coupling member provided at the distal end at least one of the refill hoses 966 should correspond to a mating, female coupling member 336 so that the two can combine to form a magnetic quick connect 118.

In other embodiments, a female coupling member 336 may be disposed at the distal end of drink tube 116. In such embodiments, the coupling member provided at the end of refill hoses 966 will need to be a corresponding male coupling member 334 in order to allow the two coupling members to join to form a magnetic quick connect 118.

If the refill system is intended to service a variety of hydration systems, each employing a different style of magnetic coupling member at the end of dispensing hose 116, then each refill hose 966 may be provided with a corresponding magnetic coupling member configured to mate with the coupling member of the hydration system 100 it is intended to mate with.

Preferably the refill system includes a plurality of refill hoses 966 so that more than one hydration reservoir 104 of a personal hydration system 100 may be refilled from reservoir 960 at the same time with hydration liquid 961 contained within the reservoir and/or so that the system can provide refill service to hydration systems employing multiple styles of magnetic coupling members at the distal end of drink tube 116.

A stop cock may be included in each of refill line to ensure that hydration liquid 961 does not flow from reservoir 960 unintentionally. Alternatively, or in addition, a one-way or two-way valve 742 may be disposed within magnetic coupling member 336. The cracking pressure of the valve 742 should be selected for this use so that the anticipated head of pressure from the hydration liquid being in the reservoir 960 is insufficient to cause liquid to flow from the reservoir 960 through refill hoses 966 and coupling members 336.

To refill the fluid reservoir 104 of a hydration system 100, a user 90 would uncouple male coupling member 334 from female coupling member 336 at the proximal end of headset 108. The user would then couple the male coupling member 334, which is in fluid communication with the reservoir 104 via dispensing hose 116, with the female coupling member 334 that is provided at the end of one of the refill hoses 966. Once coupling members 334 and 336 are coupled, the user can activate the refill mode of the pump 306 within fluid control unit 106. As described above, this can occur, for example, by causing a wireless transmitter, such as wireless transmitter 114, 860, or 880, to communicate a command signal that will instruct the controller 428 to drive the pump 306 in reverse. Once the reservoir 104 has been filled to the desired capacity with hydration liquid 961 from refill reservoir 960, the user can operate the transmitter so that it no longer sends the refill command, for example, by releasing one of the buttons that had been pressed. The user can then disconnect coupling member 334 from coupling member 336.

Alternatively, the user may also press the refill button 456 on the fluid control unit until the desired amount of hydration liquid 961 has been transferred from refill reservoir 960 to reservoir 104. Once the desired amount of hydration liquid 961 has been transferred, then the user can release button 456 and disconnect coupling member 334 from coupling member 336.

Advantageously, user 90 does not need to remove hydration system 100 from his or her back to use a wireless transmitter to carry out the refill function. For this reason, the use of the wireless transmitter to carry out the refill function has an advantage over the use of refill button 456, which requires the user to remove back pack 102 to access the fluid control unit 106 contained therein.

The amount hydration liquid 961 that can be added to reservoir 104 using the refill features of the fluid control unit 106 will be greater than if filled through fill cap 202 for the reasons discussed previously.

EXEMPLARY CLAIM SETS

The following sections provide a series of exemplary claim sets that may be presented with respect to the subject matter of the present disclosure. In addition to the claims appended to the end of the present disclosure, these exemplary claim sets illustrate the scope of patentable subject matter that is supported by the present disclosure.

A. Magnetic Quick Connect Claims

The following exemplary claims provide an illustrative example of the scope of claims that may be presented with respect to the magnetic quick connect described herein.

1. A magnetic quick connect for a fluid delivery system, the magnetic quick connect comprising:
   a male coupling member, the male coupling member comprising:
      a first end,
      a second mating end.
      a first fluid communication path extending from the first end to the second mating end of the male coupling member, and
      a first magnetic material disposed about the fluid communication path in the male coupling member proximate the second mating end; and
   a female coupling member, the female coupling member comprising:
      a first end,
      a second mating end, the second mating end having an outer cross-sectional profile; and
      a second fluid communication path extending from the first end to the second mating end of the female coupling member, and
      a second magnetic material disposed about the fluid communication path in the female coupling member proximate the second mating end; wherein
   the second mating end of the male coupling member includes a protrusion having a cross-sectional profile that is dimensioned to fit within the outer cross-sectional profile of the second mating end of the female coupling member;
   a portion of the first fluid communication path extends through the protrusion;
   an O-ring is disposed about the protrusion; and
   the second mating end of the female coupling member includes a protrusion mating surface shaped to match the outer surface of the protrusion so as to define a protrusion receiving area within the second mating end of the female coupling member so that when the male and female coupling members are coupled together, the protrusion extends into the protrusion receiving area, the first fluid communication path and second communication path are axially aligned and in fluid communication, and the O-ring is compressed between the protrusion and protrusion mating surface; and
   wherein the first and second magnetic materials are disposed proximate the second mating end of their respective coupling members so that when the male and female coupling members are coupled together, they are detachably held together by an attractive force between the first and second magnetic materials.

2. A magnetic quick connect according to claim 1, wherein at least one of the first magnetic material and the second magnetic material comprises a permanent magnet.

3. A magnetic quick connect according to claim 2, wherein each of the first magnetic material and the second magnetic material comprise a material selected from the group consisting of a ferromagnetic material and ferrimagnetic material.

4. A magnetic quick connect according to claim 3, wherein an axial pull force that is greater than 48 ounce-force and less than 128 ounce-force between the male coupling member and female coupling member is required to decouple the coupling members in the axial direction.

5. A magnetic quick connect according to claim 3, wherein an axial pull force that is greater than 64 ounce-force and less than 96 ounce-force between the male coupling member and female coupling member is required to decouple the coupling members in the axial direction.

6. A magnetic quick connect according to claim 3, wherein an axial pull force that is greater than 72 ounce-force and less than 88 ounce-force between the male coupling member and female coupling member is required to decouple the coupling members in the axial direction.

7. A magnetic quick connect according to claim 4, wherein the protrusion comprises a body of revolution, and the distance that the protrusion extends into the protrusion receiving area is less than the minimum diameter of the portion of the protrusion receiving area that receives the protrusion.

8. A magnetic quick connect according to claim 7, wherein the male coupling member and female coupling member may also be decoupled by pivoting one coupling member relative to the other coupling member through the application of a torque that is in the range of about 16 ounce-inches to 72 ounce-inches to the pivoted coupling member.

9. A magnetic quick connect according to claim 7, wherein the male coupling member and female coupling member may also be decoupled by pivoting one coupling member relative to the other coupling member through the application of a torque that is in the range of about 35 ounce-inches to 64 ounce-inches to the pivoted coupling member.

10. A magnetic quick connect according to claim 7, wherein the male coupling member and female coupling member may also be decoupled by pivoting one coupling member relative to the other coupling member through the application of a torque that is in the range of about 48 ounce-inches to 60 ounce-inches to the pivoted coupling member.

11. A magnetic quick connect according to claim 8, wherein the pivoted coupling member comprises a lever arm of greater than or equal to about 1.0 inches and less than or equal to about 2 inches from the pivot point.

12. A magnetic quick connect according to claim 8, wherein the pivoted coupling member has a lever arm of greater than or equal to about 1.5 inches and less than or equal to about 2 inches from the pivot point.

13. A magnetic quick connect according to claim 1, wherein the male coupling member further comprises a first collar disposed at the second mating end of the male coupling member, and the female coupling member further comprises a second collar disposed at the second mating end of the female coupling member, and wherein the first collar defines at least part of a surface of the male coupling member that abuts the female coupling member when the male and female coupling members are coupled together, and the second collar defines at least part of a surface of the female coupling member that abuts the male coupling member when the male and female coupling members are coupled together.

14. A magnetic quick connect according to claim 13, wherein the first magnetic material is disposed within the first collar and the second magnetic material is disposed within the second collar.

15. A magnetic quick connect according to claim 14, wherein the rust magnetic material and second magnetic material are ring-shaped.

16. A magnetic quick connect according to claim 15, wherein the first fluid communication path extends coaxially through the first magnetic material and the protrusion, and the second fluid communication path extends coaxially through the second magnetic material.

17. A magnetic quick connect according to claim 14, wherein at least one of the first collar and second collar defines an annular channel that is open away from the abutting surfaces of the first and second collars.

18. A magnetic quick connect according to claim 17, wherein the first magnetic material is disposed within an annular channel defined by the first collar, and the second magnetic material is disposed within an annular channel defined by the second collar.

19. A magnetic quick connect according to claim 17, wherein the first end of at least one of the male coupling member and female coupling member further comprises a hose connector.

20. A magnetic quick connect according to claim 19, further comprising a removable hose collar including a tubular receiving hole sized to receive the hose connector and a hose therethrough when the hose connector is connected to a hose.

21. A magnetic quick connect according to claim 20, wherein an annular channel is included in the coupling member that comprises the hose collar, and the hose collar includes an annular extension at one end sized to be inserted within the annular channel.

22. A magnetic quick connect according to claim 21, wherein the annular extension is sized to provide an interference fit with the annular channel.

23. A magnetic quick connect according to claim 14, wherein the first collar comprises a body of revolution having a first diameter at the surface of the male coupling member that abuts the female coupling member and a second diameter that is greater than the first diameter at a first location rearward of the abutting surface.

24. A magnetic quick connect according to claim 23, wherein the first collar further has a third diameter at a second location rearward of the first location, where the third diameter is greater than the first diameter, but less than the second diameter.

25. A magnetic quick connect according to claim 24, wherein the diameter of the collar transitions smoothly from the first diameter to the second diameter and from the second diameter to the third diameter.

26. A magnetic quick connect according to claim 1, wherein the first end of at least one of the male coupling member and female coupling member comprises a hose connector.

27. A magnetic quick connect according to claim 26, wherein the hose connector comprises a barbed hose connector.

28. A magnetic quick connect according to claim 27, further comprising a removable hose collar including a tubular receiving hole sized to receive the hose connector and a hose therethrough when the hose connector is connected to a hose.

29. A magnetic quick connect according to claim 1, wherein the O-ring forms a fluid-tight seal between the protrusion and the protrusion mating surface when the male and female coupling members are coupled together.

30. A magnetic quick connect according to claim 1, wherein the O-ring forms a liquid-tight seal between the protrusion and the protrusion mating surface when the male and female coupling members are coupled together.

B. Fluid Delivery System for a Hydration System

The following exemplary claims provide an illustrative example of the scope of claims that may be presented with respect to the fluid delivery system for a hydration system described herein.

1. A fluid delivery system for a hydration system, the fluid delivery system comprising:
  a fluid delivery path having a proximal end adapted to be attached to a fluid reservoir so as to establish fluid communication between the fluid delivery path and the fluid reservoir;
  a magnetic quick connect interposed in the fluid delivery path.

2. A fluid delivery system according to claim 1, further comprising a connector at the proximal end of the fluid delivery path for connecting the fluid delivery path to a fluid reservoir.

3. A fluid delivery system according to claim 2, wherein the connector is a male or female member of a mechanical quick connect.

4. A fluid delivery system according to claim 1, wherein the fluid path is a fluid delivery path for delivering fluid from a portable fluid reservoir to a user's mouth.

5. A fluid delivery system according to claim 4, wherein a distal end of the fluid delivery path is included in a headset.

6. A fluid delivery system according to claim 5, wherein the headset further includes a support structure configured to support the headset on a headgear adapted to be worn on a user's head.

7. A fluid delivery system according to claim 6, wherein the support structure is (i) configured to attach to the headgear and support the headset on the headgear once attached. (ii) attached to the headgear, or (iii) at least partially formed integral with the headgear.

8. A fluid delivery system according to claim 6, wherein the support structure comprises a mounting bracket and the mounting bracket is (i) attached to the headgear, or (ii) configured to attach to the headgear.

9. A fluid delivery system according to claim 6, wherein the proximal end of the headset comprises the magnetic quick connect.

10. A fluid delivery system according to claim 9, wherein:
  the magnetic quick connect comprises a male coupling member and a female coupling member;
  the fluid path between the proximal end and an upstream end of the magnetic quick connect comprises a hose; and
  the hose is configured so that when the proximal end is connected to a fluid reservoir and a user is wearing the headset or when a user is wearing headgear to which the headset is mounted turns his or her head it does not cause the coupling members of the magnetic quick connect to uncouple from one another.

11. A fluid delivery system according to claim 10, wherein the hose has a Shore Durometer hardness in the range of about 50 A to 70 A on the Shore A scale.

12. A fluid delivery system according to claim 9, wherein the magnetic quick connect comprises a male coupling member and a female coupling member, and an axial pull force that is greater than 48 ounce-force and less than 128 ounce-force between the male coupling member and female coupling member is required to decouple the coupling members in the axial direction.

13. A fluid delivery system according to claim 12, wherein the male coupling member and female coupling member may also be decoupled by pivoting one coupling member relative to the other coupling member through the application of a torque that is in the range of about 16 ounce-inches to 72 ounce-inches to the pivoted coupling member.

14. A fluid delivery system according to claim 13, wherein the pivoted coupling member comprises a lever arm of greater than or equal to about 1.0 inches and less than or equal to about 2 inches from the pivot point.

15. A fluid delivery system according to claim 6, wherein the support structure is configured to support the headset on the headgear so that when the headgear is worn on a user's head at least a portion of the magnetic quick connect will be disposed behind the user's ear.

16. A fluid delivery system according to claim 15, wherein the headgear is a helmet.

17. A fluid delivery system according to claim 3, wherein a pump is interposed in the fluid delivery path between the connector at the proximal end and the magnetic quick connect.

18. A fluid delivery system according to claim 17, wherein the male or female member of the mechanical quick connect is configured to couple with a mating member on a portable fluid reservoir.

19. A fluid delivery system according to claim 18, wherein the male or female member of the mechanical quick connect is mounted in a pump housing disposed around the pump and connector, and the housing is shaped such that the mounted male or female member can still be coupled with, and decoupled from, a mating member of the mechanical quick connect.

C. Kit for Forming a Fluid Delivery System

The following exemplary claims provide an illustrative example of the scope of claims that may be presented with respect to the kit for forming a fluid delivery system for a hydration system that is described herein.

1. A kit for forming a fluid delivery system for a hydration system, the kit comprising:
a magnetic quick connect comprising a male coupling member and a female coupling member;
at least one of the male coupling member and female coupling member having a mechanical connector designed to connect to a drink tube of a hydration system;
instructions describing how to interpose the magnetic quick connect in a fluid path that is in communication with a reservoir of a hydration system.

2. A kit according to claim 1, wherein the mechanical connector comprises a barbed hose connector.

3. A kit according to claim 2, further comprising:
a drink tube having a distal end sized to connect to the barbed hose connector;
a pump housing, comprising first coupling member of a mechanical quick connect disposed at a distal end of the pump housing, a second coupling member of a mechanical quick connect disposed at a proximal end of the pump housing, a fluid path extending between the first coupling member and second coupling member, and a pump enclosed within the pump housing and interposed in the fluid path; and
a third coupling member disposed at a proximal end of the drink tube for connecting to the first coupling member and establishing fluid communication between the fluid path extending between the first and second coupling members and the drink tube; wherein
the housing is shaped such that the second coupling member can be coupled with, and decoupled from, a mating coupling member provided on a portable hydration reservoir.

4. A kit according to claim 3, further comprising a headset, wherein the proximal end of the headset comprises the magnetic quick connect, and wherein one of the male coupling member and female coupling member is an upstream member and the other is a downstream member, and the upstream member comprises the barbed hose connector.

5. A kit according to claim 4, wherein the headset further includes further includes a support structure configured to support the headset on a headgear adapted to be worn on a user's head.

6. A kit according to claim 5, wherein the support structure is (i) configured to attach to the headgear and support the headset on the headgear once attached, (ii) attached to the headgear, or (iii) at least partially formed integral with the headgear.

7. A kit according to claim 5, wherein the support structure comprises a mounting bracket that is (i) attached to the headgear, or (ii) configured to attach to the headgear.

8. A kit according to claim 5, wherein the drink tube is configured so that when (i) the third coupling member is coupled to the first coupling member, (ii) the second coupling member is coupled to a mating coupling member of a fluid reservoir. (iii) the distal end of the drink tube is connected to the barbed hose connector, and (iv) a user is wearing the headgear on which the headset is supported turns his or her head, the coupling members of the magnetic quick connect do not uncouple from one another.

9. A kit according to claim 8, wherein the drink tube has a Shore Durometer hardness in the range of about 50 A to 70 A on the Shore A scale.

10. A kit according to claim 1, wherein an axial pull force that is greater than 48 ounce-force and less than 128 ounce-force between the male coupling member and female coupling member is required to decouple the coupling members in the axial direction.

11. A kit according to claim 10, wherein the male coupling member and female coupling member may also be decoupled by pivoting one coupling member relative to the other coupling member through the application of a torque that is in the range of about 16 ounce-inches to 72 ounce-inches to the pivoted coupling member.

12. A kit according to claim 11, wherein the pivoted coupling member comprises a lever arm of greater than or equal to about 1.0 inches and less than or equal to about 2 inches from the pivot point.

13. A kit according to claim 5, wherein the support structure is configured to support the headset on the headgear so that when the headgear is worn on a user's head at least a portion of the magnetic quick connect will be disposed behind the user's ear.

14. A kit according to claim 13, wherein the headgear is a helmet.

15. A kit according to claim 14, wherein at least a portion of the support structure is formed integral with the helmet.

16. A kit for a fluid delivery system, the kit comprising:
- a magnetic quick connect comprising a first and second magnetic coupling members designed to magnetically couple with one another at first mating ends so as to bring the first and second coupling members in fluid communication with one another, each coupling member having a mechanical connector at a second end designed to connect to a component of a fluid communication path;
- a magnetic connector rest comprising a landing pad and a first magnetic material supported by the landing pad, and wherein the landing pad and/or first magnetic material define a mating surface configured to mate with a mating end of one of the first magnetic coupling member; and
- a base coupled to the landing pad and configured to be removably secured to a desired structure.

17. A kit for a fluid delivery system, wherein the first magnetic material is disposed on the landing pad so that when the mating end of the first magnetic coupling member is brought into proximity with the landing pad, an attractive force between the first magnetic material and a second magnetic material included in the first magnetic coupling member will cause the mating end of the first magnetic coupling member to mate with the mating surface of the landing pad and detachably hold the first magnetic coupling member against the mating surface.

D. Headset Claims

The following exemplary claims provide an illustrative example of the scope of claims that may be presented with respect to the headset described herein.

1. A headset for use in a hydration system including a fluid reservoir and an extended length of a drink tube that is in fluid communication with the fluid reservoir at a proximal end, the headset comprising:
- a fluid conduit having a fluid inlet port at one end and a fluid outlet port at a second end, the fluid inlet port comprising a connector adapted to permit the fluid conduit to be detachably connected to a distal end of a drink tube of a hydration system so that the fluid conduit is in fluid communication with the drink tube;
- a first magnetic quick connect comprising a male member and a female member, the first magnetic quick connect defining a portion of the fluid conduit, wherein one of the male member and female member is an upstream member and the other is a downstream member; and
- a support structure configured to support the first magnetic quick connect and at least a portion of the fluid conduit on a headgear adapted to be worn on a user's head.

2. A headset according to claim 1, wherein the support structure is (i) configured to attach to the headgear and support the headset on the headgear once attached, (ii) attached to the headgear, or (iii) at least partially formed integral with the headgear.

3. A headset according to claim 1, wherein the support structure comprises a mounting bracket.

4. A headset for a hydration system according to claim 1, wherein the upstream member of the first magnetic quick connect includes the fluid inlet port.

5. A headset for a hydration system according to claim 1, wherein the fluid inlet port comprises a hose connector formed in the upstream member of the first magnetic quick connect.

6. A headset for a hydration system according to claim 5, wherein the hose connector comprises a barbed hose connector.

7. A headset for a hydration system according to claim 4, further comprising a second magnetic quick connect defining a portion of the fluid conduit downstream of the first magnetic quick connect, the second magnetic quick connect comprising a male member and a female member, one of which is an upstream member and one of which is a downstream member.

8. A headset for a hydration system according to claim 7, wherein the headset further comprises a detachable mouthpiece, a first end of the detachable mouthpiece assembly comprises the downstream member of the second magnetic quick connect, and the fluid outlet port is provided at a second end of the detachable mouthpiece assembly.

9. A headset for a hydration system according to claim 8, wherein the fluid outlet port is provided in a detachable mouthpiece of the mouthpiece assembly.

10. A headset for a hydration system according to claim 9, wherein the detachable mouthpiece comprises a bite-valve.

11. A headset for a hydration system according to claim 9, wherein the detachable mouthpiece comprises a nozzle.

12. A headset for a hydration system according to claim 7, further comprising a valve interposed in the fluid conduit between the first magnetic quick connect and second magnetic quick connect.

13. A headset for a hydration system according to claim 12, wherein the valve comprises a check valve.

14. A headset for a hydration system according to claim 7, further comprising a valve interposed in the fluid conduit between the inlet port and a downstream end of the upstream member of the first magnetic quick connect.

15. A headset for a hydration system according to claim 1, wherein at least a portion of the fluid conduit is adjustable to facilitate positioning of the fluid outlet port proximate to a user's mouth.

16. A headset for a hydration system according to claim 1, wherein the headgear comprises a head bracket mount adapted to be worn on a user's head and the support structure is attached to the head bracket mount.

17. A headset for a hydration system according to claim 16, wherein the head bracket mount includes two opposing support members connected together by a resilient U-shaped spring member, wherein when the two opposing support members are pulled away from one another, the U-shaped spring member produces a biasing force that tends to bias the opposing support members in a direction toward one another.

18. A headset for a hydration system according to claim 17, wherein the head bracket mount is configured so that when it is worn on a user's head the two opposing support members contact opposite sides of the user's head.

19. A headset for a hydration system according to claim 17, wherein the head bracket mount is configured so that when it is worn on a user's head the two opposing support members contact opposite sides of the user's head and the U-shaped spring member wraps around the base of the user's skull.

20. A headset for a hydration system according to claim 19, further comprising a neck pad disposed about at least a middle portion of the U-shaped spring member.

21. A headset for a hydration system according to claim 16, wherein the support structure comprises a mounting bracket.

22. A headset for a hydration system according to claim 1, wherein the support structure is configured to support the first magnetic quick connect on the headgear so that when the headgear is worn by a user at least a portion of the first magnetic quick connect will be disposed behind the user's ear.

23. A headset for a hydration system according to claim 22, wherein the support structure is configured so that when the headgear is worn by a user, the upstream member of the first magnetic quick connect will be disposed behind the user's ear.

24. A headset for a hydration system according to claim 22, wherein the headgear comprises a helmet.

25. A headset for a hydration system according to claim 24, wherein at least a portion of the support structure is formed integral with the helmet.

26. A headset for a hydration system according to claim 24, wherein the support structure comprises a mounting bracket.

27. A headset for a hydration system according to claim 4, wherein the support structure is configured so that when the headgear is worn by a user at least a portion of the first magnetic quick connect will be disposed behind the user's ear.

28. A headset for a hydration system according to claim 5, wherein at least a portion of the fluid conduit downstream of the first magnetic quick connect comprises a flexible tube.

29. A headset for a hydration system according to claim 28, further comprising an adjustable support that is arranged to support the flexible tube and configured to permit positioning of the fluid outlet port proximate a user's mouth.

30. A headset for a hydration system according to claim 29, wherein the adjustable support comprises an adjustable frame.

31. A headset for a hydration system according to claim 29, wherein the fluid outlet port comprises a nozzle.

32. A headset for a hydration system according to claim 1, wherein the support structure is configured to attach to the headgear so that when the headgear is worn by a user at least a portion of the first magnetic quick connect will be disposed behind the user's ear.

33. A headset for a hydration system according to claim 32, wherein the headgear is a helmet.

34. A headset for a hydration system according to claim 32, wherein the support structure comprises a mounting bracket.

35. A headset for a hydration system according to claim 9, wherein the support structure is configured to attach to the headgear so that when the headgear is worn by a user the first magnetic quick connect will be disposed behind the user's ear.

36. A headset for a hydration system according to claim 35, wherein the headgear is a helmet.

37. A headset for a hydration system according to claim 36, wherein the support structure comprises a mounting bracket.

38. A headset for a hydration system according to claim 36, wherein the mouthpiece assembly comprises a shaped conduit that is configured to extend below a chin guard of a full-face helmet when the headset is mounted to a full-face helmet and position the fluid outlet port so that it is proximate to and directed toward a user's mouth when wearing the helmet.

39. A headset for a hydration system according to claim 36, wherein an axial pull force that is greater than 32 ounce-force and less than 54 ounce-force between the male member and female member of the second magnetic quick connect is required to decouple the male and female members of the second magnetic quick connect in the axial direction.

40. A headset for a hydration system according to claim 39, wherein the male member and female member of the second magnetic quick connect may also be decoupled by pivoting the downstream member relative to the upstream member through the application of a torque to the detachable mouthpiece that is in the range of about 20 ounce-inches to 36 ounce-inches.

41. A headset for a hydration system according to claim 1, wherein an axial pull force that is greater than 64 ounce-force and less than 96 ounce-force between the male member and female member is required to decouple the male and female members of the first magnetic quick connect in the axial direction.

42. A headset for a hydration system according to claim 41, wherein the male member and female member of the first magnetic quick connect may also be decoupled by pivoting one member relative to the other member through the application of a torque that is in the range of about 35 ounce-inches to 64 ounce-inches to the pivoted coupling member.

43. A headset for a hydration system according to claim 42, wherein the pivoted member comprises a lever arm of greater than or equal to about 1.0 inches and less than or equal to about 2 inches from the pivot point.

44. A headset for a hydration system according to claim 9, wherein:
the support structure comprises a helmet mount, the helmet mount being elongated in one direction and shaped to generally match the curvature of a helmet so that in a top view of the helmet mount the centerline of the helmet mount curves inwardly from a proximal end of the helmet mount to a distal end of the helmet mount, the helmet mount also being configured to hold the downstream member of the first magnetic quick connect at the proximal end of the helmet mount and the upstream member of the second magnetic quick connect at the distal end of the helmet mount; and
the headset further comprises a fluid conduit extending between the downstream member of the first magnetic quick connect and the upstream member of the second magnetic quick connect.

45. A headset for a hydration system according to claim 44, wherein the support structure further comprises at least one adhesive backed helmet pad, the at least one adhesive backed helmet pad being configured to (i) adhesively attach to a helmet, and (ii) have the helmet mount attach thereto after being attached to a helmet.

46. A headset for a hydration system according to claim 45, wherein the mouthpiece assembly comprises a shaped conduit that is configured to extend below a chin guard of a full-face helmet when the headset is mounted to a full-face helmet and position the fluid outlet port so that it is proximate to and directed toward a user's mouth when wearing the helmet.

47. A headset for a hydration system according to claim 5, wherein the support structure is configured so that when the headgear is worn by a user at least a portion of the first magnetic quick connect will be disposed behind the user's ear.

48. A headset for a hydration system according to claim 47, wherein at least a portion of the fluid conduit downstream of the first magnetic quick connect comprises a flexible tube.

49. A headset for a hydration system according to claim 48, further comprising an adjustable support connected to the flexible tube and configured to permit positioning of the fluid outlet port proximate a user's mouth.

50. A headset for a hydration system according to claim 49, wherein the adjustable support comprises an adjustable frame.

51. A headset for a hydration system according to claim 49, wherein the fluid outlet port comprises a nozzle.

52. A headset for a hydration system according to claim 47, wherein the headgear comprises a helmet.

53. A headset for a hydration system according to claim 52, wherein at least a portion of the support structure is formed integral with the helmet.

54. A headset for a hydration system according to claim 5, wherein the support structure is configured so that when the headgear is worn by a user at least the upstream member of the first magnetic quick connect will be disposed behind the user's ear.

55. A headset for a hydration system according to claim 1, wherein at least a portion of support structure is formed integral with the headgear.

56. A headset for a hydration system according to claim 55, wherein the headgear comprises a helmet or a hardhat.

E. Detachable Mouthpiece Assembly Claims

The following exemplary claims provide an illustrative example of the scope of claims that may be presented with respect to the detachable mouthpiece assembly described herein.

1. A detachable mouthpiece assembly for a headset of a hydration system including a fluid reservoir and an extended length of a drink tube that is in fluid communication with the fluid reservoir at a proximal end and a fluid path extending through the headset at a distal end, the detachable mouthpiece comprising:
   a fluid conduit extending from an entrance port to an outlet port;
   a downstream coupling member of a magnetic quick connect defining the entrance port and at least a portion of the fluid conduit, the downstream coupling member configured to couple with a mating upstream coupling member disposed at a distal end of a helmet mount of the headset so that when coupled the fluid conduit is in fluid communication with the fluid path.

2. A detachable mouthpiece assembly for a hydration system according to claim 1, further comprising a detachable mouthpiece at the distal end of the fluid conduit, wherein the fluid outlet port is provided in the detachable mouthpiece.

3. A detachable mouthpiece assembly according to claim 2, wherein the detachable mouthpiece comprises a bite-valve.

4. A detachable mouthpiece assembly according to claim 2, wherein the detachable mouthpiece comprises a nozzle.

5. A detachable mouthpiece assembly according to claim 2, wherein the detachable mouthpiece is adjustable so that the angle and/or height of fluid outlet port can be adjusted relative to the coupling member.

6. A detachable mouthpiece assembly according to claim 5, wherein the downstream coupling member is a female coupling member.

7. A detachable mouthpiece assembly according to claim 1, wherein the downstream coupling member is a female coupling member.

8. A detachable mouthpiece assembly according to claim 1, wherein the downstream coupling member includes an abutting surface with an indexing feature, and the abutting surface is configured to abut a surface of the mating upstream coupling member that has a matching indexing feature when the downstream coupling member and mating upstream coupling member are coupled together.

9. A detachable mouthpiece assembly according to claim 1, further comprising a shaped conduit defining at least a portion of the fluid conduit distal to the downstream coupling member, wherein the shaped conduit is configured to (i) extend the fluid conduit below a chin guard of a full-face helmet when coupled to the mating upstream coupling member of a headset mounted to a full-face helmet, and (ii) position the fluid outlet port so that it is proximate to and directed toward a user's mouth when wearing the helmet.

10. A detachable mouthpiece assembly according to claim 1, wherein the downstream coupling member is configured so that when the downstream coupling member is coupled to a mating upstream coupling member, an axial pull force that is greater than 32 ounce-force and less than 54 ounce-force is required to decouple the coupling members in the axial direction.

11. A detachable mouthpiece assembly according to claim 10, wherein the downstream and mating upstream coupling members may also be decoupled by pivoting the downstream coupling member relative to the mating upstream coupling member through the application of a torque to the detachable mouthpiece that is in the range of about 20 ounce-inches to 36 ounce-inches.

12. A detachable mouthpiece assembly according to claim 1, wherein the downstream coupling member comprises a female coupling member, and the female coupling member comprises:
   a first end;
   a second mating end, the second mating end having an outer cross-sectional profile; and
   a fluid communication path extending from the first end to the second mating end of the female coupling member; and
   a magnetic material disposed about the fluid communication path in the female coupling member proximate the second mating end; wherein
   the second mating end of the female connector includes a protrusion mating surface that defines a protrusion receiving area within the second mating end of the female coupling member, the protrusion mating surface shaped to match an outer surface of a protrusion on the mating upstream coupling member so that when the female coupling member and mating upstream coupling member are coupled together, the protrusion is received within the protrusion receiving area.

13. A detachable mouthpiece assembly according to claim 12, wherein the magnetic material is disposed about the second mating end of the female coupling member so that when the female coupling member and mating coupling member are coupled together, they are detachably held together by an attractive force between the magnetic material and a mating magnetic material included in the mating coupling member.

14. A detachable mouthpiece assembly according to claim 13, wherein the magnetic material comprises a material selected from the group consisting of a ferromagnetic material and ferrimagnetic material.

15. A detachable mouthpiece assembly according to claim 14, wherein the magnetic material comprises a permanent magnet.

16. A detachable mouthpiece assembly according to claim 13, wherein the female coupling member is configured so that when the female coupling member is coupled to the mating upstream coupling member, an axial pull force that is greater than 32 ounce-force and less than 54 ounce-force is required to decouple the coupling members in the axial direction.

17. A detachable mouthpiece assembly according to claim 16, wherein the female and mating upstream coupling members may also be decoupled by pivoting the female coupling member relative to the mating upstream coupling member through the application of a torque to the detachable mouthpiece that is in the range of about 20 ounce-inches to 36 ounce-inches.

18. A detachable mouthpiece assembly according to claim 12, wherein the female coupling member further comprises a collar disposed at the second mating end of the female coupling member, and the collar defines at least part of a surface of the coupling member that abuts the mating upstream coupling member when the coupling members are coupled together.

19. A detachable mouthpiece assembly according to claim 18, wherein the magnetic material is disposed within the collar.

20. A detachable mouthpiece assembly according to claim 19, wherein the magnetic material is ring-shaped.

21. A detachable mouthpiece assembly according to claim 20, wherein the collar defines an annular channel that is open away from the abutting surface of the collars.

22. A detachable mouthpiece assembly according to claim 21, wherein the magnetic material is disposed within the annular channel defined by the collar.

23. A detachable mouthpiece assembly according to claim 13, wherein when the female coupling member and a mating upstream coupling member are coupled together a fluid-tight seal is formed between the protrusion and the protrusion mating surface.

24. A detachable mouthpiece assembly according to claim 13, wherein when the female coupling member and a mating upstream coupling member are coupled together a liquid-tight seal is formed between the protrusion and the protrusion mating surface.

F. Wireless Actuation System Claims

The following exemplary claims provide an illustrative example of the scope of claims that may be presented with respect to the wireless actuation system described herein.

1. A wireless actuation system for use with a hydration system including a fluid reservoir, a wirelessly controlled pump in fluid communication with the reservoir, and an extended length of a drink tube that is in fluid communication with the fluid reservoir and pump at a proximal end and an exit port at a distal end, the actuation system comprising:
a microswitch;
a cable electrically connected to the microswitch at one end and including an electrical connector at a second end;
a first mounting means provided proximate the microswitch, the first mounting means configured to attach the microswitch on a portion of a steering mechanism of a vehicle that is controlled by a user's hand;
a wireless transmitter including a second mounting means attached thereto for removably attaching the wireless transmitter to the steering mechanism of a vehicle and a mating electrical connector for removably receiving the electrical connector, the wireless transmitter being configured to transmit a first signal when the connector is connected to the mating connector and the microswitch is closed.

2. A wireless actuation system according to claim 1, wherein the first mounting means is further configured to attach the microswitch on the steering mechanism in a location proximate to where a user's hand would grip the steering mechanism to steer the vehicle and the microswitch can be operated without the hand of the user being removed from the steering mechanism.

3. A wireless actuation system according to claim 1, wherein the first mounting means comprises a pair of cable ties and an elongated piece of heat shrink tubing.

4. A wireless actuation system according to claim 3, wherein the heat shrink tubing is disposed around the microswitch and a portion of the cable, and wherein the heat shrink tubing includes a pair of slits on opposite sides of the microswitch, each slit extending in an axial direction of the heat shrink tubing, and each cable tie extending through one of slits.

5. A wireless actuation system according to claim 1, wherein the second mounting means comprises a pair of straps, each strap attached to opposite sides of the wireless transmitter at one end, and the other end of each of the straps comprising a hook and a loop fastener, respectively.

6. A wireless actuation system according to claim 1, wherein the wireless transmitter comprises a Bluetooth transmitter.

7. A wireless actuation system according to claim 1, wherein the wireless transmitter comprises an on/off switch.

8. A wireless actuation system according to claim 7, wherein the wireless transmitter further comprises an indicator light, the indicator light being configured to signal whether the first signal is being transmitted.

9. A wireless actuation system according to claim 1, wherein the wireless transmitter is configured to transmit a second signal when the connector is connected to the mating connector and the microswitch is open.

10. A wireless actuation system according to claim 1, wherein the wireless transmitter has a single button, wherein the wireless transmitter is configured to transmit the first signal when the single button is depressed.

11. A wireless actuation system according to claim 10, wherein the wireless transmitter is configured to transmit a second signal when the single button is not depressed, and when the connector is connected to the mating connector, and the microswitch is open.

12. A wireless actuation system according to claim 11, wherein the wireless transmitter is configured to transmit a second signal when the single button is not depressed, and when the connector is not connected to the mating connector.

13. A wireless actuation system according to claim 1, wherein the wireless transmitter has a first button and a second button, wherein when the connector is connected to the mating connector and the microswitch is open, the wireless transmitter is configured to transmit a first signal when a first button is depressed, a second signal when neither the first or second button is depressed, and a third signal when the second button is depressed.

14. A wireless actuation system according to claim 13, wherein when the connector is disconnected from the mating connector, the wireless transmitter is configured to transmit the first signal when the first button is depressed, the second signal when neither the first or second button is depressed, and the third signal when the second button is depressed.

15. A wireless actuation system according to claim 1, wherein the wireless transmitter has a first button, a second button, and a third button, wherein when the connector is connected to the mating connector and the microswitch is open, the wireless transmitter is configured to transmit a first signal when a first button is depressed, a second signal when none of the first, second, or third button is depressed, a third signal when the second button is depressed, and a fourth signal when the third button is depressed.

16. A wireless actuation system according to claim 15, wherein when the connector is disconnected from the mating connector, the wireless transmitter is configured to transmit the first signal when the first button is depressed, the second signal when neither the first, second, or third button is depressed, the third signal when the second button is depressed, and the fourth signal when the third button is depressed.

17. A wireless actuation system according to claim 1, wherein the wireless transmitter includes a keychain loop.

G. Vehicle with Personal Hydration System Claims

The following exemplary claims provide an illustrative example of the scope of claims that may be presented with respect to the vehicles described herein.

1. A vehicle comprising:
   a frame;
   a powertrain supported by the frame, and including a final drive mechanism.
   a hand operated steering mechanism supported by the frame;
   a fluid reservoir supported by the frame;
   a fluid communication path connected at a proximal end to the fluid reservoir and having an outlet port at its distal end, the fluid communication path having a length sufficient to extend from the reservoir to a location proximate a user's mouth;
   a pump interposed in the fluid communication path;
   a microswitch operably connected to the pump, the microswitch disposed on the steering mechanism in a location sufficiently proximate to where a user's hand would grip the steering mechanism to steer the vehicle so that the microswitch can be operated without a user removing his or her hand from the steering mechanism.

2. A vehicle according to claim 1, further comprising:
   a rust mounting means provided proximate the microswitch, the first mounting means mounting the microswitch to the steering mechanism.

3. A vehicle according to claim 2, wherein the first mounting means comprises a pair of cable ties and an elongated piece of heat shrink tubing.

4. A vehicle according to claim 3, wherein the heat shrink tubing is disposed around the microswitch and a portion of the cable, and wherein the heat shrink tubing includes a pair of slits on opposite sides of the microswitch, each slit extending in an axial direction of the heat shrink tubing, and each cable tie extends through one of slits and encircles a portion of the steering mechanism.

5. A vehicle according to claim 1, further comprising:
   a cable electrically connected to the microswitch at one end and including an electrical connector at a second end; and
   a wireless transmitter including a second mounting means attached thereto and a mating electrical connector for removably connecting to the electrical connector, the second mounting means removably attaching the wireless transmitter to the steering mechanism of the vehicle, and the wireless transmitter being configured to transmit a first signal when the connector is connected to the mating connector and the microswitch is closed.

6. A vehicle according to claim 5, wherein the second mounting means comprises a pair of straps, each strap attached to opposite sides of the wireless transmitter at one end, and the other end of each of the straps comprising a hook and a loop fastener, respectively.

7. A vehicle according to claim 5, wherein the wireless transmitter comprises a Blue Tooth transmitter.

8. A vehicle according to claim 5, wherein the wireless transmitter comprises an on/off switch.

9. A vehicle according to claim 8, wherein the wireless transmitter further comprises an indicator light, the indicator light being configured to signal whether the first signal is being transmitted.

10. A vehicle according to claim 5, wherein the wireless transmitter is configured to transmit a second signal when the connector is connected to the mating connector and the microswitch is open.

11. A vehicle according to claim 5, wherein the wireless transmitter has a single button, wherein the wireless transmitter is configured to transmit the first signal when the single button is depressed.

12. A vehicle according to claim 11, wherein the wireless transmitter is configured to transmit a second signal when the single button is not depressed, and the microswitch is open when the connector is connected to the mating connector.

13. A vehicle according to claim 12, wherein the wireless transmitter is configured to transmit the second signal when the single button is not depressed and the connector is not connected to the mating connector.

14. A vehicle according to claim 5, wherein the wireless transmitter has a first button and a second button, and wherein when the connector is connected to the mating connector and the microswitch is open, the wireless transmitter is configured to transmit a first signal when a first button is depressed, a second signal when neither the first button or second button is depressed, and a third signal when the second button is depressed.

15. A vehicle according to claim 14, wherein when the connector is disconnected from the mating connector, the wireless transmitter is configured to transmit the first signal when the first button is depressed, the second signal when neither the first button or second button is depressed, and the third signal when the second button is depressed.

16. A vehicle according to claim 5, wherein the wireless transmitter has a first button, a second button, and a third button, and wherein when the connector is connected to the mating connector and the microswitch is open, the wireless transmitter is configured to transmit a first signal when a first button is depressed, a second signal when none of the first, second, or third buttons are depressed, a third signal when the second button is depressed, and a fourth signal when the third button is depressed.

17. A vehicle according to claim 16, wherein when the connector is disconnected from the mating connector, the wireless transmitter is configured to transmit the first signal when the first button is depressed, the second signal when neither the first, second, or third button is depressed, the third signal when the second button is depressed, and the fourth signal when the third button is depressed.

18. A vehicle according to claim 5, further comprising handlebar, and wherein the microswitch and the transmitter are mounted to the handlebar.

19. A vehicle according to claim 18, further comprising a clutch lever attached to the handlebar and the microswitch is mounted on the clutch lever.

20. A vehicle according to claim 19, wherein the microswitch is mounted on the clutch lever in a location that it can be operated with an index finger of a left hand of a user without removing his or her left hand from a hand grip.

21. A vehicle according to claim 5, further comprising a steering wheel, and wherein the microswitch is mounted to the steering wheel and the transmitter is mounted to a rear side of a hub of the steering wheel.

22. A vehicle according to claim 5, further comprising a steering wheel, and wherein the microswitch is mounted to a front side of a hub of the steering wheel, and wherein the transmitter is mounted to a rear side of the hub.

H. Magnetic Connector Rest Claims

The following exemplary claims provide an illustrative example of the scope of claims that may be presented with respect to the magnetic connector rest described herein.

1. A magnetic connector rest for a portable hydration system including a fluid reservoir, a headset including the magnetic quick connect at a proximal end of the headset, and a drink tube that is in fluid communication with the fluid reservoir at a proximal end of the drink tube and a fluid path extending through the headset at a distal end of the drink tube, where the magnetic quick connect comprises an upstream coupling member that includes a hose connector at a proximal end, a downstream coupling member that detachably couples with the upstream coupling member through a magnetic force, and the drink tube is in selective fluid communication with the fluid path extending through the headset by being connected to the hose connector provided at the proximal end of the upstream coupling member, the magnetic connector rest comprising:
 a landing pad;
 a first magnetic material supported by the landing pad, the landing pad and/or first magnetic material defining a mating surface configured to mate with a mating end of the upstream coupling member; and
 a base coupled to the landing pad and configured to be removably secured to a desired structure; wherein:
 the first magnetic material is disposed on the landing pad so that when the upstream coupling member is brought into proximity with the landing pad, an attractive force between the first magnetic material and a second magnetic material included in the upstream coupling member will cause the mating end of the upstream coupling member to mate with the mating surface of the landing pad and detachably hold the upstream coupling member against the mating surface.

2. A magnetic connector rest for a portable hydration system according to claim 1, wherein the mating surface is configured to protect the mating end of the upstream coupling member from dirt and other debris when mated with the mating surface.

3. A magnetic connector rest for a portable hydration system according to claim 1, wherein the mating surface comprises a shelf with a recess defining a protrusion receiving area, and the first magnetic material is disposed about the recess.

4. A magnetic connector rest for a portable hydration system according to claim 3, wherein the first magnetic material is ring-shaped and the protrusion receiving area extends coaxially through the first magnetic material.

5. A magnetic connector rest for a portable hydration system according to claim 1, wherein the first magnetic material comprises a permanent magnet.

6. A magnetic connector rest for a portable hydration system according to claim 1, wherein the first magnetic material comprise a material selected from the group consisting of a ferromagnetic material and ferrimagnetic material.

7. A magnetic connector rest for a portable hydration system according to claim 6, wherein the first magnetic material is sized so that an axial pull force that is greater than 32 ounce-force and less than 128 ounce-force between the landing pad and the upstream coupling member is required to decouple the upstream coupling member from the mating surface of the landing pad in the axial direction.

8. A magnetic connector rest for a portable hydration system according to claim 6, wherein the first magnetic material is sized so that an axial pull force that is greater than 64 ounce-force and less than 96 ounce-force between the landing pad and the upstream coupling member is required to decouple the upstream coupling member from the mating surface of the landing pad in the axial direction.

9. A magnetic connector rest for a portable hydration system according to claim 6, wherein the first magnetic material is sized so that an axial pull force that is greater than 72 ounce-force and less than 88 ounce-force between the landing pad and the upstream coupling member is required to decouple the upstream coupling member from the mating surface of the landing pad in the axial direction.

10. A magnetic connector rest for a portable hydration system according to claim 7, wherein the upstream coupling member comprises a male coupling member and the mating end includes a protrusion that comprises a body of revolution, and wherein the mating surface comprises a shelf with a recess defining a protrusion receiving area, and the first magnetic material is disposed about the recess.

11. A magnetic connector rest for a portable hydration system according to claim 10, wherein the mating surface is configured so that the distance that the protrusion extends into the protrusion receiving area is less than the minimum diameter of the portion of the protrusion receiving area that receives the protrusion.

12. A magnetic connector rest for a portable hydration system according to claim 11, wherein the first magnetic material is sized so that the upstream coupling member may also be decoupled by pivoting the upstream coupling member relative to the landing pad through the application of a torque that is in the range of about 16 ounce-inches to 72 ounce-inches to the upstream coupling member.

13. A magnetic connector rest for a portable hydration system according to claim 11, wherein the first magnetic material is sized so that the upstream coupling member may also be decoupled by pivoting the upstream coupling member relative to the landing pad through the application of a torque that is in the range of about 35 ounce-inches to 64 ounce-inches to the upstream coupling member.

14. A magnetic connector rest for a portable hydration system according to claim 11, wherein the first magnetic material is sized so that the upstream coupling member may also be decoupled by pivoting the upstream coupling member relative to the landing pad through the application of a torque that is in the range of about 48 ounce-inches to 60 ounce-inches to the upstream coupling member.

15. A magnetic connector rest for a portable hydration system according to claim 10, wherein the mating surface comprises a shelf with a recess defining a protrusion receiving area, and the first magnetic material is disposed about the recess.

16. A magnetic connector rest for a portable hydration system according to claim 1, wherein the base comprises a mounting bracket.

17. A magnetic connector rest for a portable hydration system according to claim 16, wherein the mounting bracket comprises a clip.

18. A magnetic connector rest for a portable hydration system according to claim 17, wherein:
 the clip is generally C-shaped with two opposing resilient arms that are anchored at a common end and include opposing extensions that extend toward one another at their opposite ends;

the opposing resilient arms define a backpack strap receiving area therebetween that can be accessed through an adjustable gap provided between the opposing extensions;

when the opposing resilient arms are in an unbiased state the adjustable gap between the opposing extensions being sized to prevent straps of a predetermined size from accessing the strap receiving area; and when the opposing resilient arms are pulled away from one another, a biasing force tends to bias the opposing resilient arms in a direction toward one another, and the adjustable gap can be made to be of sufficient width to allow straps of the predetermined size to access the strap receiving area so that once a strap of the predetermined size is inserted in the strap receiving area and the opposing arms are no longer pulled away from one another they will clamp onto the strap of the predetermined size.

19. A magnetic connector rest for a portable hydration system according to claim 1, wherein the mating surface comprises a shelf with a mating male or female structural feature for mating with a corresponding female or male structural feature, respectively, on the mating end of the upstream coupling member.

20. A magnetic connector rest for a portable hydration system according to claim 19, wherein the mating surface is configured to protect the mating end of the upstream coupling member from dirt and other debris when mated with the mating surface.

21. A magnetic connector rest for a portable hydration system according to claim 20, wherein the first magnetic material is ring-shaped and the mating feature is arranged coaxial with the first magnetic material.

22. A magnetic connector rest for a portable hydration system according to claim 1, wherein the base comprises a hook or loop fastener strip disposed on the back side of the base for mounting on a corresponding fastener strip disposed on the shoulder strap.

23. A magnetic connector rest for a coupling member of a magnetic quick connect that is connected to a drink tube of a portable hydration system, the magnetic connector rest comprising:
a landing pad;
a first magnetic material supported by the landing pad, the landing pad and/or first magnetic material defining a mating surface configured to mate with a mating end of a coupling member of a magnetic quick connect comprising two coupling members that are detachably coupled together by a magnetic force; and
a base coupled to the landing pad and configured to be removably secured to a desired structure; wherein:
the first magnetic material is disposed on the landing pad so that when the coupling member is brought into proximity with the landing pad, an attractive force between the first magnetic material and a second magnetic material included in the coupling member will cause the mating end of the coupling member to mate with the mating surface of the landing pad and detachably hold the coupling member against the mating surface.

24. A magnetic connector rest for a portable hydration system according to claim 1, wherein the mating surface is configured to protect the mating end of the coupling member from dirt and other debris when mated with the mating surface.

I. Fluid Control Unit Claims

The following exemplary claims provide an illustrative example of the scope of claims that may be presented with respect to the fluid control unit described herein.

1. A fluid control unit of a fluid delivery system for a hydration system, the fluid control unit comprising:
a housing;
a pump disposed within the housing;
a controller operably connected to the pump to control the pump;
a power source in electrical communication with the pump via the controller;
an inlet tube connected to an inlet of the pump at one end and a first coupling member of a mechanical quick connect on the other end; and
an outlet tube connected to an outlet of the pump at one end and a second coupling member of a mechanical quick connect on the other end;
wherein the controller is configured to process one or more command signals received from a wireless transmitter in wireless communication with the controller.

2. A fluid control unit according to claim 1, wherein the first coupling member of the mechanical quick connect comprises a male connector; the housing comprises a recess extending from a bottom wall of the housing to a horizontal support wall; a hose connector of the male connector extends through a hole in the horizontal support wall so that the male connector is disposed on the exterior of the housing and the hose connector of the male connector is disposed on the inside of the housing and the inlet tube is connected thereto.

3. A fluid control unit according to claim 1, wherein the recess is sized to receive an outlet spout of a hydration reservoir bag, where the outlet spout includes a mating female mechanical quick connector disposed at the end of the outlet spout, and wherein the recess is also sized so as to permit a user to access a release on the mating female quick connector when the male connector and mating female connector are connected so as to uncouple them.

It will also be appreciated from reviewing the present disclosure, that it is contemplated that features presented in one exemplary claim set may also be included or claimed in other claim sets.

The reference number list below provides a list of reference numbers used in the figures that accompany the present patent document, the structure or process steps to which they correspond, and the figure in which they first appear.

REFERENCE LIST

Figure 3B:
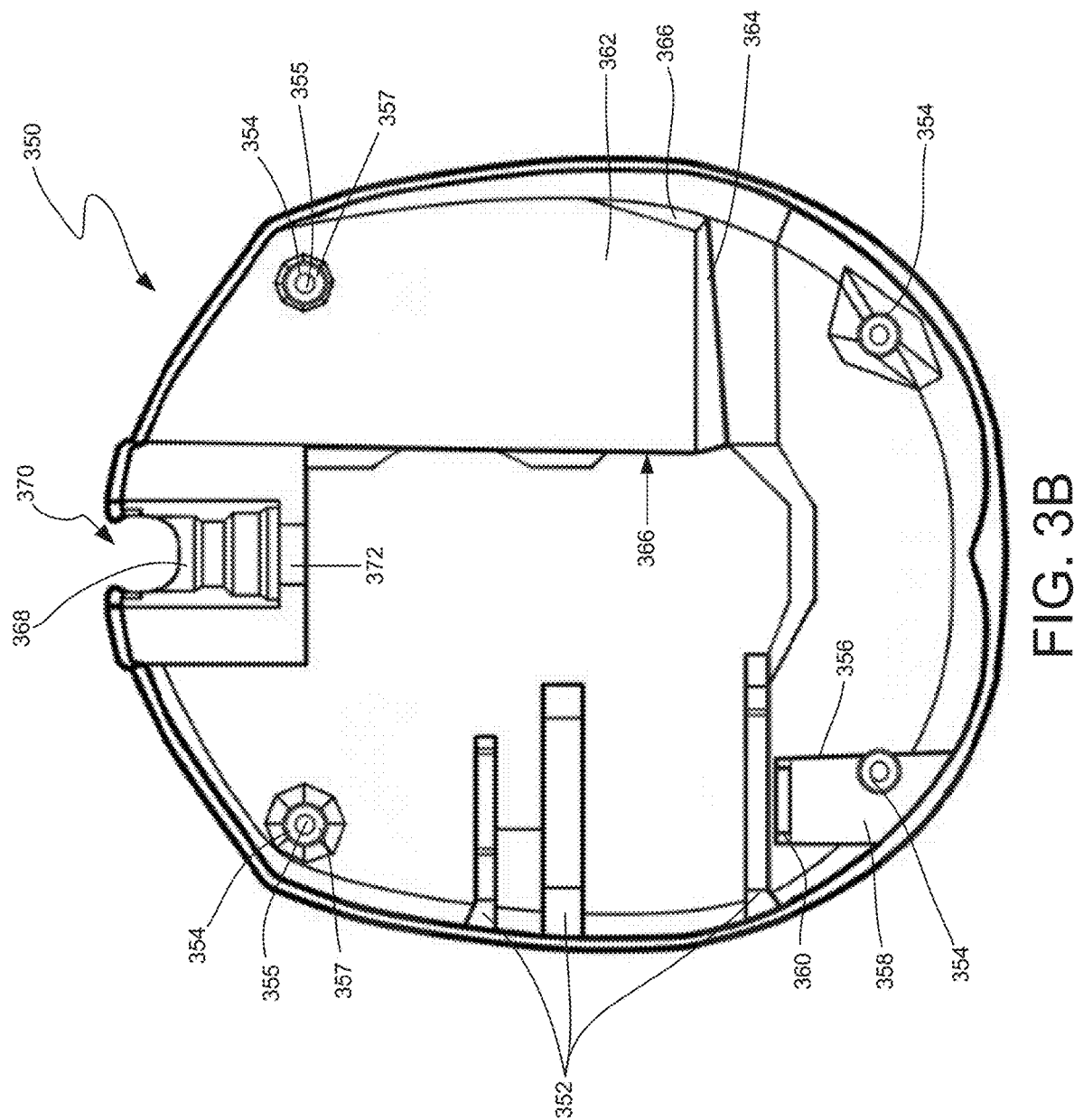
FIG. 3B is a schematic illustration of the inside of the front housing cover of the fluid control unit shown in FIG. 1.

First Used in FIG. 1
90—User
92—Vehicle
93—Bicycle
100—Hydration System
102—Backpack
103—Fluid Delivery System
104—Fluid Reservoir
106—Fluid Control Unit
108—Headset
109—Helmet (Headgear)
110—Mouthpiece Assembly
112—Switch
114—Transmitter (Bluetooth)
116—Dispensing Hose
118—Magnetic Quick Connect
120—Handlebar
122—Steering Mechanism 124—Handlebar Stem
125—Headset
126—Front Fork
127—Steer Tube
128—Head Tube
130—Frame
132—Front Wheel
134—Rear Wheel
136—Fork Blade
138—Fork Crown
140—Wireless Actuation System
First Used in FIG. 2
  202—Fill Cap
  204—Housing (Pump)
  206—Power Source/Battery Cover
  208—Quick Connect (Mechanical)
  210—Quick Connect Release Button
  212—Shoulder Strap
First Used in FIG. 3A
  302—Back Housing Cover
  304—Recessed Area×4 (For Support Standoff)
  306—Pump/Motor Assembly
  308—Mounting Brackets for Motor/Pump Assembly
  310—Inlet Tube (for Control Unit)
  312—Outlet Tube (for Control Unit)
  314—Inlet Male Quick Connector
  316—Mounting Wall (for Male Quick Connector)
  318—Inwardly Recessed Wall (to permit Male Quick Connector to Connect w/Female Connector on fluid reservoir bag)
  320—Barbed Hose Connector (for Male Quick Connector)
  322—Outlet Female Quick Connector
  324—Barbed Hose Connector (for Female Quick Connector)
  326—Support (for Female Quick Connector)
  328—Male Quick Connector (for Dispensing/Drinking Hose)
  330—Barbed Hose Connector (for Male Quick Connector)
  332—Brackets (for receiving mounting legs 412)
  334—Male Coupling Member (Magnetic Quick Connect)
  336—Female Coupling Member (Magnetic Quick Connect)
  338—Hose Collar
  340—Magnetic Quick Connect (for Mouthpiece Assembly)
  342—Male Coupling Member
  344—Female Coupling Member
  346—Mouthpiece
  348—Outlet Port
First Used in FIG. 3B
  350—Front Housing Cover
  352—Mounting Brackets (for Pump/Motor Assembly)
  354—Support Stand Off (×4)
  355—Threaded Hole (×4 can be by an Insert)
  356—Motor Stop
  357—Mating End (of Support Stand Off (×4))
  358—Main Body (of Motor Stop)
  360—Spacer (of Motor Stop)
  362—Inwardly Recessed Wall (for Battery Compartment)
  364—Bottom Wall of Battery Compartment
  366—Side Walls of Battery Compartment
  368—Matching Recess (for Female Quick Connector)
  370—Cutout (for Accessing Release Button)
  372—Hose Recess
First Used in FIG. 4A
  402—Hole (×4 in Back Housing Cover)
  404—Recess (formed by Recessed wall 318)
  407—Back Surface (of Support)
  406—Screws (×4 for attaching to Back Housing Cover to Front Housing Cover)
  408—Circuit Board
  410—Circuit Board Mount
  412—Mounting Legs (of Circuit Board Mount)
  414—Connector (for Pump Motor)
  416—Wires (Pump)
  417—Terminals (for Pump)
  418—Connector (for Power to Circuit Board)
  420—Wires (for Power to Circuit Board)
  422—Battery Compartment
  423—Battery
  424—Battery Recess
  426—Indent (in Power Source Cover)
  450—Magnet (on left side of Power Source Cover)
First Used in FIG. 4B
  428—Controller
  430—Support Boss (for Support 326)
  432—Through Hole (in Mounting Wall 316)
  434—Matching Recess (in Support 326)
  438—Magnets (in bottom wall 364)
  448—Magnets (in right Side Wall 366)
First Used in FIG. 5
  452—Magnet (in left Side Wall 366)
  454—Battery Contacts
  456—Auto Fill Button
First Used in FIG. 6A/6B
  460—Battery Terminals
  462—Magnets (in right side wall of Power Source Cover 206)
  464—Magnets (in bottom wall of Power Source Cover 206)
First Used in FIG. 7A/7B
  702—Centerline (of Headset)
  704—Fluid Conduit
  706—Fluid Inlet Port
  710—Mounting Bracket
  712—First End (of Male Coupling Member 334)
  714—Barbed Hose Connector
  716—Second End (of Male Coupling Member 334)
  718—Fluid Communication Path (in Male Coupling Member)
  720—First Magnetic Material
  722—Protrusion (of Male Coupling Member)
  724—O-ring
  726—First End (of Female Coupling Member 336)
  728—Barbed Hose Connector (on Female Coupling Member)
  730—Second End (of Female Coupling Member 336)
  732—Fluid Communication Path (in Female Coupling Member)
  734—Second Magnetic Material
  736—Protrusion Mating Surface
  738—Check Valve
  740—Double Male Hose Connector
  742—Check Valve (in Male Coupling Member)
  744—Hose
  746—Hose
  748—First End (of Male Coupling Member 342)
  750—Barbed Hose Connector (of Male Coupling Member of 342)
  752—Second End (of Male Coupling Member 342)
  754—Fluid Communication Path (in Male Coupling Member 342)

756—First Magnetic Material
758—Protrusion (of Male Coupling Member)
760—O-ring
762—First End (of Female Coupling Member 344)
764—Connector (on Female Coupling Member)
766—Second End (of Female Coupling Member 344)
768—Fluid Communication Path (in Female Coupling Member 344)
770—Second Magnetic Material
772—Shaped Conduit
774—Helmet Mount
776—Holes
778—Annular Extension (on Hose Collar 338)
First Used in FIG. 7C/7D
  717—Cylindrical Portion of Second End 714.
  731—Cylindrical Portion of Second End 730.
  780—Protrusion Mating Surface (in Female Coupling Member 344)
  789—Channel in Collar 788
First Used in FIG. 7E
  782—Collar of Male Coupling Member 334
  784—Collar of Female Coupling Member 336
  785—Channel in Collar 784
  786—Collar of Male Coupling Member 342
  788—Collar of Female Coupling Member 344
  790—Side Plate
  792—Screws (for attaching side plate)
  793—Threaded holes (for screws 792)
  794—Supports
  796—Helmet Pads (adhesive backed)
  798—Mounting Screws
  799—Mounting Nuts
First Used in FIG. 7F
  783—Channel in Collar 782
  787—Channel in Collar 786
First Used in FIGS. 8A/8B
  802—Flow direction
First Used in FIGS. 10-12
  804—Cable (Connecting Microswitch and Transmitter FOB)
  806—Cable Jack
  808—Heat Shrink Tubing
  810—Cable Ties (Zip Ties)
  812—Slits in Heat Shrink Tubing
  813—Second mounting means
  814—Strap
  816—On/Off Switch
  818—Button
  820—Indicator Light
First Used in FIG. 13
  830—Motorcycle
  832—Hydration System
  833—Fluid Delivery System
  834—Headset (Mirror Image of Headset of 108)
  836—Power Train
  838—Motor
  840—Transmission
  842—Drive Train
  844—Rear Sprocket
  846—Driven Wheel
  848—Swing Arm
  850—Steering Mechanism
  852—Handlebar
  854—Front Fork
  856—Front Wheel
  858—Clutch Lever
First Used in FIG. 14
  860—Transmitter (2 Button)
First Used in FIG. 15
  862—$1^{st}$ Button
  864—$2^{nd}$ Button
  866—Keychain Loop
  868—Hand Grip
First Used in FIG. 16
  870—Car
  871—Helmet
  872—Steering Mechanism
  874—Steering Wheel
  875—Second microswitch
First Used in FIG. 17
  876—Hub of Steering Wheel
First Used in FIGS. 18-20
  880—Transmitter (3 Button FOB)
  882—$3^{rd}$ Button
First Used in FIGS. 22-24
  890—Magnetic Connector Rest
  891—Base
  892—Clip
  894—Landing Pad
  896—Protrusion Receiving Area
First Used in FIG. 25
  900—Headset
  901—User
  902—Fluid Conduit
  904—Outlet Port
  906—Magnetic Quick Connect
  908—Male Connector
  909—Protrusion
  910—Female Connector
  911—O-Ring
  912—Mounting Bracket
  914—Head Bracket
  916—Opposing Support Members
  918—Resilient U-Shaped Spring Member
  920—Neck Pad
  922—Adjustable Frame
  924—Flexible Tube
  926—Articulating Joints
First Used in FIG. 27
  930—Body
  931—Actuation button for microswitch
  932—Opposing longitudinal extensions
  934—Slots
First Used in FIG. 28
  935—Hydration System
  936—Fluid Delivery System
  938—Integrated Headset
First Used in FIG. 29
  960—Refill reservoir
  961—Hydration liquid
  962—Lid
  964—Refill Cap
  966—Refill hose
First Used in FIG. 30
  940—Initiate Change of State Monitoring Process
  942—Wait for Next Command Signal Step
  944—Receive New Command Signal Step
  946—Determine Command Step
  948—Is System Paused? Step
  950—Is Command a Pause Command? Step
  952—Execute Command Step
  954—Is Command a Resume Command?
  956—Set System to "Running" Step
  958—Set System to "Paused" Step While various embodiments of an improved personal hydration system and its respective components have been presented in the foregoing disclosure, numerous modifications, alterations, alternate embodiments, and alternate materials may be contemplated by those skilled in the art and may be utilized in accomplishing the various aspects of the described inventions. For example, the magnetic quick connects described above may be used in fluid delivery systems and devices other than personal hydration systems, such as the one shown in FIG. 1. They may also be used in the delivery of gasses in addition to liquids. Thus, it is to be clearly understood that the present description is made only by way of example and not as a limitation on the scope of any of the inventions that may be claimed in the claims that follow.

What is claimed:

1. A hydration system comprising:
a portable fluid reservoir,
a plurality of components in fluid communication with one another and collectively defining a fluid delivery path for delivering fluid from the portable fluid reservoir to a user's mouth, the fluid delivery path in communication with the reservoir;
a magnetic quick connect interposed in the fluid delivery path, wherein
the plurality of components comprise a headset at a distal end of the fluid delivery path;
the headset includes a support structure configured to support the headset on headgear adapted to be worn on a user's head;
a proximal end of the headset comprises the magnetic quick connect;
the fluid delivery path between the portable fluid reservoir and the magnetic quick comprises a hose that has a length, wall thickness, outer diameter and Shore Durometer hardness such that when a user is wearing the headset or when a user is wearing headgear to which the headset is mounted turns his or her head it does not cause the magnetic quick connect to disconnect; and
the magnetic quick connect comprises a first coupling member and a second coupling member, and an axial pull force that is greater than 48 ounce-force and less than 128 ounce-force between the first coupling member and second coupling member is required to decouple the coupling members in the axial direction.

2. A hydration system according to claim 1, wherein the first coupling member comprises a male coupling member and the second coupling member comprises a female coupling member.

3. A hydration system comprising:
a portable fluid reservoir;
a plurality of components in fluid communication with one another and collectively defining a fluid delivery path for delivering fluid from the portable fluid reservoir to a user's mouth, the fluid delivery path in communication with the reservoir;
a magnetic quick connect interposed in the fluid delivery path, wherein
the plurality of components comprise a headset at a distal end of the fluid delivery path;
the headset includes a support structure configured to support the headset on headgear adapted to be worn on a user's head;
a proximal end of the headset comprises the magnetic quick connect;
the fluid delivery path between the portable fluid reservoir and the magnetic quick comprises a hose that has a length, wall thickness, outer diameter and Shore Durometer hardness such that when a user is wearing the headset or when a user is wearing headgear to which the headset is mounted turns his or her head it does not cause the magnetic quick connect to disconnect; and
the magnetic quick connect comprises a first coupling member and a second coupling member and the first coupling member and second coupling member may be decoupled by pivoting one coupling member relative to the other coupling member through the application of a torque that is in the range of about 16 ounce-inches and 72 ounce-inches to the pivoted coupling member.

4. A hydration system according to claim 3, wherein the support structure is (i) configured to attach to the headgear and support the headset on the headgear once attached, (ii) already attached to the headgear, or (iii) at least partially formed integral with the headgear.

5. A hydration system according to claim 3, wherein the support structure comprises a mounting bracket that is (i) attached to the headgear, or (ii) configured to attach to the headgear.

6. A hydration system according to claim 5, wherein the support structure is configured to attach to a helmet.

7. A hydration system according to claim 6, wherein the helmet comprises a motorcycle helmet.

8. A hydration system according to claim 3, wherein the Shore Durometer hardness of the hose is in the range of about 50 A to 70 A on the Shore A scale.

9. A hydration system according to claim 3, wherein the hydration system comprises a personal hydration system designed to be carried by a user.

10. A hydration system according to claim 3, further comprising a pump interposed in the fluid delivery path between the reservoir and the magnetic quick connect.

11. A hydration system according to claim 3, wherein the pivoted coupling member comprises a lever arm of greater than or equal to about 1.0 inches and less than or equal to about 2 inches from the pivot point.

12. A hydration system according to claim 3, wherein the headgear comprises a helmet and at least a portion of the support structure is formed integral with the helmet.

13. A fluid delivery system for a hydration system, the fluid delivery system comprising:
a plurality of components in fluid communication with one another and collectively defining a fluid delivery path, the fluid delivery path having a proximal end adapted to be attached to a fluid reservoir so as to establish fluid communication between the fluid delivery path and the fluid reservoir, the fluid delivery path having an exit port at a distal end for delivering liquid from the fluid reservoir to a user's mouth;
a magnetic quick connect interposed in the fluid delivery path, wherein
the plurality of components comprise a headset at a distal end of the fluid delivery path;
the headset includes a support structure configured to support the headset on headgear adapted to be worn on a user's head;
a proximal end of the headset comprises the magnetic quick connect;
the magnetic quick connect comprises a male coupling member and a female coupling member;

the fluid delivery path between the proximal end of the fluid delivery path and an upstream end of the magnetic quick connect comprises a hose;

the hose is configured so that when the proximal end is connected to the fluid reservoir and a user is wearing the headset or when the fluid delivery system includes a headgear and a user is wearing the headgear to which the headset is mounted turns his or her head it does not cause the coupling members of the magnetic quick connect to uncouple front one another; and the magnetic quick connect comprises a first coupling member and a second coupling member, and an axial pull force that is greater than 48 ounce-force and less than 128 ounce-force between the first coupling member and second coupling member is required to decouple the coupling members in the axial direction.

14. A hydration system according to claim 13, wherein the first coupling member comprises a male coupling member and the second coupling member comprises a female coupling member.

15. A fluid delivery system for a hydration system, the fluid delivery system comprising:

a plurality of components in fluid communication with one another and collectively defining a fluid delivery path, the fluid delivery path having a proximal end adapted to be attached to a fluid reservoir so as to establish fluid communication between the fluid delivery path and the fluid reservoir, the fluid delivery path having an exit port at a distal end for delivering liquid from the fluid reservoir to a user's mouth;

a magnetic quick connect interposed in the fluid delivery path, wherein the plurality of components comprise a headset at a distal end of the fluid delivery path;

the headset includes a support structure configured to support the headset on headgear adapted to be worn on a user's head;

a proximal end of the headset comprises the magnetic quick connect;

the magnetic quick connect comprises a male coupling member and a female coupling member;

the fluid delivery path between the proximal end of the fluid delivery path and an upstream end of the magnetic quick connect comprises a hose;

the hose is configured so that when the proximal end is connected to the fluid reservoir and a user is wearing the headset or when the fluid delivery system includes a headgear and a user is wearing the headgear to which the headset is mounted turns his or her head it does not cause the coupling members of the magnetic quick connect to uncouple front one another; and the magnetic quick connect comprises a first coupling member and a second coupling member and the first coupling member and second coupling member may be decoupled by pivoting one coupling member relative to the other coupling member through the application of a torque that is in the range of about 16 ounce-inches to 72 ounce-inches to the pivoted coupling member.

16. A fluid delivery system according to claim 15, wherein the plurality of components comprise a connector at the proximal end of the fluid delivery path for connecting the fluid delivery path to the fluid reservoir, and wherein the connector is a male or female connector of a mechanical quick connect.

17. A fluid delivery system according to claim 15, wherein the support structure is (i) configured to attach to the headgear and support the headset on the headgear once attached, (ii) attached to the headgear, or (iii) at least partially formed integral with the headgear.

18. A fluid delivery system according to claim 15, wherein the support structure comprises a mounting bracket and the mounting bracket is (i) attached to the headgear, or (ii) configured to attach to the headgear.

19. A fluid delivery system according to claim 15, wherein the hose has a Shore Durometer hardness in the range of about 50 A to 70 A on the Shore A scale.

20. A fluid delivery system according to claim 15, wherein the pivoted coupling member comprises a lever arm of greater than or equal to about 1.0 inches and less than or equal to about 2 inches from the pivot point.

21. A fluid delivery system according to claim 15, wherein the support structure is configured to support the headset on the headgear so that when the headgear is worn on a user's head at least a portion of the magnetic quick connect will be disposed behind the user's ear.

22. A fluid delivery system according to claim 21, wherein the headgear is a helmet.

23. A fluid delivery system according to claim 16, wherein a pump is interposed in the fluid delivery path between the connector at the proximal end and the magnetic quick connect.

24. A fluid delivery system according to claim 23, wherein the male or female member of the mechanical quick connect is mounted in a pump housing disposed around the pump and connector, and the housing is shaped such that the mounted male or female member can still be coupled with, and decoupled from, a mating member of the mechanical quick connect.

* * * * *